(12) United States Patent
Chibber et al.

(10) Patent No.: US 7,998,943 B2
(45) Date of Patent: *Aug. 16, 2011

(54) CORE 2 GLCNAC-T INHIBITORS III

(75) Inventors: Rakesh Chibber, Exeter (GB); Russell Hagan, London (GB)

(73) Assignee: BTG International Limited, London (GB)

(*) Notice: Subject to any disclaimer, the term of this patent is extended or adjusted under 35 U.S.C. 154(b) by 578 days.

This patent is subject to a terminal disclaimer.

(21) Appl. No.: 11/481,256

(22) Filed: Jul. 6, 2006

(65) Prior Publication Data

US 2007/0010462 A1    Jan. 11, 2007

(30) Foreign Application Priority Data

Jul. 6, 2005    (GB) .................................. 0513881.3

(51) Int. Cl.
    *A01N 43/04* (2006.01)
    *A61K 31/715* (2006.01)

(52) U.S. Cl. ................ 514/61; 514/25; 514/33; 514/35; 514/54

(58) Field of Classification Search ......................... None
See application file for complete search history.

(56) References Cited

U.S. PATENT DOCUMENTS

| | | | |
|---|---|---|---|
| 4,602,003 A | 7/1986 | Malinow | |
| 5,104,856 A | 4/1992 | Esko et al. | |
| 5,360,733 A | 11/1994 | Fukuda et al. | |
| 5,461,143 A | 10/1995 | Wong et al. | |
| 5,470,879 A | 11/1995 | Sauvaire et al. | |
| 5,486,510 A | 1/1996 | Bouic et al. | |
| 5,589,182 A | 12/1996 | Tashiro et al. | |
| 5,624,832 A | 4/1997 | Fukuda et al. | |
| 5,658,778 A | 8/1997 | Fukuda et al. | |
| 5,684,134 A | 11/1997 | Fukuda et al. | |
| 5,827,884 A | 10/1998 | Obagi | |
| 5,843,707 A | 12/1998 | Larsen et al. | |
| 5,880,091 A | 3/1999 | Cummings et al. | |
| 5,886,029 A | 3/1999 | Dhaliwal | |
| 5,952,393 A | 9/1999 | Sorkin, Jr. | |
| 5,958,770 A | 9/1999 | Cham et al. | |
| 5,965,449 A | 10/1999 | Novak | |
| 5,985,936 A | 11/1999 | Novak | |
| 5,997,877 A | 12/1999 | Chang | |
| 6,042,834 A | 3/2000 | Baraka | |
| 6,087,353 A | 7/2000 | Stewart et al. | |
| 6,131,578 A | 10/2000 | King et al. | |
| 6,197,832 B1 | 3/2001 | Sorkin, Jr. | |
| 6,294,157 B1 | 9/2001 | Rubinstenn et al. | |
| 6,346,267 B1 | 2/2002 | Fry et al. | |
| 6,383,514 B1 | 5/2002 | Weitkemper et al. | |
| 6,407,085 B1 | 6/2002 | Kief | |
| 6,451,355 B1 | 9/2002 | Reisner | |
| 6,593,301 B1 | 7/2003 | Ma et al. | |
| 6,635,461 B1 | 10/2003 | Schwientek et al. | |
| 6,787,151 B2 | 9/2004 | Meijer et al. | |
| 6,933,291 B2 | 8/2005 | Qi et al. | |
| 6,998,501 B1 | 2/2006 | Wright et al. | |
| 2002/0016314 A1 | 2/2002 | Schersi | |
| 2002/0018811 A1 | 2/2002 | Penteado et al. | |
| 2002/0098563 A1 | 7/2002 | Korczak et al. | |
| 2002/0107292 A1 | 8/2002 | Bortlik et al. | |
| 2002/0156051 A1 | 10/2002 | Kutney et al. | |
| 2002/0183294 A1 | 12/2002 | Barraclough et al. | |
| 2002/0193317 A1 | 12/2002 | Xia et al. | |
| 2003/0004147 A1 | 1/2003 | Barraclough et al. | |
| 2003/0096316 A1 | 5/2003 | Wester | |
| 2003/0148962 A1 | 8/2003 | Guan et al. | |
| 2004/0033521 A1 | 2/2004 | Korczak et al. | |
| 2004/0038923 A1 | 2/2004 | Marth et al. | |
| 2004/0049352 A1 | 3/2004 | Andre et al. | |
| 2004/0203111 A1 | 10/2004 | Schwientek et al. | |
| 2004/0220115 A1 | 11/2004 | Cham | |
| 2004/0249138 A1 | 12/2004 | Lawson | |
| 2006/0052351 A1 | 3/2006 | Platt et al. | |
| 2007/0254847 A1 | 11/2007 | Liu et al. | |
| 2008/0318875 A1 | 12/2008 | Chibber | |

FOREIGN PATENT DOCUMENTS

CA    2 186987    4/1998

(Continued)

OTHER PUBLICATIONS

Mimaki et al. Phytochemistry (1996), vol. 42, pp. 1065-1070.*

(Continued)

*Primary Examiner* — Patrick Lewis
(74) *Attorney, Agent, or Firm* — Nixon & Vanderhye

(57) ABSTRACT

A method of treating a subject in need of therapy for a condition involving detrimental activity of the enzyme core 2 GlcNAc-T is provided, comprising administration of a therapeutically effective amount of an inhibitor of core 2 GlcNAc-T of the formula I to a patient in need thereof

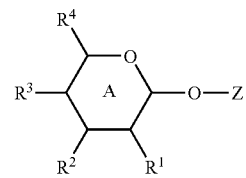

wherein
$R^1$ is H, —OH, $C_{1-6}$ alkoxy, —$NR^5R^6$, or Sac 1;
$R^2$ is H, —OH, $C_{1-6}$ alkoxy or Sac 2;
$R^3$ is H, —OH, $C_{1-6}$ alkoxy or Sac 3;
$R^4$ is H, $C_{1-6}$ alkyl, $C_{1-6}$ hydroxyalkyl or $C_{1-6}$-alkoxy-$C_{1-6}$-alkyl;
$R^5$ is H, $C_{1-6}$ alkyl or $C_{1-6}$ acyl;
$R^6$ is H, $C_{1-6}$ alkyl or $C_{1-6}$ acyl;
Sac 1 Sac 2 and Sac 3 are independently selected saccharide moieties, and
Z is a steroid moiety;
or a pharmaceutically acceptable salt, ether or ester form thereof.

54 Claims, No Drawings

FOREIGN PATENT DOCUMENTS

| | | |
|---|---|---|
| CA | 2 335 436 | 8/2001 |
| CN | 1 237 583 A | 12/1999 |
| CN | 1237583 A | 12/1999 |
| CN | 1243129 A | 2/2000 |
| CN | 1361111 A | 12/2000 |
| CN | 1361111 A | 7/2002 |
| CN | 1 397 545 | 2/2003 |
| CN | 1 511 535 | 7/2004 |
| CN | 1 562 064 A | 1/2005 |
| DE | 4303214 A1 | 11/1994 |
| EP | 0 251 197 A2 | 1/1988 |
| EP | 0 251 197 A3 | 1/1988 |
| EP | 1 316 608 A1 | 6/2003 |
| EP | 0 850 243 B1 | 10/2003 |
| EP | 1 800 685 A1 | 6/2007 |
| JP | 03271224 A | 3/1991 |
| JP | 2004-143126 | 5/2004 |
| RU | 2 027 434 C1 | 1/1995 |
| RU | 2027434 | 1/1995 |
| SU | 833254 | 5/1981 |
| WO | WO 95/17182 A1 | 6/1995 |
| WO | WO 95/21199 A1 | 8/1995 |
| WO | WO 95/35294 A1 | 12/1995 |
| WO | WO 97/06176 A2 | 2/1997 |
| WO | WO 97/47298 A1 | 12/1997 |
| WO | WO 98/06405 A1 | 2/1998 |
| WO | 98/14459 | 4/1998 |
| WO | WO 98/33494 | 8/1998 |
| WO | WO 98/33494 A1 | 8/1998 |
| WO | WO 99/25197 | 5/1999 |
| WO | WO 99/25197 A1 | 5/1999 |
| WO | WO 99/39715 A1 | 8/1999 |
| WO | WO 99/53925 A1 | 10/1999 |
| WO | WO 00/31109 | 6/2000 |
| WO | WO 00/31109 A1 | 6/2000 |
| WO | WO 00/52029 A1 | 9/2000 |
| WO | WO 00/61153 | 10/2000 |
| WO | WO 00/78789 A1 | 12/2000 |
| WO | WO 01/32679 A2 | 5/2001 |
| WO | 01/58932 | 8/2001 |
| WO | WO 01/83717 A2 | 11/2001 |
| WO | WO 01/87548 | 11/2001 |
| WO | WO 02/03996 A1 | 1/2002 |
| WO | WO 02/24212 A1 | 3/2002 |
| WO | WO 02/069980 A2 | 9/2002 |
| WO | WO 02/087548 A1 | 11/2002 |
| WO | 03/043433 | 5/2003 |
| WO | 03/066679 | 8/2003 |
| WO | WO 03/070261 A1 | 8/2003 |
| WO | WO 03/075931 A1 | 9/2003 |
| WO | 03/092394 | 11/2003 |
| WO | WO 2004/002497 A1 | 1/2004 |
| WO | WO 2004/019960 A2 | 3/2004 |
| WO | WO 2004/029068 A1 | 4/2004 |
| WO | WO 2004/048938 A2 | 6/2004 |
| WO | WO 2004/062675 A1 | 7/2004 |
| WO | WO 2004/064852 A1 | 8/2004 |
| WO | 2004/074461 | 9/2004 |
| WO | WO 2004/093662 A2 | 11/2004 |
| WO | WO 2004/111196 A2 | 12/2004 |
| WO | WO 2005/060977 A1 | 7/2005 |
| WO | WO 2005/084323 A2 | 9/2005 |
| WO | WO 2005/120535 A1 | 12/2005 |
| WO | 2006/034655 | 4/2006 |
| WO | WO 2006/034655 A1 | 4/2006 |
| WO | WO 2006/034655 A1 | 6/2006 |
| ZA | 00135190.7 | 1/2005 |

OTHER PUBLICATIONS

Co-Pending U.S. Appl. No. 11/472,554, filed Jun. 22, 2006.
Co-Pending U.S. Appl. No. 10/584,470, filed Jun. 22, 2006.
Co-Pending U.S. Appl. No. 11/481,255, filed Jul. 6, 2006.
Chibber, R., et al; "Activity of the Glycosylating Enzyme, Core 2 GlcNAc (β1,6) Transferase, is Higher in Polymorphonuclear Leukocytes From Diabetic Patients Compared With Age-Matched Control Subjects"; *Diabetes*; vol. 49; pp. 1724-1730 (2000).

Chibber, R., et al; "Protein Kinase C β2-Dependent Phosphorylation of Core 2 GlcNAc-T Promotes Leukocyte-Endothelial Cell Adhesion"; *Diabeties*; vol. 52; pp. 1519-1527 (2003).
Ellies, L.G., et al; "Core 2 Oligosaccharide Biosynthesis Distingjishes between Selectin Ligands Essential for Leukocyte Homing and Inflammation"; *Immunity*; vol. 9, pp. 881-890 (1998).
Goekjian, P.G., et al; "Protein kinase C inhibitors as novel anticancer drugs"; *Expert Opin. Investig. Drugs*; vol. 10, No. 12; pp. 2117-2140 (2001).
Hartung, Hans-Peter, MD; et al; "Circulating Adhesion Molecules and Tumor Necrosis Factor Receptor in Multiple Sclerosis: Correlation with Magnetic Resonance Imaging"; *Annals of Neurology*; vol. 38, No. 2; pp. 186-193 (1995).
Hindsgaul, O., et al; "Evaluation of Deoxygenated Oligosaccharide Acceptor Analogs as Specific Inhibitors of Glycosyltransferases"; *The Journal of Biological Chemistry*; vol. 266, No. 27; pp. 17858-17862 (1991).
Joshi, J., et al; "Chemistry of Ayurvedic Crude Drugs: Part VIII[a]-Shatavari-2: Structure Elucidation of Bioactive Shatavarin-I & other Glycosides[b,c]"; *Indian Journal of Chemistry*; vol. 27B; pp. 12-16 (1988).
Kim, S.Y., et al; "Inhibition of Mouse Ear Edema by Steroidal and Triterpenoid Saponins"; *Arch Pharm Res.*; vol. 22, No. 3, pp. 313-316 (1999).
Kuhns, W., et al; "Processing O-glycan core 1, Galβ1-3GalNAcα-R. Specificities of core 2, UDP-GlcNAc: Galβ1-3GalNAc-R(GlcNAc to GalNAc)β6-N-acetylglucosaminyltransferase and CMP-sialic acid: Galβ1-3GalNAc-R α3-sialyltransferase"; *Glycoconjugate Journal*; vol. 10; pp. 381-394 (1993).
Matsuda, H., et al; "Protective Effects of Steroid Saponins from *Paris polyphylla* var. *yunnanensis* on Ethanol- or Indomethacin-Induced Gastric Mucosal Lesions in Rats: Structural Requirement for Activity and Mode of Action"; *Bioorganic & Medicinal Chemistry Letters*; vol. 13; pp. 1101-1106 (2003).
Orlacchio, A., et al; "Activity levels of a β1, 6 N-acetylglucosaminyltransferase in lymphomonocytes from multiple sclerosis patients"; *Journal of Neurological Sciences*; vol. 151; pp. 177-183 (1997).
Toki, D., et al; "Inhibition of UDP-GlcNAc:Galβ1-3GalNAc-R (GlcNAc to GalNAc)β6-N-acetylglucosaminyltransferase from acute myeloid leukaemia cells by photoreactive nitrophenyl substrate derivatives"; *Biochemical and Biophysical Research Communications*; vol. 198, No. 2; pp. 417-423 (1994).
Washington, R., et al; "Expression of Immunologically Relevant Endothelial Cell Activation Antigens on Isolated Central Nervous System Microvessels from Patients with Multiple Sclerosis"; *Ann. Neurol*; vol. 35, No. 1; pp. 89-97 (1994).
Li, Cheng-Ming, et al; "Development of monoclonal antibodies against bovine mucin core 2 β6 N-acetylglucosaminyltransferase"; *Glycoconjugate Journal*; vol. 16; pp. 555-562 (1999).
Molham Al-Habori et al "Pharmacological properties"; Fenugreek The genus Trigonella Edited by Georgios A. Petropoulos, pp. 162-182.
N M Ammar et al "Study of the anti-inflammatory activity of some medicinal edible plants growing in Egypt", Journal of Islamic Academy of Sciences 10:4, 113-122.
Droogan A G et al "Serum and cerebrospinal fluid levels of soluble adhesion molecules in multiple sclerosis: predominant intrathecal release of vascular cell adhesion molecule-1"; Journal of Neuroimmunology 64 (1996) 185-191.
Shinya Hanashima et al "Systematic Synthesis of Bisubstrate-Type Inhibitors of N-Acetylglucosaminyltransferases" Chem. Eur. J. 2006, 12, 3449-3462.
Mohamed S Kamel et al, "Studies on *Balanites aegyptiaca* Fruits, an Antidiabetic Egyptian Folk Medicine"; Chemical & Pharmaceutica Bulletin 1991, 39(5), 1229-1233.
Takao Konoshima et al "Anti-Aids Agents, 21 Triterpenoid saponins as anti-HIV principles from fruits of gleditsia Japonica and gymnocladus chinesis and a structure-activity correlation"; Journ of Nat. Prods. vol. 58, No. 9, pp. 1372-1377, Sep. 1995.
Laurence A Lasky, "Selectin-Carbohydrate interactions and the initiation of the inflammatory response", Annual Review of Biochemistry 1995 vol. 64, pp. 113-139.

Daniel Lazarevia et al; "Artificial N-functionalised UDP-glucosamine analogues as modified substrates for N-acetylglycosaminyl transferases" Carbohydrate Research 2006, vol. 341(5), 569-576.

Hiromichi Matsuura; "Saponins in Garlic as Modifiers of the Risk of Cardiovascular Disease"; Journal of Nutrition 131, 1000S-1005S, 2001.

John G Ondeyka et al; "Discovery of structurally diverse natural product antagonists of chemokine receptor CXCR3"; Molecular Diversity (2005), 9, 123-129.

Carlo A Palmerini et al "An approach for fluoremetric determination of glycosyltransferase activities", Glycoconjugate Journal (1996) 13, 631-636.

Helen Skaltsa, "Chemical Constituents" , Fenugreek The genus Trigonella Edited by Georgios A. Petropoulos, pp. 132-161.

M M Vaghefi et al; "Synthesis of Glycopyranosylphosphonate Analogues of Certain Natural Nucleoside Diphosphate Sugars as Potential Inhibitors of Glycosyltransferases", Journal of Medicinal Chemistry, 1987, (30), 1383-1391.

M M Vaghefi et al, "Synthesis of certain nucleoside methylenediphosphonate sugars as potential INHIB", Journal of Medicinal Chemistry 1987, 30 1391-1399.

Rita Aquino et al, "Furostanol Oligosides from *Tamus communis*", Journal of Natural Products vol. 49, No. 6, pp. 1096-1101, Nov.-Dec. 1986.

Jean-Guy Bienvenu et al, "Recombinant Soluble P-Selectin Glycoprotein Ligan-1-Ig Reduces Restenosis through Inhibition of Platelet-Neutrophil Adhesion after Double Angioplasty in Swine", *Circulation*. 27;103(8):1128-34 (2001).

Chen C. et al, *Yunnan Zhiwu Yanjiu*, 9(4), 495-502 (1987).

Chow F. et al., "Macrophages in streptozotocin-induced diabetic nephropathy: potenial role in renal fibrosis" Nephrol Dial Transplant. 19(12):2987-96 (2004).

Dang B et al "Increased PSGL-1 expression on granulocytes from allergic-asthmatic subjects results in enhanced leukocyte recruitment under flow conditions", Journal of Leukocyte Biology, vol. 72,(4), pp. 702-710.

Dedrick R.L. et al , "Adhesition molecules as therapeutic targets for autoimmune diseases and transplant rejection".

Fujita S. et al , "Dammarane Glycosides from Aerial parts of Neoalsomitra Integrifoliola", *Phytochemistry*, 38(2), 465-72 (1995).

Guofeng Gu, et al , "Facile Synthesis of Saponins Containing 2,3-Branched Oligosaccharides by Using Partially Protecgted Glycosyl Donors", J. Org. Chem 2004, 69, 5497-5500.

Haladova M. et al., "Steroids saponins from the petals of Lilium candidum L.", *Pharmazie*, 54(2), 159-160 (1999).

Hansen A. et al., "Evaluation of Cardioprotective Effects of Recombinant Soluble P-Selectin Glycoprotein Ligan-Immunoglobulin in Myocardial Ischemia-Reperfusion Injury by Real-Time Myocardial Contrast Echocardiography" *J Am Coll Cardiol*. 18;44(4):887-91 (2004).

Hans-Peter Hartung et al, "Circulating Adhesion Molecules and Tumor Necrosis Factor Receptor in Multiple Sclerosis: Correlation with Magnetic Resonance Imaging" Ann Neurol 1995; 38(2), 186-193.

Hickey M. et al., "Leukocyte-Endothelial Cell Interactions are enhanced in Dermal Postcapillary Venules of MRL/fas[lpr] (Lupus-Prone) Mice: Roles of P- and E-Selectin[1]" *J Immunol*. 168(9):4728-36 (2002).

Haworth and Hirst, XXII—The Constitution of the Disaccharides. Part V, Vellobiose (Cellose)J. Chem. Soc. 119, 193 (1921).

Ke Hu et al, "Methyl protogracillin (NSC-698792): the spectrum of cytotoxicity against 60 human cancer cell lines in the National Cancer Institute;s anticancer drug screen panel", Anti-cancer Drugs 2001, 12, pp. 541-547.

Ke Hu et al "The Cytotoxity of Methyl Protoneogracillin (NSC-698793) and Gracillin (NSC-698787), Two Steroidal Saponins from the Rhizomes of *Dioscorea Collettii* var. *hypoglauca*, against Human Cancer Cells in vitro", Phytother. Res. 17, 620-626 (2003).

Ke Hu et al "Antineoplastic Agents; 11. Four Furostanol Glycosides from Rhizomes of *Dioscorea Collettii* var. *hypoglauca*", Planta Medica 63 (1997) 161-165.

Hurwitz AA et al "Tumor Necrosis Factor α Induces Adhesion Molecule Expression on Human Fetal Astrocytes", J. Exp. Med, 1992 vol. 176, Dec. 1992 pp. 1631-1636.

Kentaro Inoue et al, "Purification and characterization of furostanol glycoside 26-O-β-glucosidase from *Costus speciosus* rhizomes", FEDS Letters, 278 (1996) pp. 157-160.

Inoue T. et al., "Blockade of PSGL-1 attenuates CD14 +monocytic cell recruitment in intestinal mucosa and ameliorates ileitis in SAMP1/Yit mice", *J Leukoc Biol*. 77(3):287-95 (2005).

Toshio Kawasaki et al, "Furostanol Bisglycosides Corresponding to Dioscin and Gracillin", Chem Pharm Bull, 22990 2164-2175 (1074).

Kessar S. et al., "Synthetic Studies in Steroidal Sapogenins and Alkaloids-III" *Tetrahedron*. 24(2):887-92 (1968).

|Kessar S et al., "Synthetic Studies in Steroidal Sapogenins and Alkaloids-V", Tetrahedron vol. 24, pp. 899-904 (1968).

Kessar S et al., "Synthetic Studies in Steroidal Sapogenins and Alkaloids-VI", Tetrahedron vol. 24, pp. 905-907 (1968).

Ravindra Kumar et al., "Core 1 β-1,6-N-Acetylglucosaminyltransferase Enzyme Activity is Critical for P-Selectin Glycoprotein Ligand-1 Binding to P-Selectin", Blood, vol. 88, No. 10, pp. 3872-3879 (1996).

Martina Lahmann et al.,"A facile approach to diosgenin and furostan type saponins bearing a 3β-chacotriose moiety"., Carbohydrate Research 337 (2002) 2153-2159.

Marion Lanteri et al., "Altered T cell surface glycosylation in HIV-1 infection results in increased susceptibility to galectin-1-induced cell death", Glycobiology vol. 13, No. 12, pp. 909-918 (2003).

Sohpie Lautrette et al., "A new method of solvent free 0- and N-glycosylation using activated carbon fiber 9ACF) as a promoter. Application to the synthesis of saponin and nucleoside analogues", Chem Commun. (2004) pp. 586-587.

Chuan Li et al., "Synthesis of diosgenyl α-L-rhamnopyransoyl-(1→2)-[β-D-glycopyranosyl-(1→3)]-β-D-glucopyranoside (gracillin) and related saponins", Carbohydrate Research 306 (1998) 189-195.

Ming Li et al., "Synthesis of monomethylated dioscin derivatives and their antitumor activities", Carbohydrate Research 338 (2003) 117-121.

Liu C. et al, Yaoxue Xuebao, (1983) vol. 18, p. 8 pp. 597-606.

Hongwei Liu et al ., "Two new Pregnane Glycosides from *Dioscorea futschauensis* R. Kunth"., Chem. Pharm. Bull. 51(9) 1089-1091 (2003).

Robert W McMurray et al., "Adhesion Molecules in Autoimmune Disease"., Semin. Arthritis and Rheumatism vol. 25, No. 4, Feb. 1996, pp. 215-233.

Yoshihiro Mimaki et al., "Steroidal Saponins from the bulbs of *Lilium Regale and L. Henryi*"., Phytochemistry, vol. 33 No. 3 pp. 675-682, 1993.

Yoshihiro Mimaki et al., "Steroidal Saponins from the bulbs of *Lilium longiglorum* and their antitumour-promoter activity"., Phytochemistry, vol. 37, No. 1 pp. 227-232 (1994).

Yoshihiro Mimaki et al., "New Steroidal Constituents from the Bulbs of *Lilium candidum*", Chem. Pharm. Bull 46 (11) 1829-1832 (1998).

Yoshihiro Mimaki et al., "Steroidal Saponins from the Rhizomes of *Paris polyphylla* Var. *Chinensis* and Their Cytotoxic Activity on HL-60 Cells", Natural Product Letters Vo. 14(5), pp. 357-364.

Daniel Myers, et al., "New and Effective Treatment of Experimentally Induced Venous Thrombosis with Anti-inflammatory rPSGL-Ig", Throm Haemost 2002, 87, 374-82.

Osamu Nakamura, et al., "Steroidal Saponins from the Bulbs of *Lilium speciosum x L. Nobilissinzum* 'Star Gazer' and their antitumour-promoter activity", Phytochemistry, vol. 36, No. 2, pp. 463-467 (1994).

Kenji Oda et al., "Adjuvant and Haemolytic Activities of 47 Saponins Derived from Medicinal and Food Plants"., Biol. Chem. vol. 381, pp. 67-74, Jan. 2000.

Kazutomo Ori et al., "Jatropham Derivatives and steroidal saponins from the Bulbs of *Lilium hansonII*"., Phytochemistry., vol. 31, No. 8, pp. 2767, 2775, (1992).

Purdie and Irvine., "Synthesis from Glucose of an Octamethylated Disaccharide. Methylation of Sucrose and Maltose", J. Chem. Soc. 87 1022 (11905.

Jean-Hugues Renault et al., "Dammarane Saponins from *Zizyphus lotus*", Phytochemistry vol. 44, No. 7., pp. 1321-1327 (1997).
Emile M. Rijcken et al., "Immunoblockade of PSGL-1 attenuates established experimental murine colitis by reduction of leukocyte rolling", Am J Physiol 287, G115-G124, (2004).
Shengmin Sang et al., "Furostanol saponins from *Allim tuberosum*"., Phytochemistry 52 (1999) pp. 1611-1615.
Serban C Stoica et al., "Endothelial Activation in the Transplanted Human Heart from Organ Retrieval to 3 months after Transplantation: An Observational Study", J. Heart Lung/Transplant., 24(5) 593-601 (2005).
Hostettmann, K. et al; Chemistry and pharmacology of natural products; Saponins Cambridge University Press (1995) (extracted book pages).
Erich C Strauss et al ., "Soluble P-Selectin Glycoprotein Ligand 1 Inhibits Ocular Inflammation in a Murine Model of Allergy", Invest Ophthalmol/Vis Sci. 40(7); 1336-421 (1999).
Jean-Francois Tanguay et al., "Prevention of in-stent restenosis via reduction of thrombo-inflammatory reactions with recombinant P-selectin glycoprotein ligand-1", thromb Haemost 2004, 91, 1186-93.
Jean-Francois Theoret et al., "P-Selectin Antagomism with Recombinant P-Selection Glycoprotein Ligand-1 (rPSGLIg) Inhibits Circulating Activated Platelet Binding to Neutrophils Induced by Damaged Arterial Surfaces", J. Pharm and Exper. Therap. vol. 298 No. pp. 658-664.
Akihiko Tobari et al, "Spirostanols obtained by cyclization of pseudosaponin derivatives and comparison of anti-platelet agglutination activities of spirostanol glycosides", Eur. J. Med. Chem 35 (2005) 511-527.
M. Tomova et al., "Steroidal Saponins from Tribulus Terrestris L. with a Stimulating Action on the Sexual Functions", Int. Conf. Chem Biotechnol (1981), 3, 1, 298-302.
I. S Vail'eva et al., "Steroid Saponins from Rhizomes of the Caucasian Yam", Pnkl. Biochim Mikrobiol (1984) 20(3) p. 330-332.
Kai Wang et al., "Recombinant Soluble P-Selectin Glycoprotein Ligand-lg (rPSGL-lg) Attenuates Infarct Size and Myeloperoxidase Activity in a Canine Model of Ischemia-Reperfusion", Thromb Haemost (2002) 88, 149-54.
Shao-Min Wang et al., "Syntheses of acetylated steroid glycosides and selective cleavage of *O*-acetyl groups in sugar moiety", Steroids 69 (2004) 599-604.
Tadayuki Yago et al., "Structurally Distinct Requirements for Binding of P-selectin Glycoprotein Ligand-1 and Sialyl Lewis x to *Anaplasma phagocytophilum* and P-selectin", J. Biol Chem. (2003) vol. 278, No. 39, 37987-37997.
Deng-Jye Yang et al., "Isolation and Identification of Steroidal Saponins in Taiwanese Yam Cultivar (Dioscorea pseudojaponica Yamamoto", J. Agric. Food Chem. (2003) 51, 6438-6444.
Feng Yin et al., "Dammarane-Type Glycosides from *Gynostemma pentaphyllum*", J. Nat. Prod. (2004) 67 pp. 942-952.
Kazuko Yoshikawa et al., "Antisweet Natural Products. VII. Hodulosides I, II, III, IV and V from the Leaves of *Hovenia dulcis* THUNB", Chem Pharm. Bull. 40(9) 2287-2291 (1992).
Kazuko Yoshikawa et al.,"Antisweet Natural Products. VI. Jujubasaponins IV, V and VI from *Zizyphus jujube mill*.", Chem. Pharm. Bull. 40(9) 2275-2278 (1992).
Qing-An Zheng et al., "Steroidal saponins from fresh stem of *Dracaena cochinchinensis*", Steroids 69 (2004) 111-119.
PCT Notification of Transmittal of the International Search Report and the Written Opinion of the International Searching Authority, or the Declaration, with cited references; International Application No. PCT/GB2004/005398, filed Dec. 22, 2004; Applicant's or agent's file Reference No. 500496W001; May 31, 2005.
Cheng, M.S., et al; "Total Synthesis of Methyl Protodioscin: A Potent Agent with Antitumor Activity"; *J. Org. Chem.*; vol. 68; pp. 3658-3662 (2003); Citation May 31, 2005; XP-002328851.
Ravikumar, P.R., et al; "Chemistry of Ayurvedic Crude Drugs: Part VI[a]-(Shatavari-1): Structure of Shatavarin-IV[b,c]"; *Indian Journal of Chemistry*; vol. 26B, pp. 1012-1017 (1987); Citation May 31, 2005; XP-001096221.
Toki, D., et al; "Inhibition of UDP-GlcNAc:Galβ1-3GalNAc-R (GlcNAc to GalNAc)β6-N-acetylglucosaminyltransferase from acute myeloid leukaemia cells by photoreactive nitrophenyl substrate derivatives"; *Biochemical and Biphysical Research Communications*; vol. 193, No. 2; pp. 417-423 (1994); Citation May 31, 2005; XP002922997.
Yoshikawa, M., et al; "Medicinal Foodstuffs. VIII.[1] Fenugreek Seed. (2) : Structures of Six New Furostanol Saponins, Trigoneosides IVa, Va, Vb, VI, VIIb, and VIIIb, From the Seeds of Indian *Trigonella Foenum-Graecum L*."; *Heterocycles*, vol. 47, No. 1; pp. 397-405 (1998); Citation May 31, 2005; XP-001205771.
PCT Notification of Transmittal of the International Search Report and the Written Opinion of the International Searching Authority, or the Declaration, with cited references; International Application No. PCT/GB2006/002301, filed Jun. 22, 2006; Applicant's or agent's file Reference No. 500966WO01 Nov. 15, 2006.
Orlacchio, A., et al; "Activity levels of a β1,6 N-acetylglucosaminyltransferase in lymphomonocytes from multiple sclerosis patients"; *Journal of the Neurological Sciences*; vol. 151; pp. 177-183 (1997); Citation Nov. 15, 2006; XP-002232475.
PCT Notification of Transmittal of the International Search Report and the Written Opinion of the International Searching Authority, or the Declaration, with cited references; International Application No. PCT/GB2006/002500, filed Jul. 6, 2006; Applicant's or agent's file Reference No. 500964WO01 May 25, 2007.
Derwent Publications Ltd., London, GB; AN 2003-664094 & CN 1 415 625 A (Jilin Tianyao Sci & Technology Co. Ltd) May 7, 2003; Citation May 25, 2007; (Abstract) XP-002433233.
Derwent Publications Ltd., London, GB; AN 2001-412294 & JP 2001 072597 A (merican Corp); Mar. 21, 2001; Citation May 25, 2007; (Abstract) XP-002433234.
Derwent Publications Ltd., London, GB; AN 2000-476485 & CN 1 243 129 A (Univ. Shenyang Medicine); Feb. 2, 2000; Citation May 25, 2007; (Abstract) XP-002433235.
Hu, K., et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*, vol. 17, pp. 620-626 (2003); Citation May 25, 2007.
Aquino, R., et al; "Antiviral Activity of Constituents of *Tamus communis*"; *Journal of Chemotherapy*; vol. 3, No. 5; pp. 305-309 (1991); Citation May 25, 2007.
Baek, S.H., et al; "Inactivation of Human Pleural Fluid Phospholipase $A_2$ by Dioscin"; *Arch. Pharm. Res.*; vol. 17, No. 4; pp. 218-222 (1994); Citation May 25, 2007.
Ondeyka, J.G., et al; "Discovery of structurally diverse natural product antagonists of chemokine receptor CXCR3"; *Molecular Diversity*; vol. 9; pp. 123-129 (2005); Citation May 25, 2007.
Sautour, M., et al; "Antifungal steroid saponins from Dioscorca caycnensis. Plant Medica;" *Antimicrobial Activity*; vol. 70(1); pp. 90-92 (2004); Citation May 25, 2007.
PCT Notification of Transmittal of the International Search Report and the Written Opinion of the International Searching Authority, or the Declaration, with cited references; International Application No. PCT/GB2006/002518, filed Jul. 6, 2006; Applicant's or agent's file Reference No. 500965WO01; Dec. 19, 2006.
Derwent Publications Ltd., London, GB; AN 2004-239758; Huang, H., et al; "Medicine composition for treating myocardial ischemia, angina pectoris and cardiac infraction"; & CN 1 465 344 A (Chengdu Diao Pharm Group Co Ltd) Jan. 7, 2004 (Abstract) XP-002409228; Citation Dec. 19, 2006.
Derwent Publications Ltd., London, GB; AN 2005-426073; Wang Jingang; "Dioscin oral disintegration tablet and its preparing method"; & CN 1 586 493 A (Kexinbicheng Medicine Science) Mar. 2, 2005 (Abstract) XP-002409229; Citation Dec. 19, 2006.
Derwent Publications Ltd., London, GB; AN 2002-751531; Zhu Dayuan et al; "Furost saponine analogue and its separatin process and use" & CN 1 184 229 C (Shanghai Inst of Pharmacology) Jan. 12, 2005 (Abstract) XP-002409230; Citation Dec. 19, 2006.
Derwent Publications Ltd., London, GB, AN 2005-631469; Han J. et al; "Medicine for regulating blood fat and treating cardiocerehral disease and preparing method"; & CN 1 615 896 A (Yunnan Prov Medicine Inst) May 18, 2005 (Abstract) XP-002409231; Citation Dec. 19, 2006.

Derwent Publications Ltd., London, GB, AN 2000-443110; Li Pingya et al; "Process for extracting ginsenoside Re, and use of medicine thereof"; & CN 1 242 374 A (Xinliheng Pharmaceutical Scien) Jan. 26, 2000; (Abstract) XP-002409232; Citation Dec. 19, 2006.

Derwent Publications Ltd., London, GB, AN 1998-087548; Junpeng Peng et al; "Anti-thrombosis glucoside medicine"; & CN 1 138 984 A (Radiomedicine Inst Military ME) Jan. 1, 1997; (Abstract) XP-002409233; Citation Dec. 19, 2006.

Derwent Publications Ltd., London, GB, AN 2006-272298; Fu T., et al; "Steroidal saponin pharmaceutical composition, its preparation method and use"; & WO 2006/034655 A (chengdu Diao Pharm Group Co Ltd) Apr. 6, 2006 (Abstract) XP-002409234; Citation Dec. 19, 2006.

Zhang, J., et al; "Effect of six steroidal saponins isolated from anemarrhenae rhizome on platelet aggregation and hemolysis in human blood"; Clinica Chimica Acta; vol. 289; pp. 79-88 (1999); Citation Dec. 19, 2006.

L. S. Akhov et al.2000, Biological Activity of Deltoside from Allium Nutans L. In Saponins in Food, Feedstuffs and Medicinal Plants edited by W Oleszek and A Marston.

Bernadete P. da Silva, et al, A New Bioactive Steroidal Saponin from Agave attenuata; Z. Naturforsch, 57c, 423-428.

Mei Dong et al, Two New Steroidal Saponins from the Rhizomes of Dioscorea panthaica and their Cytotoxic Activity; Planta Med. 67 (2001) 853-857.

M. Dong et al, Steroidal saponins from Dioscorea panthaica and their cytotoxic activity; Pharmazie 59, 294-296 (2004).

B. B. Gaitonde et al; Antioxytocic action of Saponin isolated from Asparagus Racemosus Willd (Shatavari) on Uterine Muscle; Arch. int. Pharmacodyn., 1969, 179, No. 121-129.

Antonio G. Gonzalez et al; Steroidal Saponins from the Bark of Dracaena draco and Their Cytotoxic Activities; J. Nat. Prod. 2003, 66, 793-798.

Juan C. Hernandez et al, Icogenin, a new cytotoxic steroidal saponin isolated from Dracaena draco; Bioorganic & Medicinal Chemistry 12 (2004) 4423-4429.

Hiroschige Hibasami et al, Protodioscin isolated from fenugreek (Trigonella foenumgraecum L). induces cell death and morphological change indicative of apoptosis in leukemic cell line H-60, but not in gastric cancer cell line KATO III; International Journal of Molecular Medicine 11: 23-26, 2003.

Ke Hu et al; Methyl protogracillin (NSC-698792): the spectrum of cytotoxicity against 60 human cancer cell lines in the National Cancer Institute's anticancer drug screen panel, Anti-Cancer Drugs 2001, 12, pp. 541-547.

M. A. Lacaille-Dubois et al; a review of the biological and pharmacological activities of saponins: Phytomedicine vol. 2(4), pp. 363-386, 1996.

H.W. Liu et al; Bioactive saponins from Dioscorea futschauensis: Pharmazie 57 (2002) 8 570-572.

Yoshihiro Mimaki et al; Steroidal Saponins from the bulbs of Triteleia Lactea and their inhibitory activity on cyclic amp phosphodiesterase: Phytochemistry, vol. 38, No. 5, pp. 1279-1286, 1995.

Yoshihiro Mimaki et al; Cytotoxic Activities and Structure-Cytotoxic Relationships of Steroidal Saponins: Biol. Pharm. Bull, 24(II) 1286-1289 (2001).

Pierre R Petit et al; Steroid saponins from fenugreek seeds: Extraction, purification, and pharmacological investigation on feeding behaviour and plasma cholesterol: Steroids: 60: 674-680, 1995.

P. Sur et al; Short Communication Trigonella foenum graecum (Fenugreek) Seed Extract as an Antineoplastic Agent: Phytotherapy Research, 15, 257-259 (2001).

Yi-Fei Wang et al; Inhibitory Effects of Some Steroidal Saponins on Human Spermatozoa in vitro: Planta Medica 62 (1996) 130-132.

Ethan Basch et al; Therapeutic Applications of Fenugreek: Alternative Medicine Review vol. 8, No. 1, 2003 pp. 20-27.

Dinesh Puri; Therapeutic Potentials of Fenugreek: Indian J Physiol Pharmacol. 1998; 42(3) pp. 423-424.

L. S. Akhov et al Structure of Steroidal Saponins from Underground Parts of Allium nutans L.; J. Agric. Food Chem. 1999, 47, 3193-3196.

Paul V. Beaum et al; Expression of Core 2 β-1,6-N-Acetylglucosaminyltransferase in a Human Pancreatic Cancer Cell Line Results in Altered Expression of MUC1 Tumor-associated Epitopes; The Journal of Biological Chemistry, vol. 274, No. 35, Issue of Aug. 27, pp. 24641-24648, 1999.

Christopher Broca et al; 4-Hydroxyisoleucine: effects of synthetic and natural analogues on insulin secretion; European Journal of Pharmacology 390 (2000) 339-345.

I. Brockhausen et al; Biosynthesis of O-Glycans in Leukocytes from Normal Donors and from Patients with Leukemia: Increase in O-Glycan Core 2 UDP-GlcNAc:Galβ3GalNAcα-R(GlcNAc to GalNAc)β(1-6)-N-Acetylglucosaminyltransferase in Leukemic Cells; Cancer Research 51, 1257-1263, Feb. 15, 1991.

Mao S. Cheng et al; Total Synthesis of Methyl Protodioscin: A Potent Agent with Antitumor Activity; J.Org.Chem. 2003, 68, 3658-3662.

Karen J. Colley; Golgi localization of glycosyltransferases: more questions than answers; Glycobiology vol. 7, No. 1 pp. 1-13, 1997.

Martin Dalziel et al; The Relative Activities of the C2GnT1 and ST3Gal-I Glycosyltransferases Determine O-Glycan Structure and Expression of a Tumor-associated Epitope on MUCI; The Journal of Biological Chemistry Vo. 276, No. 14, Issue of Apr. 6, pp. 11007-11015, 2001.

Matthew D. Davis et al, Diabetic Retinopathy; Diabetes Care, vol. 15, No. 12, Dec. 1992, pp. 1844-1874.

Michael J. Davies et al; The expression of the adhesion molecules ICAM-1, VCAM-1, PECAM, and E-Selectin in Human Atherosclerosis; Journal of Pathology, vol. 171, 223-229 (1993).

Shaojiang Deng et al; Synthesis of three diosgenyl saponins: dioscin, polyphyllin D, and balanitin 7; Carbohydrate Research 317 (1999) 53-62.

Yuguo Du et al; Synthesis of Saponins Using Partially Protected Glycosyl Donors; Organic Letters 2003, vol. 5, No. 20, 3627-3630.

Umit Guray et al; Levels of Soluble adhesion molecules in various clinical presentations of coronary atherosclerosis; International Journal of Cardiology 96 (2004) 235-240.

Umit Guray et al; Poor coronary collateral circulation is associated with higher concentrations of soluble adhesion colecules in patients with single-vessel desease; Coronary Artery Disease 2004, 15: 413-417.

Elizabeth A. Higgins et al; Aberrant O-Linked Oligosaccharide Biosynthesis in Lymphocytes and Platelets from Patients with the Wiskott-Aldrich Syndrome; The Journal of Biological hemistry: vol. 266, No. 10 Issue of Apr. 5, pp. 6280-6290.

Ronald Klein et al; The Wisconsin Epidemiologic Study of Diabetic Retinopathy: X. Four-Year Incidence and Progression of Diabetic Retinopathy When Age at Diagnosis is 30 years or More; Arch Ophthalmol 1989; 107: 244-249.

Eva M. Kohner et al; Diabetic Retinopathy in Diabetic Angiopathy, Tooke J.E., pp. 233-247, Oxford University Press (1999).

Daisuke Koya et al; Perspectives in Diabetes: Protein Kinase C Actibvation and the Development of Diabetic Complications; Diabetes, vol. 47, 859-866, 1998.

Diasuke Koya et al; Overexpression of core 2, N-acetylglycosaminyltransferase enhances cytokine actions and induces hypertrophic myocardium in transgenic mice: FASEB J. 13, 2329-2337 (1999).

Kensuke Kumamoto et at; Specific Detection of Sialyl Lewis X Determinant Caried on the Mucin GlcNAcβ1→6GalNAcα Core Structure as a Tumor-Associated Antigen; Biochemical and Biophysical Research Communications 247, 514-517 (1998).

Suzanne Laferte et al; Glycosylation-dependent Collagen-binding Activities of Two Membrane Glycoproteins in MDAY-D2 Tumor Cells: Cancer Research 48, 4743-4748, Sep. 1, 1988.

Chuan Li, et al; Synthesis of Diosgenyl α-L-rhamnopyranosyl-(1→2)β[13-D-glucopyranosyl-(1→3)]-β-D-glucopyranoside (gracillin) and related saponins; Carbohydrate Research 306 (1998) 189-195.

Bing Li et al; An improved synthesis of the saponin, polyphyllin D; Carbohydrate Research 331 (2001) 1-7.

Emi Machida et al; Clinicopathological Significance of Core 2 β,6-N-Acetylglucosaminyltransferase Messenger RNA Expressed in the Pulmonary Adenocarcinoma Determined by in situ hybridization; Cancer Research 61, 2226-2231, Mar. 1, 2001.

Kentaro Maemura et al; Poly-N-acetyllactosaminyl O-Glycans attached to Leukosialin; The Journal of Biological Chemistry, vol. 267, No. 34, Issue of Dec. 5, pp. 24379-24386.

Marja-Leena Majuri et al; Recombinant E-selectin-protein mediates tumor cell adhesion via sialyl-Lea and sialyl-Lex; Biochemical and Biophysical Research Communications, vol. 182, No. 3 1992, Feb. 14, 1992, pp. 1376-1382.

Matthias Meier et al; Protein kinase C activation and its pharmacological inhibition in vascular disease; Vascular Medicine 2000; 5: 173-185.

Yoshihiro Mimaki et al; Steroidal Saponins and Alkaloids from the Bulbs of *Lilium brownie* var. *colchesteri*; Chem. Pharm. Bull 38(11) 3055-3059 (1990).

N T Mulvihill et al ; Inflammation in acute coronary syndromes; Heart 2002, 87, 201-204.

Toshiyuki Murakami et al; Medicinal Foostuffs. XVII. Fenugreek Seed. (3): Structures of New Furostanol-Type Steroids Saponins, Trigoneosides Xa, Xb, XIb, XIIa, XIIb, and XIIIa, from the Seeds of Egyptian *Trigonella Foenum-graecum L*; Chem. Pharma. Bull. 48(7)1994-1000 (2000).

Mitsuru Nakamura et al; Simultaneous core 2 β1→6N-acetylglycosaminyltransferase up-regulation and sialyl-Le expression during activation of human tonsillar B lymphocytes; FEBS Letters 463 (1999) 125-128.

Yoshihiko Nishio et al; Identification and Characterization of a Gene Regulating Enzymatic Glycosylation which is Induced by Diabetes and Hyperglycemia Specifically in Rat Cardiac Tissue; J. Clin. Invest. vol. 96, Oct. 1995, 1759-1767.

Kevin D O'Brien et al; Neovascular Expression of E-Selectin, Intercellular Adhesion Molecule-1, and Vascular Cell Adhesion Molecule-1 in Human Atherosclerosis and Their Relation to Intimal Leukocyte Content; 1996 American Heart Association, In.c. 1996; 93: 672-682.

Katsuyuki Ohmori et al; A Distinct Type of Sialyl Lewis X Antigen Defined by a Novel Monoclonal Antibody is Selectively Expressed on Helper Memory T Cells; Blood, vol. 82, No. 9 (Nov. 1, 1993 pp. 2797-2805.

Hans Paulsen et al; Synthese von modifizierten Derivaten des Disaccharides β-D-Gal-(1→3)-α-D-GalNAc zur Untersuchung der Substratspezifitat der Core-2-β6-GlcNAc-Transferase und α-3-Sialyltransferase der Biosynthese von O-Glycoproteinen: Liebigs Ann. Chem. 1992, 747-758.

George R Pettit et al: Isolation and Structure of Cytostatic Steroidal Saponins from the African Medicanal Plant *Balanites aegyptica*; Journal of Natural Products Vo. 54, No. 6 pp. 1491-1502 Nov.-Dec. 1991.

Friedrich Piller et al; Human T-lymphocyte Activation is Associated with changes in O-Glycam Biosynthesis; The Journal of Biological Chemistry, vol. 263, No. 29, Issue of Oct. 15, pp. 15146-15150, 1988.

Jutta Renkonen et al; Core 2 β1,6-N-acetylglycosaminyltransferases and α1,3-fucosyltransferases regulate the synthesis of O-glycans on selectin ligands on oral cavity carcinoma cells; APMIS 109, 500-6, 2001.

P. R. Ravikumar et al; Chemistry of Ayurvedic Crude Drugs: Part VI-(Shatavari-1):Structure of Shatavarin-IV; Indian Journal of Chemistry vol. 26B, Nov. 1987, pp. 1012-1017.

Osamu Saitoh et al; Expression of Aberrant O-Glycans attached to Leukosialin in Differentiation-deficient HL-60 Cells; Cancer Research 51, 2854-2862, Jun. 1, 1991.

Yutaka Sashida et al; Studies on the Chemical Constituents of the Bulbs of *Lilium mackliniae*; Chem. Pharm. Bull. 39 (9) 2362-2368 (1991).

Yves Sauvaire et al; 4-Hydroxyisoleucine. A novel amino acid potentiator of insulin secretion; Diabetes, vol. 47, Feb. 1998 pp. 206-210.

S C Sharma et al; Oligofurostanosides from *Asparagus Curillus* leaves; Phytochemistry, Vo. 33, No. 3, pp. 683-686, 1993.

R D Sharma et al; Effect of fenugreek seeds on blood glucose and serum lipds in Tyupe 1 diabetes; European Journal of Clinical Nutrition (1990) 44, 301-306.

Kazuhisa Shimodaira et al; Carcinoma-associated Expression of Core 2 β-1,6-N-Acetylglucosaminyltransferase Gene in Human Colorectal Cancer: Role of O-Glycans in Tumor Progression; Cancer Research 57, 5201-5206 Dec. 1, 1997.

Hiroko Shimomura et al; Steroidal Saponins, PardarinosideA-G from the Bulbs of Lilium Pardarinum; Phytochemistry, Vo. 28, No. 11 pp. 3163-3170, 1989.

Markus Sperandio et al; Severe impairment of leukocyte rolling in venules of core 2 glyucosaminyltransferase-deficient mice; Blood, Jun. 15, 2001, vol. 97. No. 12, pp. 3812-3819.

Akiko Takada et al; Contribution of Carbohydrate Antigens Sialyl Lewis A and Sialyl Lewis X to Adhesion of Human Cancer Cells to Vascular Endothelium; Cancer Research 53, 354-361, Jan. 15, 1991.

Shigeru Tsuboi et al; Branched O-linked oligosaccharides ectopically expressed in transgenic mice reduce primary T-cell immune responses; The EMBO Journal vol. 16, No. 21, pp. 6364-6373, 1997.

Shigeru Tsuboi et al; Overexpression of Branched O-Linked Oligosaccharides on T Cell Surface Glycoproteins Impairs Humoral Immune Responses in Transgenic Mice; The Journal of Biological Chemistry Vo. 273, No. 46, Issue of Nov. 13, pp. 30680-30687, 1998.

Shigeru Tsuboi et al; Roles of O-linked oligosaccharides in immune responses; BioEssays 23:46-53, 2001.

Ajit Varki; Special Invited Review: Biological roles of oligosaccharides: all of the theories are correct; Glycobiology Vo. 3, No. 2 pp. 97-130, 1993.

I.S.Vasil'eva et al; Composition and Biological Activity of Steroid Glycosides from Cell Suspensions of *Discorea deltoidea* Wall; Applied Biochemistry and Microbiology, vol. 31, No. 2, 1995 pp. 206-209.

Gerd Walz et al; Recognition by ELAM-1 of the Sialyl-Le Determinant on Myeloid and Tumor Cells; Science, vol. 250 pp. 1132-1135, 1990.

Patricia P. Wilkins et al; Structures of the O-Glycans on P-selectin Glycoprotein Ligand-1 from HL-60 Cells; The Journal of Biological Chemistry, vol. 271, No. 31, Issue of Aug. 2, pp. 18732-18742, 1996.

David Williams et al; Detection in Canine Submaxillary glands of an N-Acetylglucosaminyltransferase which acts on mucin substrates; The Journal of Biological Chemistry, vol . 255, No. 23, Issue of Dec. 10, pp. 11247-11252, 1980.

Masayuki Yoshikawa et al; Medicinal Foodstuffs IV. Fenugreek Seed. (1): Structures of Trigoneosides Ia, Ib, IIa, IIb, IIIa and IIIb, New Furostanol Saponins from the Seeds of Indian *Trigonella Foenum-graecum L*; Chem. Pharm. Bull. 45(1) 81-87 (1997).

Masayuki Yoshikawa et al; Medicinal Foodstuffs, VIII. Fenugreek Seed (2): Structures of six new Furostanol Saponins Trigoneosides IVa, Va, Vb, VI, VIIb, and VIIIb, from the Seeds of Indian *Trigonella Foenum-Graecum L*.; Heterocycles, vol. 47, No. 1, 1998, pp. 397-405.

Shida Yousefi et al; Increased UDP-GlcNAc:Galβ1-3GalNAc-R (GlcNAc to GalNAc) β-1, 6-N-Acetylglucosaminyltransferase Activity in Metastatic Murine Tumor Cell Lines; The Journal of Biological Chemistry, vol. 266, No. 3, Issue of Jan. 25, pp. 1772-1782, 1991.

Biao Yu, A "Double Random" Strategy for the Preparation of Saponin Libraries; J. Comb. Chem. 2001, 3, 404-406.

Biao Yu et al; The first synthetic route to furostan saponins; Tetrahedron Letters 42 (2001) pp. 77-79.

Biao Yu, et al; Glycosyl Trifluoroacetimidates.2. Synthesis of Dioscin and Xiebai Saponin 1; J. Org Chem. 2002, 67, 9099-9102.

Robert A Moreau et al; Phytosterols, phytostanols, and their conjugates in Foods: structural diversity, quantitative analysis, and health-promoting uses; Progress in Lipd Research 41, (2002) 457-500.

Co-pending CIP U.S. Appl. No. 11/980,727, filed Oct. 31, 2007.

Confavreux, C., et al; "Age at disability milestones in multiple sclerosis"; *Brain*; vol. 129; pp. 595-605 (2006).

Confavreux, C., et al; "Natural history of multiple sclerosis: a unifying concept"; *Brain*, vol. 129; pp. 606-616 (2006).

Elovaara, I., et al; "Adhesion Molecules in Multiple Sclerosis"; *Arch Neurol*; vol. 57, pp. 546-551 (2000).

McDonnell, G.V., et al; "Serum soluble adhesion molecules in multiple sclerosis: raised sVCAM-1, sICAM-1 and sE-selectin in primary progressive disease"; *J. Neurol*; vol. 246; pp. 87-92 (1999).

Musso, A.M., et al; "Increased serum levels of ICAM-1, ELAM-1 and TNF-α in inflammatory disorders of the peripheral nervous system"; *Ital. J. Neurol. Sci.*; vol. 15; pp. 267-271 (1994).

Rao, A.V., et al; "The Bioactivity of Saponins: Triterpenoid and Steroidal Glycosides"; *Drug Metabolism and drug interactions*; vol. 17, No. 1-4; pp. 212-235 (2000).
Simmons, R.D., et al; "Sialyl ligands facilitate lymphocyte accumulation during inflammation of the central nervous system"; *Journal of Neuroimmunology*; vol. 41; pp. 123-130 (1992).
Ulbrich, H., et al; "Leukocyte and endothelial cell adhesion molecules as targets for therapeutic interventions in inflammatory disease"; *Trends in Pharmacological Sciences*; vol. 24, No. 12; pp. 640-647 (2003).
VanderElst, I.E., et al; "β1,6 N-Acetylglucosaminyltransferase (core 2 GlcNAc-T) expression in normal rat tissues and different cell lines: evidence for complex mechanisms of regulation"; *Glycobiology*, vol. 8, No. 7; pp. 731-740 (1998).
Washington, R., et al; "Expression of Immunologically Relevant Endothelial Cell Activation Antigens on Isolated Central Nervous System Microvessels from Patients with Multiple Sclerosis"; *Annals of Neurology*; vol. 35, No. 1; pp. 89-97 (1994).
Derwent Publications Ltd., London, GB AN 2001-412294 & JP 2001 072597 A (Mercian) Corp; Mar. 21, 2001; (abstract).
Belozerskaya V, et al, Effect of steroid glycosides on *Neurospora crassa* Membranes; Applied Biochemistry and Microbiology, vol. 30, No. 6 1994 pp. 724-728.
Brockhausen I et al; The separation of liquid chromatography (under elevated pressure) of phenyl, benzyl, and $o$-nitrophenyl glycosides of oligosaccharides. Analysis of substrates and products for four $N$-acetyl-$_D$-Glucosaminyl-transferases involved in mucin synthesis; Carbohydrate Research, 120(1983) pp. 3-16.
Brower Thomas D et al; Rheumatoid Arthritis; Journal of the Kentucky Medical Association, May 1983, pp. 281-286.
Chiang HC et al Xanthine Oxidase Inhibitors from the Roots of Eggplant (Solanum melongena L), J. Enzyme Inhibition 1993, vol. 7, pp. 225-235.
Deepak M et al., Quantitative Determination of the Major Saponin Mixture Bacoside A in *Bacopa monnieri* by HPLC; Phytochemical Analysis 16, pp. 24-29 )2005).
Djerassi C et al., J. Biol Chem. Jan. 1952; 194(1) 115-8.
Eisenreichova E et al ., A new steroidal saponin from the bulbs of *Lilium candidum* ., Pharmazie (2000) 55 (7) pp. 549-550.
Faul William h et al., Side-chain Transformations and Deuterium Labeling in the Steroidal Sapogenin Series., J. Org. Chem. vol. 35, No. 8, 1970 pp. 2571-2585.
Gautam et al ., Immunomodulatory activity of Asparagus racemosus on systemic Th1/Th2 immunity, Implications for immuno adjuvant potential. J. ethnopharmacology, 121, 241-247 (2009).
Girardon P et al., Volatile Constituents of Fenugreek Seeds, Planta Medica 1985, pp. 533-534.
Hayes PY., et al, Structural revision of shatavarins I and IV, the major components from the roots of *Asparagus racemosus*, Tetrahedron Letters 47 (2006) 6965-6969.
Hou C et al., Bacopaside III, Bacopasaponin G, and Bacopasides A, B, and C from *Bacopa Monniera*, J. Nat. Prod 2002, 65 1759-1763.
Hu K et al., Protodioscin (NSC-698 796) Its Spectrum of Cytotoxicity Against Sixty Human Cancer Cell Lines in an Anticancer Drug Screen Panel, Planta Med 2002; 68: 297-301.
Hu K et al., the cytotoxicity of protoneodioscin (NSC-698789), a furostanol saponin from the rhizomes of *Dioscorea collettii* var. *hypoglauca*, against human cancer cells in vitro, Phytomedicine 9: 560-565, 2002.
Hu K et al., The Cytotoxicity of Methyl Protoneodioscin (NSC-698791) Against Human Cancer Cell Lines In Vitro: Anticancer Research 22: 1001-1006 (2002).
Hu K et al., Antineoplastic Agents; 1. Three Spirostanol Glycosides from Rhizomes of *Dioscorea Collettii* var. *hypoglauca*: Planta Medica 62 (1996) 573-575.
Inamdar AC et al., Comparison between Shatavar and *Asparagus* Spp.: Bioyigyanam 6: 27-35, 1980.
Inoue T et al., Steroidal Glycosides from *Allium Macleanii* and *A. Senescens*, and their inhibitory activity on tumour promoter-induced phospholipid Metabolism of Hela Cells: Phytochemistry vol. 40, No. 2, pp. 521-525 (1995).
Jin M et al., Cytotoxic Steroidal Saponins from *Polygonatum zanlanscianense*, J. Nat. Prod. , 67, 1992-1995. (2004).

Joussen AM et al., Nonsteroidal anti-inflammatory drugs prevent early diabetic retinopathy via TNF-α suppression: The FASAB Journal, Mar. 2002, vol. 16 pp. 438-440.
Derwent Publications Ltd., London, GB AN 2001-412294 & JP 2001 072597 A (Mercian) Corp; Mar. 21, 2001; (abstract).
Kostova I et al., Two new sulfated Furostanol Saponins from *Tribulus terrestris*: Z Naturforsch, 57c, pp. 33-38 (2002).
Li M et al., Synthesis of monomethylated dioscin derivatives and their antitumor activities: Carbohydrate Research 338 (2003) 117-121.
Liu M et al., Synthesis of (25R)-ruscogenin-1-yl β-D-xylopyranosyl-(1→3)-[β-D-glucopyranosyl-(1→2)]-β-D-fucopyranoside: Carbohydrate Research 329 (2000) 745-754.
Liu H et al., New Furostanol Glycosides from the Rhizomes of *Dioscorea Futschauensis* R. Kunth:Journal of Asian Natural Products Research 2003, vol. 5 (4) pp. 241-247.
Liu M et al., Diosgenin induces cell cycle arrest and apoptosis in human leukemia K562 cells with the disruption of $Ca^{2+}$ homeostasis: Cancer Chemother Pharmacol (2005) 55: 79-90.
Madar Z et al., Fenugreek (*Trigonella Foenumgraecum*) as a means of reducing postprandial glucose level in diabetic rats: Nutrition Reports International Jun. 1984, vol. 29, No. 6, pp. 1267-1273.
Mahato SB et al., Bacopasaponins E and F: two jujubogenin bisdesmosides from *Bacopa monniera*: Phytochemistry 53 (2000) 711-714.
Markine-Goriaynoff N. et al., The core 2 β-1, 6-*N*-acetylglucosaminyltransferase-M encoded by bovine herpesvirus 4 is not essential for virus replication despite contributing to post-translational modifications of structural proteins: Journal of General Virology (2004) 85, 355-367.
Melo PS et al., Cytotoxicity of phytosterol diosgenin and its derivatives in rat cultured hepatocytes and V79 fibroblasts: Human & Experimental Toxicology (2004) 23, 487-493.
Nakamura T et al., Interaction of Saponins with red blood cells as well as with the phosphatidylcholine liposomal membranes; J> Pharm Dyn. 2, 374-382 (1979).
Nian H et al., Protective effect of steroidal saponins from rhizome of *Anemarrhena asphodeloides* on ovarietomy-induced bone loss in rats; Acta Pharmacologica Sinica Jun. 2006: 27 (6) pp. 728-734.
Paseshnichenko VA et al., Isolation and Properties of Saponins from dioscorea deltoidea Rhizomes; Applied Biochem. Microbiol. 1975, II (1) p. 83-90.
Pawar R et al., Dammarane Triterpene Saponin from *Bacopa monniera* as the Superoxide inhibitor in Polymorphonuclear Cells; Planta Med 67 (2001) pp. 752-754.
Quan HJ et al., Preparations of heterospirostanols and their pharmacological activities; Eur. J Med. Chem 37 (2002) pp. 659-669.
Raju J et al., *Trigonella foenum graecum* (fenugreek) seed powder improves glucose homeostasis in alloxan diabetic rat tissues by reversing the altered glycolytic, gluconeogenic and lipogenic enzymes; Molecular and Cellular Biochemistry 224: 45-51, 2001.
Ribes G et al., Effects of Fenugreek Seeds on Endocrine Pancreatic Secretions in Dogs; Ann Nutr Metab 28: 37-43 (1984).
Shao Y et al., Anti-tumor activity of the crude saponins obtained from asparagus; Cancer Letters 104 (1996), 31-36.
Shao Y et al.,Steroidal Saponins from *Asparagus officinalis* and Their Cytotoxic Activity; Planta Medica 63 (1997) 258-262.
Sharma RD; Effect of Fenugreek Seeds and Leaves on Blood Glucose and Serum Insulin Responses in Human Subjects; Nutrition Research, vol. 6, pp. 1353-1364 (1986).
Sharma SC et al; Steroidal Saponins of *Asparagus adscendens*; Phytochemistry, vol. 21, No. 8, pp. 2075-2078 (1982).
Shimomura H et al; 26-O-Acylated Furostanol Saponins Pardarinoside A and B from the Bulbs of Lilium Pardarinum; Chem. Pharm. Bull. 36 (8) 3226-3229, 1988.
Sheilds et al Acute Multiple Sclerosis, characterized by extensive mononuclear phagocyte infiltration. Neurochem. res. 25, 1517-1520. (2000).
Singh SB et al., Furostanol Saponins from *Paris Polyphylla* Structures of Polyphyllin G and H; Phytochemistry, vol. 21, No. 8, pp. 2079-2082, 1982.

Sinha J et al; Bacopasaponin C: Critical Evaluation of Anti-Leishmanial Properties in Various Delivery Modes; Drug Delivery, 9: 55-62, 2002.

Sur P et al; *Trigonella Foenum graecum* (Fenugreek) Seed Extract as an Antineoplastic Agent; Phytotherapy Research, 15 257-259 (2001).

Spruce et al (2004) Intrinsic factors implicated in the sequence of diabetic neuropathy and foot ulceration: a potential role of core2 beta1, 6-N-acetylglucoseaminyltransferase (core2G1cNAcT-1) [core 2 transferase]. *Diabetic Medicine*, 21 (Suppl. 2), 1-35.

Vachalkova A et al., Potential carcinogenic and inhibitory activity of compounds isolatyed from *Lilium candidum* L; Neoplasma, 47, 5, 2000 pp. 313-318.

Vasileva.,. Composition and Biological Activity of Steroidal Glycosides from cell suspensions of *Dioscorea deltoidea* Wall. Prikl Biokhim Mikrobiol 1995, vol. 31 (2) pp. 238-242. English Abstract.

Vasileva, Isolation and properties of Saponins from Dioscorea deltoidea Wall Rhizomes. Prikl Biokhim Mikrob, 1975, II (1), p. 94-101—English Abstract.

Van Der Elst I and Datti A. $\beta$1,6 N-Acetylglucosaminyltransferase (core 2 G1cNAc-T) expression in normal rat tissues and different cell lines: evidence for complex mechanisms of regulation. Glycobiology vol. 8 No. 7 pp. 731-740, (1998).

Vasileva, Composition and Biological Activity of Steroid Glycosides from Cell Suspensions of *Discorea Deltoidea* Wall; Applied Biochemistry and Microbiology, vol. 31, No. 2 1995, pp. 206-209.

Vasyukova NI., Fungitoxic Properties of Steroid Saponins from *Dioscorea deltodea* Rhizomes; Applied Biochem Microbol. 1977, 13 (2) pp. 128-131.

Yu J et al., Progress in studies on chemical constituents and pharmacological effect of Trigonella foenum-graecum. Chinese traditional and Herbal Drugs, 34(12) 1146-1149 (2003).

Li C et al., Synthesis of diosgenyl $\alpha$-L rhamnopyranosyl-(1$\to$2)-[$\beta$-D-glucopyrampsyl-{1$\to$3)]$\beta$-D-glucopyranoside {gracillin} amd related saponins;Carbohydrate Research 306 (1998) p. 189-195.

Yu B et al., First Synthesis of a Bidesmosidic Triterpene Saponin by a Highly Efficient Procedure; J.AM.Chem.Soc. 1999, 121, pp. 12196-12197.

Zou CC et al., The synthesis of gracillin and dioscin: two typical representatives of spirostanol glycosides; Carbohydrate Research 338 (2003) pp. 721-727.

Battistini, L. et al; "CD8+ T cells from patients with acute multiple sclerosis display selective increase of adhesiveness in brain venules: a critical role for P-selectin glycoprotein ligand-1", *Blood*, vol. 101 No. 12, 4775-4780 (2003).

Ben-Mahmud, Bahaedin M., et al; "Tumor Necrosis Factor-$\alpha$ in Diabetic Plasma Increases the Activity of Core 2 GLcNAc-T and Adherence of Human Leukocytes to Retinal Endothelial Cells"; *Diabetes*, vol. 53, 2968-2976 (2004).

Brockhausen, I., et al; "Biosynthesis of O-Glycans in Leukocytes from Normal Donors and from Patients with Leukemia: Increase in O-Glycan Core 2 UDP-G1cNAc:Ga1$\beta$1-3Ga1NAc-R (GlcNAc to GalNAc) $\beta$1(1-6)-N-Acetylglucosaminyltransferase in Leukemic Cells"; *Cancer Research*; 51, 1257-1263 (1991).

Buerke, Michael, et al; "Sialyl Lewis[x]-Containing Oligosaccharide Attenuates Myocardial Reperfusion Injury in Cats"; *J. Clin. Invest.*; vol. 93, 1140-1148 (1994).

Beum, P. V. and Cheng, Pi-W.; "Biosynthesis and Function of $\beta$1,6 Branched Mucin-Type Glycans"; *The Molecular Immunology of Complex Carbohydrates-2* (2001).

Beum, P. V., et al; "Mucin biosynthesis: upregulation of core 2 $\beta$1,6 N-acetylglucosaminyltransferase by retinoic acid and Th2 cytokines in a human airway epithelial cell line"; *Am J. Physiol Lung Cell Mol Physiol.*; 288: L116-L124 (2005).

Beum, P. V., et al; "Mucin Biosynthesis Epidermal Growth Factor Downregulates Core 2 Enzymes in a Human Airway Adenocarcinoma Cell Line"; *Am. J. Respir. Cell Mol. Biol.*; vol. 29, 48-56 (2003).

Celie, J.W.A.M, et al; "Identification of L-Selectin Binding Heparan Sulfates Attached to Collagen Type XVIII"; *J. Biol Chem.*; 280(29); 26965-73; Epub (2005).

Davies, Michael J., et al; "The Expression of the Adhesion Molecules Icam-1, Vcam-1, Pecam, and E-Selectin in Human Atherosclerosis", *Journal of Pathology*, vol. 171: 223-239 (1993).

Dennis, James W.; "Glyco-Forum Section; Core 2 GlcNAc-Transferase and polylactosamine expression in O-glycans", *Glycobiology*; vol. 3, No. 2, pp. 91-96 (1993).

Dube, Danielle H. et al, "Glycans in Cancer and Inflammation—Potential for Therapeutics and Diagnostics", *Nature Reviews*, vol. 4, No. 6, 477-288 (2005).

Duan L-L. et al; "Regulation of Metastasis-Suppressive Gene Nm23-H1 on Glycosy-transferases Involved in the Synthesis of Sialy Lewis Antigens"; *J. Cell. Biochem.*; 94:1248-1257 (2005).

Fox, R.I., et al; "A Novel Cell Surface Antigen (T305) Found in Increased Fequency on Acute Leukemia Cells and in Autommune Disease States"; *J. Immunol.* vol. 131, No. 2, 761-767 (1983).

Foxall, C. et al; "The Three Members of the Selectin Receptor Family Recognize a Common Carbohydrate Epitope, the Sialyl Lewis[x] Oligosaccharide"; *J. Cell Biol.*; vol. 117, 895-902 (1992).

Fugang P. et al.; "Post Translational Modifications of Recombinant P-selectin Glycoprotein Ligand-1 Required for Binding to P and E-selectin"; *J. Biol. Chem.*; vol. 271, No. 6, 3255-3264 (1996).

Fujita, M et al; "Pulmonary hypertension in TNF-$\alpha$-overexpressing mice is associated with decreased VEGF gene expression"; *J. Applied Physiol*; vol. 93, 2162-2170 (2002).

Goss, P. E. et al; "Inhibitors of Carbohydrate Processing: A New Class of Anticancer Agents[1,2]"; *Clin. Cancer Res.*; vol. 1, 935-944 (1995).

Maaheimo,Hannu et al, "Synthesis of a divalent sialyl Lewis x O-glycan, a potent inhibitor of lymphocyte-endothelium adhesion"; *Eur. J. Biochem*; 234, 616-625 (1995).

Hiraoka, N. et al; "Core 2 Branching $\beta$1,6-N-Acetylglucosaminyltransferase and High Endothelial Venule-restricted Sulfotransferase Collaboratively Control Lymphocyte Homing"; *J. Biol Chem.*; vol. 279, No. 4, 3058-3067 (2004).

Ke, Hu et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).

Kumar, A. et al; "Recombinant Soluble Form of PSGL-1 Accelerates Thrombolysis and Prevents reocclusion in a Porcine Model"; *Circulation*; 99, 1363-1369 (1999).

Jain, Rakesh K. et al, "Inhibition of L- and P-selectin by a rationally synthesized novel core 2-like branched structure containing GalNAc-Lewis[x] and Neu5Ac$\alpha$2-3Gal$\beta$1-3GalNAc sequences"; *Glycobiology*, vol. 8, No. 7; 707-717 (1998).

Jones, Steven P., "A Bittersweet Modification O-GlcNAc and Cardiac Dysfunction"; *Circ Res.*; 96; 925-926 (2005).

Kamisako, Toshinori et al, "Regulation of biliary cholesterol secretion is associated with abcg5 and abcg8 expressions in the rats: effects of diosgenin and ethinyl estradiol", *Hepatology Research* 26; 348-352 (2003).

Lewis, M.J. and D 'Cruz D.; "Adhesion molecules, mycophenolate mofetil and systemic lupus erythematosus"; *Lupus*, 14, 17-26 (2005).

Martininez, M et al; "Regulation of PSGL-1 Interactions with L-selectin, P-selectin, and E-selectin"; *J. Biol. Chem.*, vol. 280, No. 7, 5378-5390 (2005.).

Merzaban, Jasmeen S. et al.; "An Alternate Core 2 $\beta$,6-N-Acetylglucosaminyltransferase Selectively Contributes to P-Selectin Ligand Formation in Activated CD8 T Cells[1]"; *The Journal of Immunology*, 174: 4051-4059 (2005).

Morin, M.J. and Bernacki, R.J; "Biochemical Effects and Therapeutic Potential of Tunicamycin in Murine L1210 Leukemia"; *Cancer Res.* 43, 1669-1674 (1983).

Nakamura, M et al.; "Single Glycosyltransferase, Core 2$\beta$1-6-N-acetylglucosaminyltransferase, Regulates Cell Surface Sialy-Le[x] Expression Level in Human Pre-B Lymphocytic Leukemia Cell Line KM3 Treated with Phorbolester"; *J. Biol. Chem.*; 273, No. 41; 26779-26789 (1998).

Narumi, S. et al; "Tissue-Specific Induction of E-Selectin in Glomeruli is Augmented following Diabetes mellitus"; *Nephron*; 89, 161-171 (2000).

Okada, S. et al; "Intercellular Adhesion Molecule-1-Deficient Mice are Resistant Against Renal Injury After Induction of Diabetes"; *Diabetes*; 52:2586-2593 (2003).

Piccio L. et al; "Molecular Mechanisms Involved in Lymphocyte Recruitment in Inflamed Brain Microvessels: Critical Roles for P-Selectin Glycoprotein Ligand-1 and Heterotrimeric $G_i$-Linked Receptors[1]"; *J. Immunol.*; 168: 1940-1949 (2002).

Ravnskov, U.; "Is atherosclerosis caused by high cholesterol?", *QJ Med*; 95, 397-403 (2002).

Ross, Russell; "Atherosclerosis—An Inflammatory Disease", *The New England Journal of Medicine*, vol. 340, 2, 115-126 (1999).

Simmons, Rex D. and Brenda A. Cattle; "Sialyl Ligands facilitate lymphocyte accumulation during inflammation of the central nervous system", *Journal of Neuroimmunology*, 41; 123-130 (1992).

Steinberg, D.; "Atherogenesis in perspective: Hypercholesterolemia and inflammation as partners in crime"; *Nature Medicine*; vol. 8, No. 11; 1211-1217 (2002).

Steinman, Lawrence; "Blocking Adhesion Molecules as Therapy for Multiple Sclerosis: Natalizumab"; *Nature Reviews: Drug Discovery*, vol. 4, 510-518 (2005).

Baek, Suk Hwan, et al, "Inactivation of Human Pleural Fluid Phospholipase $A_2$ by Dioscin"; *Arch. Pharm. Res.*; vol. 17, No. 4, 218-222 (1994).

Ulbrich, Holger, et al; "Leukocyte and endothelial cell adhesion molecules as targets for therapeutic interventions in inflammatory disease"; *Trends in Pharmacological Sciences*, vol. 24, No. 12; 640-647 (2003).

Williams, D. et al; "Mucin Synthesis II. Substrate Specificity and Product Identification Studies on Canine Submaxillary Gland UDP-GlcNAc:Galβ1-3GalNAc(GlcNAc—GalNAc) β6-N-acetylglucosaminyltransferase"; *J. Biol. Chem.*; 255, No. 23; 1253-1261 (1980).

Yanagihara, K., et al; "Lipopolysaccharide Induces Mucus Cell Metaplasia in Mouse Lung"; *Am. J. Respir. Cell Mol. Biol.*; 24, 66-73 (2001).

Yu, Jing et al, "Progress in studies on chemical constituents and pharmacological effect of *Trigonella foenum-graecum*"; *Chinese Traditional and Herbal Drugs*, vol. 34, (12) 1146-1149 (2003).

Zak, I., et al; "Selectin Glycoprotein Ligands"; *Acta Biochemica Polonica*; vol. 47, No. 2; 393-412 (2000).

Davies, Michael J., et al; "The Expression of the Adhesion Molecules Icam-1, Vcam-1, Pecam, and E-Selectin in Human Atherosclerosis", *Journal of Pathology*, vol. 171: 223-239 (1993).

Ke, Hu et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).

Mimaki, Y., et al; "Steroidal Saponins from *Hosta Longipes* and Their Inhibitory Activity on Tumour Promoter-Induced Phospholipid Metabolism of HeLa Cells"; *Phytochemistry*, vol. 42, No. 4, pp. 1065-1070 (1996).

Australian Office Action; Examiner's first report on Patent Application No. 2004305302, dated Aug. 27, 2009 (2 pgs).

Chinese Office Action; Second Office Action on Patent Application No. 200480041735.3, dated Dec. 22, 2004, pp. 1-5.

Chinese Office Action; First Office Action on Patent Application No. 200680032400.4, dated Jul. 6, 2006, pp. 1-5.

Chinese Office Action; First Office Action on Patent Application No. 200680031670.3, dated Jul. 6, 2006, pp. 1-5.

Chinese Office Action; First Office Action on Patent Application No. 200480041735.3, dated Dec. 22, 2004, pp. 1-4.

British Search Report; Application No. GB0513888.8, Date of Search Nov. 1, 2005 (3 pgs).

British Search Report; Application No. GB0513881.3, Date of Search Nov. 1, 2005 (3 pgs).

Mexican Office Action; Application No. PA/a/2006/007087, dated Nov. 19, 2009 (2 pgs).

Xu, X., et al; "Studies on saponin from seeds of *Trigonella foenum-graecum* (II) Isolation and structural elucidation for a new saponin A and its secondary glucosides"; *Chinese Traditional and Herbal Drugs*; p. 679 (2003).

Friedman, M., et al; "Effect of feeding solanidine, solasodine and tomatidine to non-pregnant and pregnant mice"; *Food and Chemical Toxicology*, vol. 41, pp. 61-71 (2003).

Skulina, C., et al; "Multiple sclerosis: Brain-infiltrating CD8[+] T cells persist as clonal expansions in the cerebrospinal fluid and blood"; *PNAS*; vol. 101, No. 8; pp. 2428-2433 (2004).

Ley, K., et al; "Selectins in T-Cell Recruitment to Non-Lymphoid Tissues and Sites of Inflammation"; *Nature Reviews Immunology*; vol. 4, pp. 1-11 (2004).

Gober, M.; "Models of Acute Inflammation in the Ear". In "Inflammation Protocols" *Methods in Molecular Biology*, vol. 225, pp. 1129-1137 (2003).

Sauvaire, Y., et al; "Implication of Steroid Saponins and Sapogenins in the Hypocholesterolemic Effect of Fenugreek"; *Lipids*, vol. 26(3); pp. 191-197 (1991).

Yang, D.-J.et al; "Simultaneous Determination of Furostanol and Spirostanol Glycosides in Taiwanese Yam (*Dioscorea spp.*) Cultivars by High Performance Liquid Chromatography"; *Journal of Food and Drug Analysis*; vol. II, No. 4, pp. 271-276 (2003).

Hoff, P.M., et al; "Comparison of Oral Capecitabine Versus Intravenous Fluorouracil Plus Leucovorin as First-Line Treatment in 605 Patients with Metastatic Colorectal Cancer: Results of a Randomized Phase III Study"; *Journal of Clinical Oncology*; vol. 19, No. 8; pp. 2282-2292 (2001).

Milgate, J., et al; "The Nutritional & Biological Significance of Saponins"; *Nutritional Research*, vol. 15, No. 8; pp. 1223-1249 (1995).

Guo, Z., et al; "Microwave-assisted extraction of effective constituents from a Chinese herbal medicine Radix puerariae"; *Analytica Chimica Acta*; vol. 436; pp. 41-47 (2001).

Akhov, L.S., et al; Biological activity of Deltoside from *Allium Nutans L.*, Saponins in Food, Feedstuffs and Medicinal Plants Chapter 23, pp. 227-231 (2000).

Chen, C., et al; Yunnan Zhiwu Yanjiu, vol. 9 (4) 495-502 (1987).

Garai, S. ,et al; Bacopasaponin D-A Pseudojujubogenin Glycoside from *Bacopa monniera*; Phytochemistry, vol. 43, No. 2, pp. 447-449 (1996).

Hosny, M., et al; Balanitoside, A furostanol Glycoside, and 6-Methyl-Diosgenin from *Balanites aegyptiaca*, Phytochemistry, vol. 31, No. 10 pp. 3565-3569 (1992).

Hostettmann, K., et al; Saponins (Chemistry and Pharmacology of Natural Products), Cambridge University Press, Cambridge, UK, Extract (1995).

Kim, H., et al; Chemical Synthesis of 15-Ketosterols and their Inhibitions of Cholesteryl Ester Transfer Protein: Bioorganic & Medicinal Chemistry, vol. 3, No. 4, pp. 367-374 (1995).

Mimaki, Y., et al; Steroidal Saponins from the Bulbs of *Lilium BrownII*: Phytochemistry, vol. 29, No. 7, pp. 2267-2271 (1990).

Miyahara, K., et al; Conversion of Steroid Saponins to the Corresponding Pregnane Glycosides: Chem. Pharm. Bull. 20 (11) 2506-2510 (1972).

Mori, K., et al; Synthesis of some analogues of Blattellastanoside A, the Steroidal Aggregation Pheromone of the German Cockroach: Bioorganic & Medicinal Chemistry, vol. 4, No. 3, pp. 401-408 (1996).

Ori, K., et al; Norlanostane and Lanostane Glycosides from the Bulbs of *Chionodoxa luciliae* and Their Cytotoxic Activity; Chem. Pharm. Bull 51 (1) 92-95 (2003).

Takahashi, T., et al; Increased Spontaneous Adherence of Neutrophils from Type 2 Diabetic Patients with Overt Proteinuria; Diabetes Care, vol. 23, No. 3 pp. 417-418 (2000).

Vasil'eva, et al; Steroid Glycosides from Suspension Cultures of *Dioscorea Deltoidea* Cells and Their Biological Activity In "Saponins used in Traditional and Modern Medicine" Eds Waller and Yamasaki, Plenum Press New York (1996).

Yamishita, T., et al; Structures of three new steroidal alkaloid glycosidesm solaverines I, II and III from Solanum Toxicarium and S. Verbascifolium; Chem. Pharm. Bull. 38 (3) pp. 827-829 (1990).

Yang, X., et al; The effect of TNF-α on glycosylation pathways in bovine synoviocytes; Biochem. Cell Biol. 82 pp. 559-568 (2004).

\* cited by examiner

CORE 2 GLCNAC-T INHIBITORS III

The present invention relates to the use of known and novel compounds as pharmaceutical actives against diseases susceptible to treatment by modulation, eg. inhibition, of the enzyme Core 2 GlcNAc-transferase (EC 2.4.1.102), also known as UDP-GlcNAc:Galβ1,3GalNAc—R (GlcNAc to GalNAc) β-1,6-N-acetylglucosaminyl transferase (core 2 β-1,6 N-acetylaminotransferase, hereinafter referred to as Core 2 GlcNAc-T.

Inhibitors of Core 2 GlcNAc-T, and the present compounds in particular, have application in therapy for diseases in which core 2 GlcNAc-T is implicated and especially those in which the enzyme activity is raised relative to the normal level in the tissue type concerned, or those conditions in which it is advantageous to lower the activity of core 2 GlcNAc-T for example to its normal level or below. Examples of such conditions are inflammatory diseases such as atherosclerosis and multiple sclerosis, diabetes, cancer and its metastasis.

Inhibitors of Core 2 GlcNAc-T are known but none are in clinical development as isolated actives for pharmaceutical use. Examples of known compounds are disclosed in WO0187548, Kuhns (15), Hindsgaul (45) and Toki (46).

Applicant's co-pending application WO05060977 (incorporated herein by reference) discloses known and novel steroidal glycosides that have therapeutic use as Core GlcNAc-T inhibitors, discusses the basis for use of such inhibitors in therapy and discloses published documents detailing the basis for Core 2 GlcNAc-T involvement in a number of diseases. The present application discloses further steroidal glycoside compounds that are suitable for use in therapy for diseases in which Core 2 GlcNAc-T is implicated and additional such conditions in which such compounds have a therapeutic use.

Some of the presently disclosed steroidal glycosides have been tested previously in a limited number of disease paradigms. For example in protection against gastric mucosal lesions in rats (80), in mouse ear edema tests for anti inflammatory activity (79), in treatment of dementia (U.S. Pat. No. 6,593,301) as "immuno-modulators" and spermatogenesis and ovulation stimulators (74) and as adjuvants (75). Compounds of the invention have also been used in cytotoxicity assays (e.g. 36, 40, 72), however cytotoxic concentrations are several orders of magnitude higher than those currently disclosed for inhibition of Core 2 GlcNAc-T activity. None of the aforementioned publications discloses that certain steroidal glycosides are inhibitors of Core 2 GlcNAc-T.

Certain plant sterol compounds, some of which are used as dietary supplements, impede the uptake of cholesterol from the gut and consequently lower plasma LDL cholesterol. However these compounds are generally used in doses of several grams per day and are not known to be inhibitors of Core 2 GlcNAc-T.

In a first aspect the present invention is provided a method of treating a subject in need of therapy for a condition involving detrimental activity of the enzyme core 2 GlcNAc-T, particularly raised activity, comprising administration of a therapeutically effective amount of an inhibitor of core 2 GlcNAc-T of formula I to a patient in need thereof

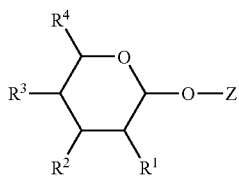

I wherein
$R^1$ is H, —OH, $C_{1-6}$ alkoxy, —$NR^5R^6$, or Sac 1;
$R^2$ is H, —OH, $C_{1-6}$ alkoxy or Sac 2;
$R^3$ is H, —OH, $C_{1-6}$ alkoxy or Sac 3;
$R^4$ is H, $C_{1-6}$ alkyl, $C_{1-6}$ hydroxyalkyl or $C_{1-6}$-alkoxy-$C_{1-6}$-alkyl;
$R^5$ is H, $C_{1-6}$ alkyl or $C_{1-6}$ acyl;
$R^6$ is H, $C_{1-6}$ alkyl or $C_{1-6}$ acyl;
Sac 1, Sac 2 and Sac 3 are independently selected saccharide moieties attached to the ring through an oxygen; and
Z is a steroid moiety;
or a pharmaceutically acceptable salt, ether, ester or tautomeric form thereof.

When one of $R^1$ to $R^3$ is a saccharide moiety, the ring of formula I is designated ring A.

$R^1$ is H, —OH, $C_{1-6}$ alkoxy, —$NR^5R^6$, or Sac 1; preferably $R^1$ is H, —OH, or Sac 1; more preferably $R^1$ is Sac 1;
$R^2$ is H, —OH, $C_{1-6}$ alkoxy or Sac 2; preferably $R^2$ is H, —OH or Sac 2; more preferably $R^2$ is —OH;
$R^3$ is H, —OH, $C_{1-6}$ alkoxy or Sac 3; preferably $R^3$ is H, —OH or Sac 3; more preferably $R^3$ is Sac 3;
$R^4$ is H, $C_{1-6}$ alkyl, $C_{1-6}$ hydroxyalkyl or $C_{1-6}$-alkoxy-$C_{1-6}$-alkyl; preferably $R^4$ is H, $C_{1-6}$ alkyl or $C_{1-6}$ hydroxyalkyl; more preferably $R^4$ is H, —$CH_2OH$ or —$CH_3$; more preferably still $R^4$ is —$CH_2OH$; more preferably still $R^4$ is —$CH_2OH$ and the resultant moiety is a glucose or galactose moiety; most preferably $R^4$ is —$CH_2OH$ and the resultant moiety is a glucose moiety;
$R^5$ is H, $C_{1-6}$ alkyl or $C_{1-6}$ acyl; preferably $R^5$ is H or $C_{1-6}$ alkyl; more preferably $R^5$ is H or —$CH_3$; most preferably $R^5$ is H;
$R^6$ is H, $C_{1-6}$ alkyl or $C_{1-6}$ acyl; preferably $R^6$ is H —$CH_3$ or —$COCH_3$; most preferably $R^6$ is —$COCH_3$; and
Sac 1, Sac 2 and Sac 3 are saccharide moieties attached to the ring through an oxygen; preferably Sac 1 Sac 2 and Sac 3 are independently selected from monosaccharide moieties and disaccharide moieties; preferably they are monosaccharide moieties; more preferably Sac 1 Sac 2 and Sac 3 are independently selected from a tetrose a pentose and a hexose. Preferably Sac 1 is selected from a pentose, a deoxy-aldohexose and an aldohexose; more preferably Sac 1 is selected from arabinose, xylose, glucose, mannose, galactose, and a deoxy-aldohexose; more preferably Sac 1 is selected from arabinose, xylose, glucose, mannose, galactose, and a 6-deoxyaldohexose; more preferably Sac 1 is selected from. glucose, galactose, arabinose, xylose and rhamnose; most preferably it is rhamnose;

Preferably Sac 2 is selected from a pentose, a deoxy-aldohexose and an aldohexose; more preferably Sac 2 is selected from arabinose, xylose, glucose, mannose, galactose, and a deoxyaldohexose; more preferably Sac 2 is selected from arabinose, xylose, glucose, mannose, galactose, and a 6-deoxyaldohexose; more preferably Sac 2 is selected from. glucose, galactose, arabinose, xylose and rhamnose;

Preferably Sac 3 is selected from a pentose, a deoxy aldohexose and an aldohexose; arabinose, xylose, quinovose rhamnose or an aldohexose, more preferably Sac 3 is selected from arabinose, xylose, quinovose, rhamnose, mannose, glucose and galactose, most preferably Sac 3 is rhamnose or glucose;

Z is a steroid moiety;
or a pharmaceutically acceptable salt, ether, ester or tautomeric form thereof.

The present inventors have determined that because of its involvement in the synthesis of particular branched oligosaccharides, Core 2 GlcNAc-T modulation, particularly inhibition, may be used to treat inter alia, vascular diseases, (including complications of diabetes), autoimmune and inflammatory conditions. Particular conditions subject to treatment by the present invention are myopathy, retinopathy, nephropathy, atherosclerosis, asthma, rheumatoid arthritis, inflammatory bowel disease, transplant rejection, ischemia reperfusion injury (e.g. stroke, myocardial ischemia, intestinal reperfusion e.g. after hemorrhagic shock,), restenosis, ileitis, Crohn's disease, thrombosis, cholitis including for example ulcerative cholitis), lupus, frost bite injury, acute leukocyte mediated lung injury (eg adult respiratory distress syndrome), traumatic shock, septic shock, nephritis, psoriasis, cholicytitis, cirrhosis, diverticulitis, fulminant hepatitis, gastritis, gastric and duodenal ulcers, hepatorenal syndrome, irritable bowel syndrome, jaundice, pancreatitis, ulcerative cholitis, human granulocyte ehlichiosis, Wiskott-Aldrich syndrome T-cell activation, AIDS, infection with viruses, bacteria, protozoa and parasites adapted to use particular core 2 derived glycans and cancer. Cancer metastasis is a particularly treatable by the present method. (see references 1-15, 47-57, 67-70, 81 and 82 for evidence of the association of Core 2 GlcNAc-T or glycans formed by Core 2 GlcNAc-T with these diseases).

Cancers may include, for example, leukemias, lymphomas, melanomas, adenomas, sarcomas, and carcinomas of solid tissues; particularly cancers include prostate, testicular, mammary, pancreatic, cervical, uterine, kidney, lung, rectum, breast, gastric, thyroid, neck, cervix, bowel, salivary gland, bile duct, pelvis, mediastinum, urethra, bronchogenic, bladder, esophagus, colon, small intestine and sarcomas (eg. Kaposi's sarcoma) and adenomatous polyps. Particularly susceptible cancers for treatment are oral cavity carcinomas, pulmonary cancers such as pulmonary adenocarcinoma, colorectal cancer, bladder carcinoma, liver tumours, stomach tumours colon tumours, prostate cancer, testicular tumour, mammary cancer, lung tumours oral cavity carcinomas. Particular application is found in cancer or its metastasis where Core 2 GlcNAc-T activity is raised.

Preferably the compound of the formula I is a compound of the formula II

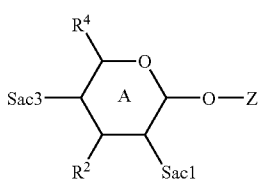

wherein
$R^2$ is H, —OH, or $C_{1-6}$ alkoxy; more preferably $R^2$ is H or —OH; $R^4$ is as defined above; and Sac 1 and Sac 3 are saccharide moieties.

More preferred compounds are those of the formula II wherein $R^4$ is H, —CH$_2$OH or —CH$_3$;

Particularly preferred still are those compounds wherein: $R_4$ is —CH$_2$OH;

More preferred still are those compounds wherein: $R_4$ is —CH$_2$OH and the moiety A is a glucose moiety;

In a preferred combination Ring A is either glucose or galactose; preferably glucose; Sac 1 is selected from glucose, galactose, arabinose, xylose and rhamnose and is preferably rhamnose; Sac 3 is selected from glucose, galactose, arabinose, xylose and rhamnose; preferably glucose.

Most preferred are compounds of the formula I which are of the formula III:

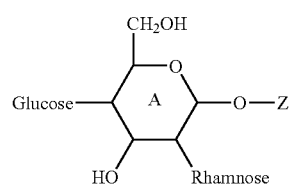

Wherein the ring A is a glucose moiety, and which formula may be written

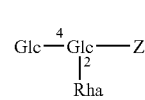

In which Rha represents rhamnose, Glc represents glucose and 2 and 4 are the positions of ring A to which the saccharides are attached.

Most preferred are compounds which are 6-deoxy-α-L-mannopyranosyl-(1→2)-O-[β-D-glucopyrancsyl-(1→4)]-β-D-glucopyranosides of steroid moieties Z.

Alternatively compounds of the formula I are compounds of the formula IV:

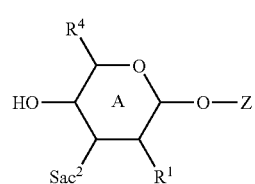

wherein:
wherein $R^1$ is H, —OH, $C_{1-6}$ alkoxy, —NR$^5$R$^6$, or Sac 1; preferably $R^1$ is —OH, $C_{1-6}$ alkoxy or —NR$^5$R$^6$; more preferably $R^1$ is —NR$^5$R$^6$ $R^3$ is H, —OH or $C_{1-6}$ alkoxy; preferably $R^3$ is H or —OH $R^4$ and Sac 2 are as defined above;

Preferred compounds of the formula Iv are compounds in which:
$R^1$ is —OH, $C_{1-6}$ alkoxy or NR$^5$R$^6$; $R^4$ is H, $C_{1-6}$ alkyl or $C_{1-6}$ hydroxyalkyl; Sac 2 is glucose, galactose, arabinose, xylose and rhamnose More preferred compounds of the formula IV are those in which: $R^1$ is —NH—$C_{1-6}$-acyl; $R^4$ is —CH$_3$ or —CH$_2$OH; Most preferred are the compounds of the formula IV which are of the formula Galβ1→3(6-deoxy)GalNAcα-Z The term "steroid moiety" denotes a moiety comprising a tetracyclic ring system shown as formula V:

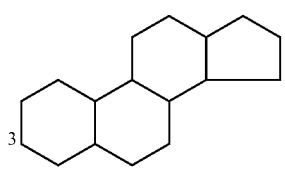

Typically the steroid moiety ring system is modified, for example by the addition of one or more further rings and/or one or more double bonds and/or one or more substituents. Typically the saccharide ring A is attached to the steroid moiety at the 3 position. The steroid moiety may for example have the ring system of cholestane, pregnane, androstane, estrane, cholesterol, cholane, progestin, a mineralocorticoid, such as dehydroepiandrosterone or its 7-keto or 7-hydroxy analogue or a bile acid.

In one preferred embodiment the steroid moiety is that of a steroid that is in itself beneficial or neutral. By neutral is meant that the steroid ring is that which is considered suitable, whether as approved eg. by the FDA or as GRAS, for use in a human or animal. By beneficial is meant that the steroid has effects of benefit to the human or animal if it were administered separately.

The steroid moiety Z may for example be that of a steroidal sapogenin derivable from natural sources (for example plant sources) or a steroidal moiety which is itself derivable from such steroidal sapogenins by chemical modification. The sapogenin may for example be that of a furostanol glycoside, a spirostanol glycoside (including those with nitrogen and oxygen containing rings) a damarane glycoside or other steroidal saponin. The steroid moiety Z for example may be a steroid moiety of the formula VI

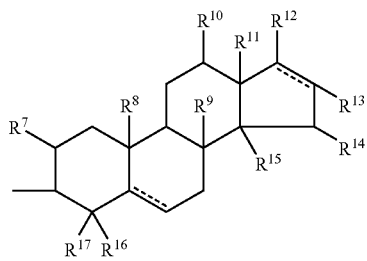

VI

Groups or rings that may be incorporated into the steroid core V or VI are selected from those set out in formulae VI a to VI e wherein the dotted lines represent the relevant rings of the steroid core.

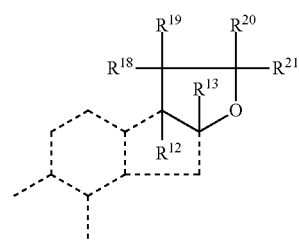

VI a

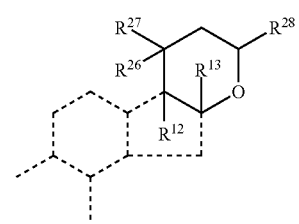

VI b

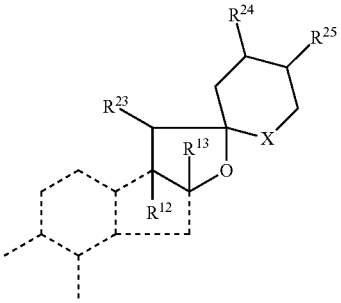

VI c

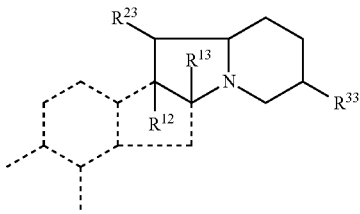

VI d

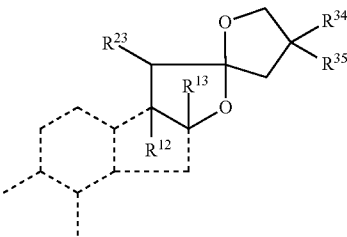

VI e wherein:

$R^7$, $R^{14}$, $R^{22}$ and $R^{24}$ are independently selected from H and —OH;

$R^8$, $R^{18}$, $R^{23}$, $R^{27}$, $R^{29}$ and $R^{33}$ are independently selected from $C_{1-6}$ alkyl; preferably $R^8$, $R^{18}$, $R^{23}$, $R^{27}$, $R^{29}$ and $R^{33}$ are —$CH_3$;

$R^9$, $R^{11}$ and $R^{16}$ are independently selected from H and $C_{1-6}$ alkyl; preferably $R^9$, $R^{11}$ and $R^{16}$ are independently selected from H and —$CH_3$;

$R^{10}$ is H or —OH or the H normally also present is absent and $R^{10}$ is =O;

$R^{12}$ is H, —OH or $C_{1-6}$ acyl or a group selected from VII a or VII b; preferably $R^{12}$ is H, —OH or acetyl or a group selected from VII a or VII b;

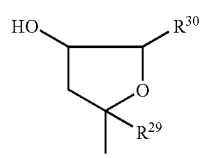

VII a

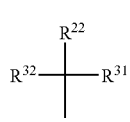

VII b $R^{13}$ is H.

$R^{15}$ is H, $C_{1-6}$ alkyl or —OH or $R^{13}$ and $R^{15}$ taken together form a —$CH_2$—$CH_2$— group; preferably $R^{15}$ is H, —OH or —$CH_3$ or $R^{13}$ and $R^{15}$ taken together form a —$CH_2$—$CH_2$— group;

$R^{17}$ is H, $C_{1-6}$ alkyl or $C_{1-6}$ hydroxyalkyl; preferably $R^{17}$ is H, —$CH_2OH$, or —$CH_3$.

$R^{19}$ is H or —OH.

$R^{20}$ is H, —OH or $C_{1-6}$ alkoxy or $R^{19}$ and $R^{20}$ taken together represent the second bond of a double bond joining adjacent carbon atoms; preferably $R^{20}$ is H, —OH or —$OCH_3$ or $R^{19}$ and $R^{20}$ taken together represent the second bond of a double bond joining adjacent carbon atoms;

$R^{21}$ is $C_{1-6}$ alkyl, $C_{2-6}$ alkenyl, $C_{2-6}$ alkynyl or a $C_{1-6}$ alkyl or $C_{2-6}$ alkenyl group substituted by one or more groups selected from the group consisting of —OH, $C_{1-6}$ alkoxy and Sac 4; preferably $R^{21}$ is $C_{2-6}$ alkenyl, or a $C_{1-6}$alkyl or $C_{2-6}$ alkenyl group substituted by one or more groups selected from the group consisting of —OH, $C_{1-6}$ alkoxy and Sac 4; more preferably $R^{21}$ is $C_{2-6}$ alkenyl or a $C_{1-6}$ alkyl or $C_{2-6}$ alkenyl group substituted by one or more groups selected from the group consisting of —OH, —$OCH_3$ and Sac 4; most preferably $R^{21}$ is selected from the group consisting of 3-methylenbutyl substituted at the 4-position by Sac4, 4-hydroxy-3-methybutanyl, 3-methyl but-2-eneyl, 2-methyl-prop-2-enyl, 3-methylbutanyl substituted at the 4-position by Sac4, 1-hydroxy-3-methylbutanyl substituted at the 4-position by Sac4 or 1-methoxy-3-methylbutanyl substituted at the 4-position by Sac4, $R^{25}$ is $C_{1-6}$ alkyl, $C_{1-6}$ hydroxyalkyl or =$CH_2$; preferably $R^{25}$ is —$CH_3$, —$CH_2OH$ or =$CH_2$;

$R^{26}$ is —OH;

$R^{28}$ is $C_{1-6}$ alkyl, $C_{2-6}$ alkenyl or $C_{2-6}$ alkynyl; preferably $R^{28}$ is $C_{2-6}$ alkenyl; most preferably it is 2-methylprop-2-enyl $R^{30}$ is $C_{1-6}$ hydroxyalkyl;

$R^{31}$ is $C_{1-6}$ alkyl, $C_{1-6}$ hydroxyalkyl or $C_{1-6}$ alkyl substituted by Sac 5; preferably $R^{31}$ is $C_{1-6}$ alkyl or $C_{1-6}$ alkyl substituted by Sac 5; more preferably $R^{31}$ is —$CH_3$ or —$CH_2$-Sac 5.

$R^{32}$ is $C_{1-8}$ alkyl, $C_{2-8}$ alkenyl or $C_{2-8}$ alkynyl; preferably $R^{32}$ is $C_{1-8}$ alkyl or $C_{2-8}$ alkenyl; more preferably 3-ethyl-4-methyl-pentanyl or 5-methyl-hex -4-enyl;

$R^{34}$ is $C_{1-6}$ hydroxyalkyl or $C_{1-6}$ alkyl substituted by Sac 6; preferably $R^{34}$ is $C_{1-6}$ alkyl substituted by Sac 6; more preferably $R^{34}$ is —$CH_2$-Sac 6;

$R^{35}$ is $C_{1-6}$ alkyl; preferably $R^{35}$ is —$CH_3$; and

Sac 4, Sac 5 and Sac 6 are independently selected saccharides; preferably Sac 4, Sac5 and Sac 6 are independently selected monosaccharides; more preferably they are independently selected a hexose, a pentose or a tetrose; more preferably still they are independently selected from glucose, galactose, quinovose, fucose, arabinose and xylose, most preferably they are glucose.

----- Represents a bond that is either double or single; and

X is either O or NH; preferably X is O.

Preferred steroid moieties Z that do not incorporate further groups VI(a) to VI(e) are those in which $R^9$ is $C_{1-6}$ alkyl; $R^{11}$ is H; and $R^{12}$ is VII(a); preferably $R^9$ is $C_{1-6}$ alkyl; $R^{11}$ is H; $R^{12}$ is VII(a); $R^{15}$ is $C_{1-6}$ alkyl and $R^{10}$ is H or —OH; more preferably $R^9$ is $C_{1-6}$ alkyl; $R^{11}$ is H; $R^{12}$ is VII(a); $R^{15}$ is $C_{1-6}$ alkyl; $R^{10}$ is H or —OH, $R^{16}$ is $C_{1-6}$ alkyl and $R^{17}$ is $C_{1-6}$ alkyl or $C_{1-6}$ hydroxyalkyl.

Further preferred steroid moieties Z that do not incorporate further groups VI(a) to VI(e) are those in which $R^9$ is $C_{1-6}$ alkyl; $R^{11}$ is H; and $R^{12}$ is VIII(b); preferably $R^9$ is $C_{1-6}$ alkyl; $R^{11}$ is H; $R^{12}$ is VII(b) and $R^{16}$, $R^{17}$ and $R^{15}$ are $C_{1-6}$ alkyl; more preferably $R^9$ is $C_{1-6}$ alkyl; $R^{11}$ is H; $R^{12}$ is VII(b) and $R^{16}$, $R^{17}$ and $R^{15}$ are $C_{1-6}$ alkyl and $R^{10}$ is H or —OH.

Further preferred steroid moieties Z that do not incorporate further groups VI(a) to VI(e) are those in which $R^9$ is H; $R^{11}$ is $C_{1-6}$ alkyl; and $R^{12}$ is $C_{1-6}$ acyl; preferably $R^9$ is H; $R^{11}$ is $C_{1-6}$ alkyl; $R^{12}$ is $C_{1-6}$ acyl; $R^{16}$ and $R^{17}$ are H $R^{15}$ is H or —OH.

Further preferred steroid moieties Z that do not incorporate further groups VI(a) to VI(e) are those in which $R^9$ is H; $R^{11}$ is $C_{1-6}$ alkyl; and $R^{12}$ is VII b; preferably $R^9$ is H; $R^{11}$ is $C_{1-6}$ alkyl; $R^{12}$ is VIIb; $R^{16}$ and $R^{17}$ are H; and $R^{15}$ is H or —OH;

More preferred are steroid moieties Z selected from groups V which incorporate further groups VI a, VI c, VI d and VI e.

Preferred steroid moieties Z incorporating further groups VI a are those in which $R^9$ is H, $R^{11}$ is $C_{1-6}$ alkyl; $R^{12}$ is H or —OH; $R^{16}$ and $R^{17}$ are H and $R^{21}$ is $C_{2-6}$ alkenyl or a $C_{1-6}$ alkyl or $C_{2-6}$ alkenyl group substituted by one or more groups selected from the group consisting of —OH, —$OCH_3$ and Sac 4; preferably $R^8$ is $C_{1-6}$ alkyl and $R^9$ is H and $R^{11}$ is $C_{1-6}$ alkyl; $R^{12}$ is H or —OH; $R^{16}$ and $R^{17}$ are H and $R^{21}$ is 3-methylenbutyl substituted at the 4-position by Sac 4, 3-methyl but-2-eneyl, 2-methyl-prop-2-enyl, 4-hydroxy-3-methylbutanyl, 3-methylbutanyl substituted at the 4-position by Sac4, 1-hydroxy-3-methylbutanyl substituted at the 4-position by Sac4 or 1-methoxy-3-methylbutanyl substituted at the 4-position by Sac 4;

Alternatively, steroid moieties Z incorporating further groups VI a are those in which $R^9$ is $C_{1-6}$ alkyl; $R^{11}$ is H; $R^{20}$ is H; and $R^{21}$ is a $C_{2-6}$ alkenyl; preferably $R^9$ is $C_{1-6}$ alkyl; $R^{11}$ is H; $R^{20}$ is H; $R^{21}$ is a $C_{2-6}$ alkenyl; and $R^{10}$ is H; more preferably $R^9$ is $C_{1-6}$ alkyl; $R^{11}$ is H; $R^{20}$ is H; $R^{21}$ is a $C_{2-6}$ alkenyl; $R^{10}$ is H; and $R^{15}$ is —OH or —$CH_2$—$CH_2$—; more preferably $R^9$ is $C_{1-6}$ alkyl; $R^{11}$ is H; $R^{20}$ is H; $R^{21}$ is a $C_{2-6}$ alkenyl; $R^{10}$ is H; $R^{15}$ is —OH or —$CH_2$—$CH_2$—; and $R^{16}$ and $R^{17}$ is $C_{1-6}$ alkyl.

Preferred steroid moieties Z incorporating further groups VI c are those in which $R^8$ is $C_{1-6}$ alkyl and $R^9$ is H and $R^{11}$ is $C_{1-6}$ alkyl; $R^{12}$ is H or —OH; $R^{15}$ is H or —OH; $R^{16}$ and $R^{17}$ are H; more preferred steroid moieties Z incorporating further groups VI c are those in which $R^8$ is $C_{1-6}$alkyl and $R^9$ is H and $R^{11}$ is $C_{1-6}$ alkyl; $R^{12}$ is H or —OH; $R^{15}$ is H or —OH; $R^{16}$ and $R^{17}$ are H and X is O.

Preferred steroid moieties of formula VI a and VI b are those having the ring structures below: still more preferably having the substitutions as set forth therein.

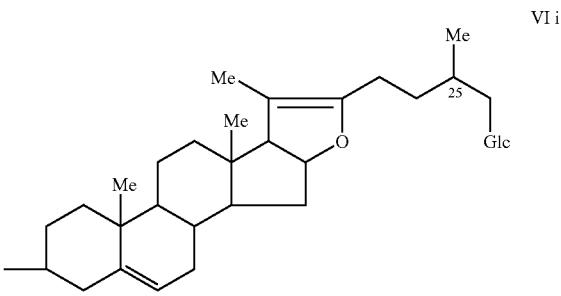

VI i

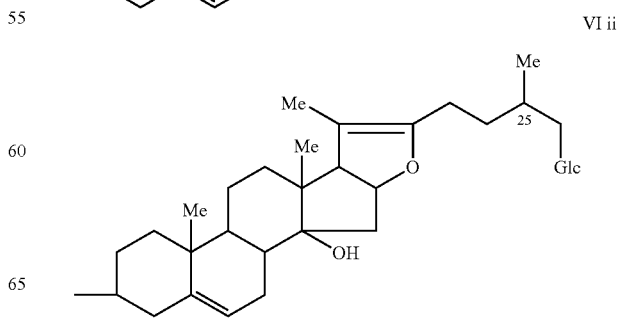

VI ii

VI iii
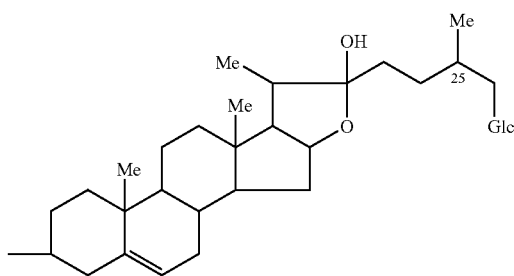
VI iv
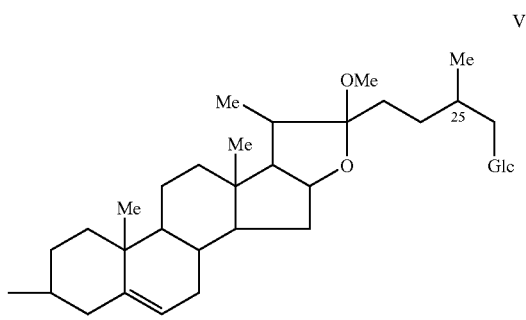
VI v
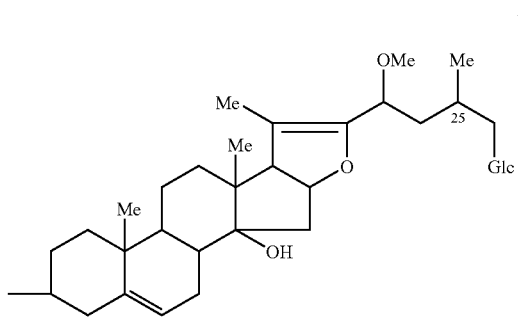
VI vi
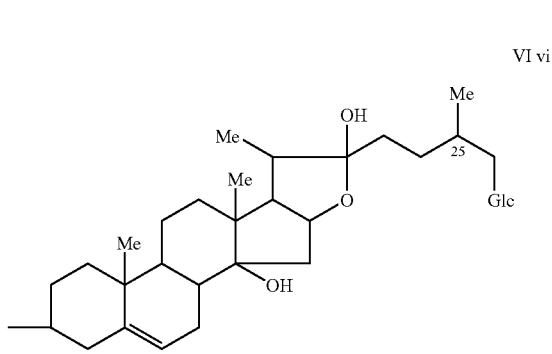
VI vii
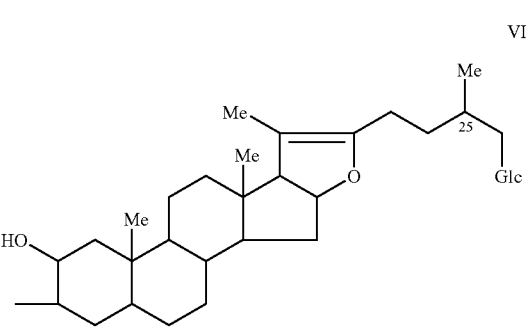
VI viii
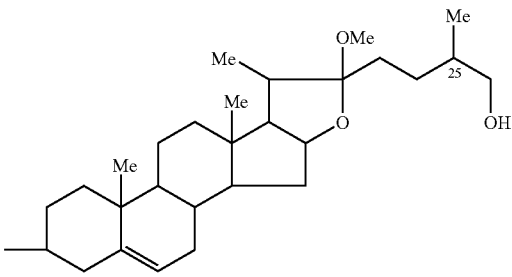
VI ix
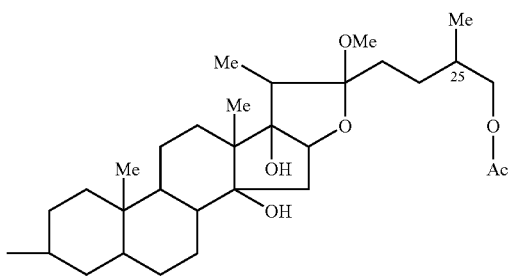
VI x
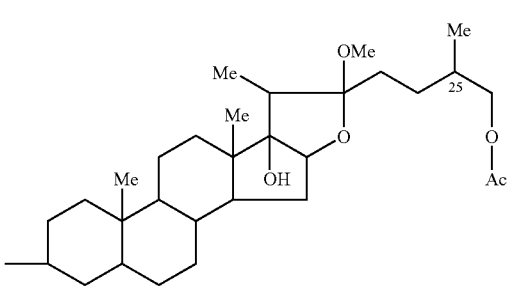
VI xi
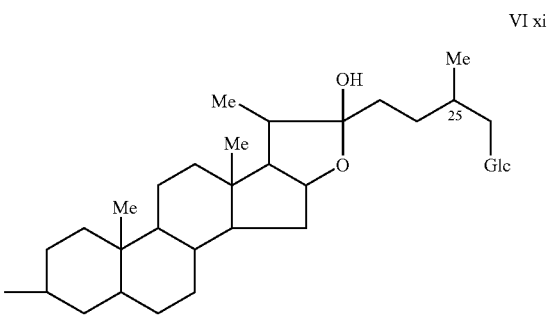
VI xii
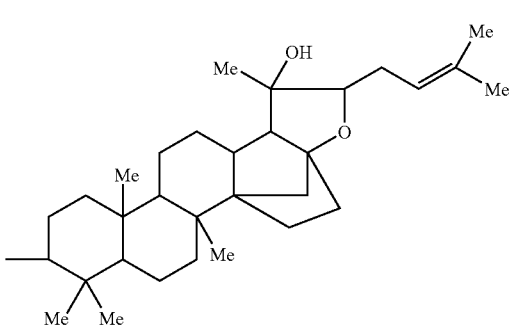

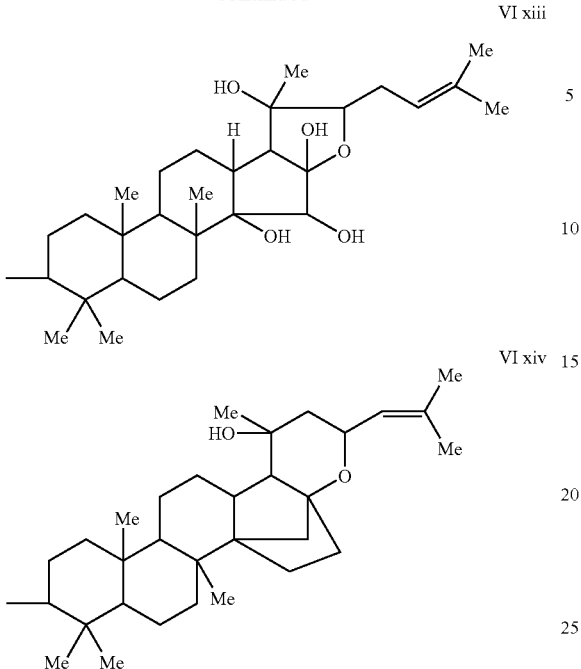

VI xiii

VI xiv

In each case the chiral centre at the carbon labelled "25" can be in either the R or S configuration.

More preferred steroid moieties, Z, of the formula VI c in which X=O are for example those having the radicals of sarsasapogenin, smilagenin, 12β-hydroxysmilagenin, rhodeasapogenin, isorhodiasapogenin, samogenin, 12β-hydroxysamogenin, markogenin, yonogenin, convallagenin A, convallagenin B, tokorogenin, tigogenin, neotigogenin, gitogenin, agigenin digitogenin, chlorogenin, paniculogenin, (25R)-spirostan-3β, 17α,21-triol, allogenin, (25R)-5α-spirostan-2α,3β,5α,6α-tetraol, (24S,25R)-5α-spirostan-2α, 3β,5α,6β,24-pentaol, yamogenin diosgenin, yuccagenin, lilagenin, ruscogenin, (25S)-ruscogenin, neopraserigenin, pennogenin, isonuatigenin, cepagenin, 24a-hydroxypennogenin, ophiogenin, sibiricogenin, convallamarogenin, neoruscogenin, hecogenin, neohecogenin, manogenin, sisalagenin and hispigenin.

Preferred steroid moieties, Z, of the formula VI c in which X=NH are for example those that have the radicals of: solasodine, soladulcidine, tomatidine and 5-dehydrotomatidine.

Preferred steroidal moieties Z of the formula VI c are those having the ring structures below; still more preferably having the substitutions as set forth therein.

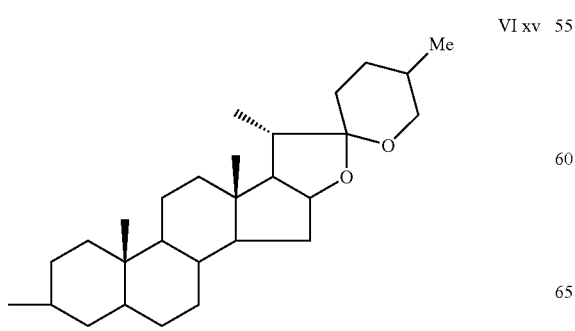

VI xv

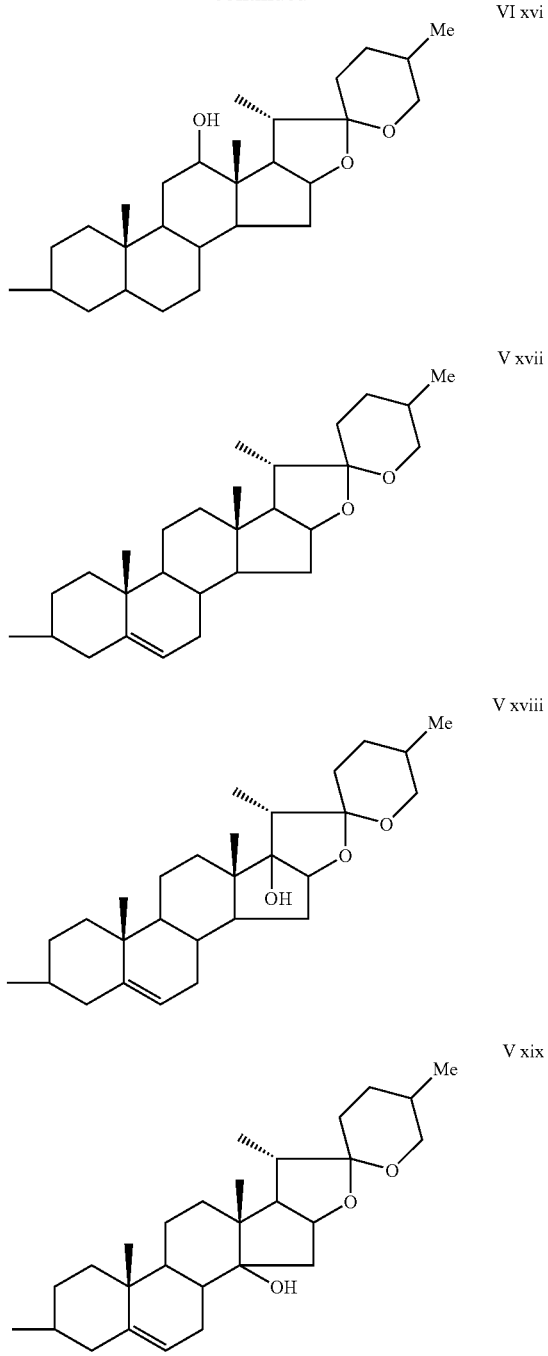

VI xvi

V xvii

V xviii

V xix

V xx

VI xxi
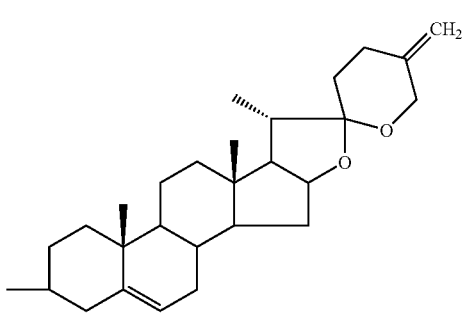
VI xxii
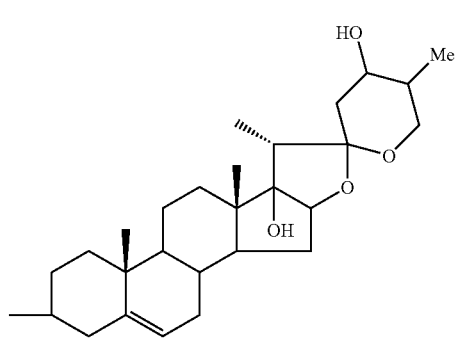
VI xxiii
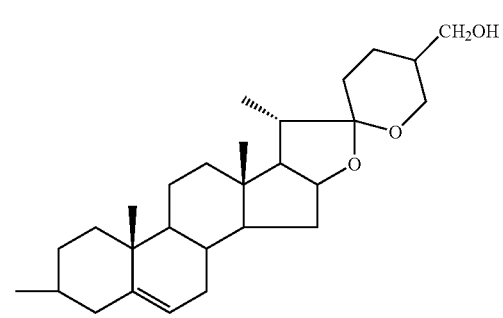
VI xxiv
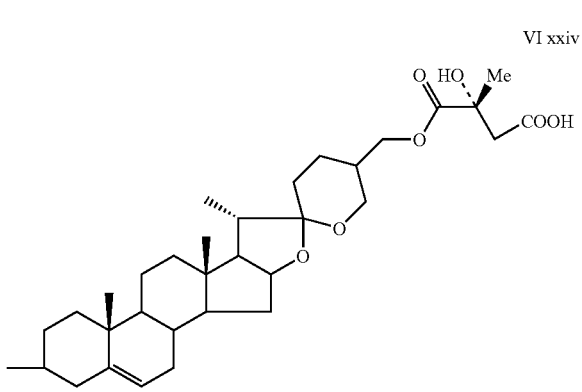
VI xxv
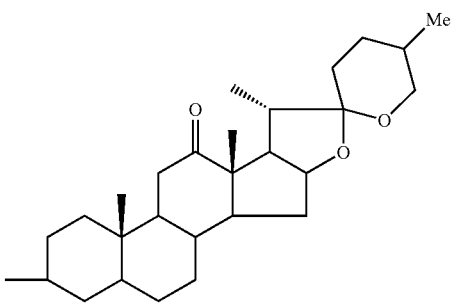
VI xxvi
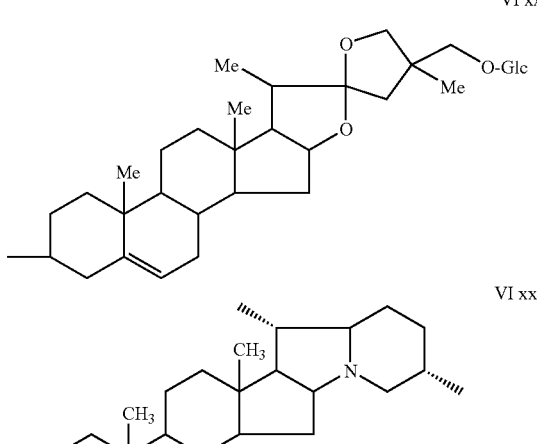
VI xxvii
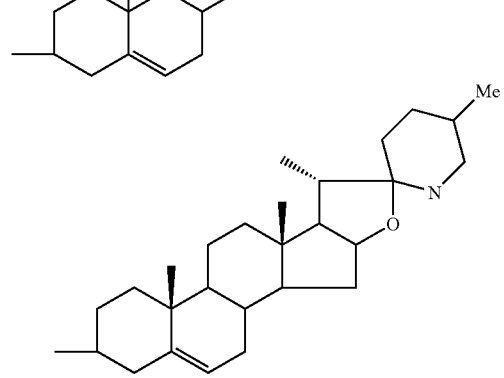
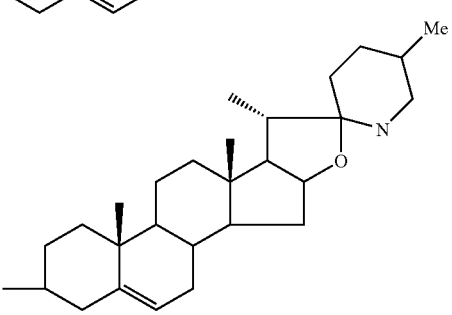
Further preferred steroidal moieties Z of the formula VI are those having the ring structures below; still more preferably having the substitutions as set forth therein.
VI xxviii
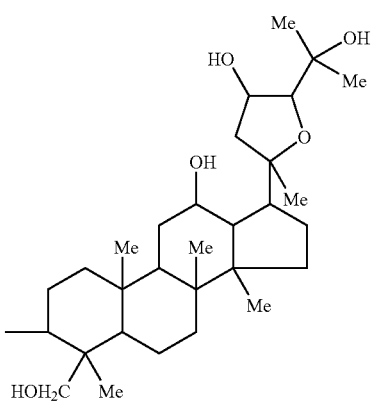

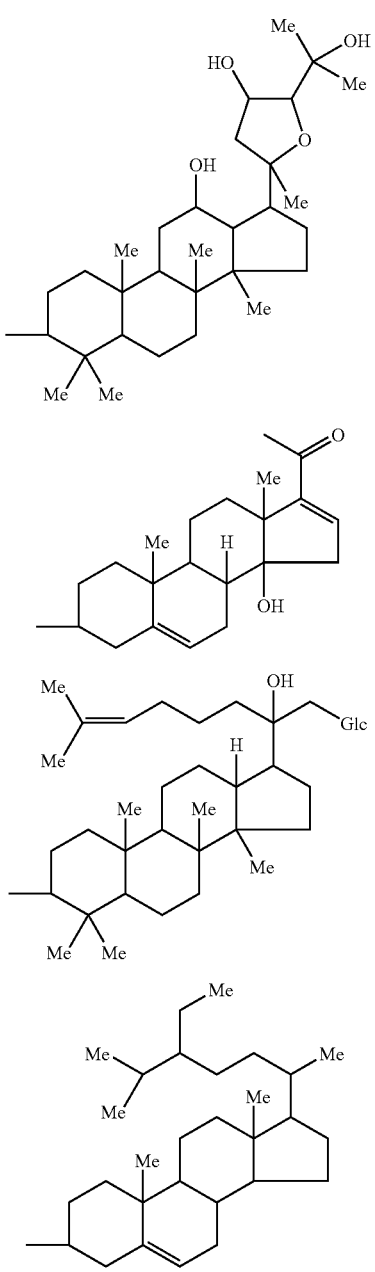

Preferred steroid moieties VI i to VI xxxii can be derived from steroidal glycoside compounds herein, of references of table 2 and additionally from references (27, 40, 76 to 78 and 86 to 93).

Preferred compounds of the formula I combine preferred Steroid moieties -Z- with preferred saccharide moieties.

In one embodiment compounds of the invention are those of the formula III in which the steroid moiety -Z- is selected from group V which incorporate the further group VIa and in which $R^7$, $R^9$, $R^{10}$, $R^{13}$, $R^{14}$, $R^{16}$, $R^{17}$ and $R^{19}$ are H; $R^{12}$ is H or —OH; $R^8$, $R^{11}$ and $R^{18}$ are —CH$_3$; $R^{15}$ is H or —OH; $R^{20}$ is —OH or —OCH$_3$ and $R^{21}$ is 4-hydroxy-3-methylbutanyl, 3-methylenebutyl substituted at the 4-position by Glc, 3-methylbutanyl substituted at the 4-position by Glc, 1-hydroxy-3-methylbutanyl substituted at the 4-position by Glc or 1-methoxy-3-methylbutanyl substituted at the 4-position by Glc. It is particularly preferred that when $R^{21}$ is 3-methylenebutyl substituted at the 4-position by Glc then the compound of the formula III is compound 25 of table 1a.

Particularly preferred compounds of the formula I are:
Protodioscin, pseudoprotodioscin, protoneodioscin, methylprotodioscin, methylprotoneodioscin, Trigoneoside IVa, glycoside F, Pardarinoside C, Pardarinoside D, dioscin, Balanitin VI, Deltonin, Shatavarin I and Shatavarin IV.

Further preferred compounds that are so far un named are Compounds 8, 12, 13, 14, 15, 16, 17, 18, 23, 24, 25 and 26 of table 2.

The preferred compounds have the following chemical names:

Protodioscin is [(3β,22α,25R)-26-(β-D-glucopyranosyloxy)-22-hydroxyfurost-5-en-3-yl O-6-deoxy-α-L-mannopyranosyl (1→2)-O-[6-deoxy-α-L-mannopyranosyl-(1→4)]-β-D-Glucopyranoside], pseudoprotodioscin is [(3β,22α,25R)-26-(β-D-glucopyranosyloxy)-furosta-5,20(22)-dien-3-yl O-6-deoxy-α-L-mannopyranosyl (1→2)-O-[6-deoxy-α-L-mannopyranosyl-(1→4)]-β-D-Glucopyranoside], protoneodioscin is [(3β,22α,25S)-26-(β-D-glucopyranosyloxy)-22-hydroxyfurost-5-en-3-yl O-6-deoxy-α-L-mannopyranosyl (1→2)-O-[6-deoxy-α-L-mannopyranosyl-(1→4)]-β-D-Glucopyranoside], methylprotodioscin is [(3β, 22α,25R)-26-(β-D-glucopyranosyloxy)-22-methoxyfurost-5-en-3-yl O-6-deoxy-α-L-mannopyranosyl (1→2)-O-[6-deoxy-α-L-mannopyranosyl-(1→4)]-β-D-Glucopyranoside], methylprotoneodioscin is [(3β,22α,25S)-26-(β-D-glucopyranosyloxy)-22-methoxyfurost-5-en-3-yl O-6-deoxy-α-L-mannopyranosyl (1→2) -O-[6-deoxy-α-L-mannopyranosyl-(1→4)]-β-D-Glucopyranoside], Trigoneoside IVa is (3β,25S)-26-(β-D-glucopyranosyloxy)-22-hydroxyfurost-5-en-3-yl O-6-deoxy-α-L-mannopyranosyl-(1→2)-O-[β-D-glucopyranosyl-(1→4)]-β-D-glucopyranoside, glycoside F is (3β,25R)-26-(β-D-glucopyranosyloxy)-22-hydroxyfurost-5-en-3-yl O-6-deoxy-α-L-mannopyranosyl-(1→2)-O-[β-D-glucopyranosyl-(1→4)]-β-D-glucopyranoside, Pardarinoside C is (3β,5α,22α,25R)-26-(acetyloxy)-14,17-dihydroxy-22-methoxyfurostan-3-yl O-6-deoxy-α-L-annopyranosyl-(1→2)-O-[β-D-glucopyranosyl-(1→)]-β-D-Glucopyranoside, Pardarinoside D is β-D-glucopyranoside, (3β,5α,22α,25R)-26-(acetyloxy)-17-hydroxy-22-methoxyfurostan-3-yl O-6-deoxy-α-L-mannopyranosyl-(1→2)-O-[β-D-glucopyranosyl-(1→4)]-β-D-glucopyranoside, dioscin is [(3β,25R)-spirost-5-en-3-yl O-6-deoxy-α-L-mannopyranosyl-(1→2)-O-[6-deoxy-α-L-mannopyranosyl-(1→4)]-β-D-glucopyranoside], Balanitin VI is (3β,25S)-spirost-5-en-3-yl-O-α-L-rhamnopyranosyl-(1→2)-O-[β-D-glucopyranosyl-β-D-glucopyranoside, Deltonin is (3β,25R)-spirost-5-en-3-yl-O-α-L-rhamnopyranosyl-(1→2)-O-[β-D-glucopyranosyl-β-D-glucopyranoside, Shatavarin I is (3β, 5β,22α,25S)-26-(β-D-glucopyranosyloxy)-22-hydroxyfurostan-3-yl O-6-deoxy-α-L-mannopyranosyl-(1→2)-O-[β-D-glucopyranosyl-(1→4)]-β-D-glucopyranoside, Shatavarin IV is (3β,5β,25S)-spirostan-3-yl O-6-deoxy-α-L-mannopyranosyl-(1→2)-O-[β-D-glucopyranosyl-β-D-glucopyranoside, Compound 8 is (3β,25R)-26-(β-D-glucopyranosyloxy)-22-methoxyfurost-5-en-3-yl O-6-deoxy-α-L-annopyranosyl-(1→2)-O-[β-D-glucopyranosyl-(1→4)]-β-D-Glucopyranoside, compound 12 is [(3β,12α,25R)-12-hydroxyspirostan-3-yl O-6-deoxy-α-L-mannopyranosyl-(1→2)—[β-D-glucopyranosyl-(1→4)]-β-D-glucopyranoside], compound 13 is [(25S)-spirost-5-ene-3β27-diol 3-O-{6-deoxy-α-L-mannopyranosyl-(1→2)—[β-D-glucopyranosyl-(1→4)]-β-D-glucopyranoside}], compound 14 is [(25R,26R)-26-methoxyspirost-5-en-3β-ol 3-O-{6-deoxy-α-L-mannopyranosyl-(1→2)-[β-D-glucopyranosyl-(1→4)]-β-D-glucopyranoside}], compound 15 is [3β,25R,27(S)]-27-(4-carboxy-3-hydroxy-3-methyl-1-oxobutoxy)spirost-5-en-3-yl O-6-deoxy-α-L-mannopyranosyl-(1→2) -O-[βD-glucopyranosyl-(1→4)]-β-D-glucopyranoside], compound 16 is [3β,25R,27(S)]-27-[(3-hydroxy-5-methoxy-3-methyl-1,5-dioxopentyl)oxy]spirost-5-en-3-yl O-6-deoxy-α-L-mannopyranosyl-(1→2)-O-[β-D-glucopyranosyl-(1→4)]-β-D-glucopyranoside], compound 17 is β-D-Glucopyranoside, (3β,25R,26R)-17-hydroxy-26-methoxyspirost-5-en-3-yl O-6-deoxy-α-L-mannopyranosyl-(1→2)-O-[β-D-glucopyranosyl-(1→4)]-β-D-glucopyranoside, compound 18 is (3β,25R,26R)-26-hydroxyspirost-5-en-3-yl O-6-deoxy-α-L-mannopyranosyl-(1→2)-O-[β-D-glucopyranosyl-(1→4)]-β-D-glucopyranoside, compound 23 is 26-O-β-D-glucopyranosylnuatigenin 3-O-α-L-rhamnopyranosyl-(1→2)-O-[β-D-glucopyranosyl-(1→4)]-β-D-glucopyranoside Compound 24 is solanidine 3-O-α-L-rhamnopyranosyl-(1→2)-O-[β-D-glucopyranosyl-(1→4)]-β-D-glucopyranoside, compound 25 is (3β,25S)-26-(β-D-glucopyranosyloxy)-22-hydroxyfurost-5,25 (27) dien-3-yl O-6-deoxy-α-L-mannopyranosyl-(1→2)-O-[β-D-glucopyranosyl-(1→4)]β-D-glucopyranoside, and compound 26 is solasodine 3-O-α-L-rhamnopyranosyl-(1→2)-O-[β-D-glucopyranosyl-(1→4)]-β-D-glucopyranoside Where any preferred substituent (such as $C_{1-6}$ alkyl, $C_{1-6}$ hydroxyalkyl) is said to be composed of from 1 to 6 carbon atoms (ie $C_{1-6}$) such substituents are more preferred with 1 to 4 carbon atoms (ie $C_{1-4}$), are more preferred still with 1 or 2 carbon atoms (ie methyl or ethyl) and are most preferred with only one carbon atom (ie are in the methyl form). Likewise where partial substituents such as the $C_{1-6}$ alkyl group or $C_{1-6}$ alkoxy group of $C_{1-6}$-alkoxy-$C_{1-6}$-alkyl are said to be composed of from 1 to 6 carbon atoms (ie $C_{1-6}$) such substituents are, independently one of the other, more preferred with 1 to 4 carbon atoms (ie $C_{1-4}$), are more preferred still with 1 or 2 carbon atoms (ie methyl or ethyl) and are most preferred with only one carbon atom (ie are in the methyl form).

Alkyl, alkenyl and alykynyl radicals may, where the number of carbons in the chain permits, be either straight-chain or branched chain. $C_{1-6}$ alkyl radicals may be, for example, methyl, ethyl, n-propyl or isopropyl, n-butyl, isobutyl or tert-butyl, isopentyl, 2,2-dimethyl propyl, n-hexyl, isohexyl and 1,3-dimethylbutyl. $C_{2-6}$ alkenyl radicals may be, for example, allyl, 1-methylprop-2-enyl, 2-methylprop-2-enyl, 2-methyl prop-1-enyl, but-2-enyl, but-3-enyl, 1-methyl-but-3-enyl, 1-methyl-but-2-enyl, 3-methylbut-2-enyl; where the alkenyl radical consists of 2-8 carbon atoms, the possible arrangements include, in addition to those possible for radicals with 2-6 carbon atoms, the following preferred radicals 5-methyl-hex-5-enyl, 4-methyl-hex-5-enyl, 3,4-dimethyl-hex-2-enyl. $C_{2-6}$. alkynyl may be, for example, propargyl, but-2-ynyl, but-3-ynyl, 1-methylbut-3-ynyl, pent-2-ynyl, pent-3-ynyl, pent-4-ynyl, 4-methyl-pent-2-ynyl. Preferably it is propargyl, 1-methylbut-3-ynyl, pent-2-ynyl, pent-4-ynyl or 4-methyl-pent-2-ynyl.

A $C_{1-6}$ hydroxyalkyl group may, where chemically possible, be either a $C_{1-6}$ monohydroxyalkyl or a $C_{1-6}$ dihydroxyalkyl group.

Where moieties may be, in turn, substituted by a saccharide moiety it is preferred that the bond is through an oxygen to form a group such as:

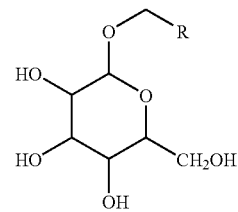

In the formula I the saccharide moiety A comprises multiple chiral centres. Thus each of the carbon atoms 1, 2, 3, 4 and 5 can, independently, be in the R or S form. Depending on the form of the anomeric carbon, A can, independently, be in either the alpha or beta anomeric form. For ring A the beta anomeric form is preferred. The saccharide moiety A can be in the D or L form; the D form is preferred. Depending on the arrangement around these chiral centres and the identity of the substituent $R_4$, the monosaccharide A can take a number of forms. Thus for example when $R^4$ is H, and $R^1$, $R^2$ and $R^3$ are —OH the saccharide moiety may, for example, be arranged as arabinopyranose, lyxopyranose, ribopyranose or xylopyranose; preferably it is xylopyranose or ribopyranose; more preferably it is xylopyranose.

When $R^4$ is —$CH_3$ and $R^1$, $R^2$ and $R^3$ are —OH the saccharide moiety is a 6-deoxy hexopyranose, and may be arranged as 6-deoxyallose, 6-deoxyaltrose, 6-deoxygalactose (fucose), 6-deoxyglucose (quinovose), 6-deoxygulose, 6-deoxyidose, 6-deoxymannose (rhamnose) or 6-deoxytalose preferably it is 6-deoxyallose or quinovose; preferably it is quinovose.

Where $R^4$ is —$CH_2OH$ and $R^1$, $R^2$ and $R^3$ are —OH the saccharide moiety is a hexopyranose and may be, for example, allose, altrose, galactose, glucose gulose, idose, mannose or talose; preferably it is allose, galactose or glucose, more preferably glucose. When $R_4$ is —$CH_2OH$, $R_2$ and $R_3$ are —OH, $R_1$ is $NR^5R^6$ and $R^5$ and $R^6$ are H the saccharide may be arranged as a pyranosamine, for example as glucosamine, mannosamine or galactosamine. When $R^4$ is —$CH_2OH$, $R^2$ and $R^3$ are —OH, $R^1$ is $NR^5R^6$ and $R^5$ is H and $R^6$ is —$COCH_3$ the saccharide may be arranged as an N-acetylpyranosamine for example N-acetylglucosamine (GlcNAc), N-acetylmannosamine or N-acetylgalactosamine (GalNAc); most preferably it is GalNAc.

Saccharides include, but are not limited to, monosaccharides, disaccharides, trisaccharides, tetrasaccharides and polysaccharides. Preferably saccharide moieties are monosaccharides, but may be independently selected as di- or oligosaccharides.

Monosaccharides include, but are not limited to, tetroses pentoses, hexoses and heptoses; tetroses pentoses and hexoses are preferred.

Tetroses may be for example aldotetroses, such as erythrose and threose and aldoketoses erithrulose.

Pentoses include, but are not limited to aldopentoses, such as arabinose, lyxose, ribose and xylose and ketopentoses such as ribulose and xylulose and deoxypentoses such as 2-deoxyribose and 3-deoxyribose. Preferred pentoses are xylose and arabinose. Pentoses may be in the furanose (eg arabinofuranose, lyxofuranose, ribofuranose and xylofuranose) or the pyranose (eg arabinopyranose, lyxopyranose, ribopyranose and xylopyranose) forms.

Hexoses include, but are not limited to aldohexoses, such as, allose, altrose, galactose, talose, gulose, idose, mannose and glucose (preferred are glucose, mannose, galactose, altrose, allose idose and talose) and ketokexoses such as fructose, psicose, sorbose and tagatose.

Hexoses may also be deoxy hexoses wherein an —OH group is replaced by an —H group at any position other than the bonded group. 6-deoxyhexoses are for example 6-deoxyallose, 6-deoxyaltrose, 6-deoxygalactose (fucose), 6-deoxyglucose (quinovose), 6-deoxygulose, 6-deoxyidose, 6-deoxymannose (rhamnose) or 6-deoxytalose. Deoxyhexoses may also be 2-deoxy, 3-deoxy, 4-deoxy and 5-deoxy hexoses. The oxygen may be lacking at more than one position. Examples of deoxyhexoses are—2-deoxy-glucose, 2-deoxygalactose, 4-deoxyfucose, 3-deoxygalactose, 2-deoxyglucose, 3-deoxyglucose, 4-deoxyglucose. Deoxyaldohexoses are preferred.

Hexoses also include hexosamines such as galactosamine, glucosamine and mannosamine, n-acteyl hexosamines such as N-acetyl-galactosamine, N-acetyl-mannosamine and N-acetylglucosamine. Preferred hexoses are aldohexoses and deoxy hexoses, particularly preferred hexoses are glucose, galactose, quinovose, fucose and rhamnose.

Hexoses may be in the furanose or pyranose form; preferably in the pyranose form.

Other monosaccharides include uronic acids, for example fructuronic acid, galacturonic acid, iduronic acid, glucuronic acid, guluronic acid, mannuronic acid and tagaturonic acid; sedoheptulose, sialic acid, neuraminic acid, muramic acid, N-acetylneuraminic acid, N-acetylmurarnic acid, O-acetylneuraminic acid, and N-glycolylneuraminic acid.

Of hexoses, aldohexoses and deoxyhexoses (particularly deoxyaldohexoses) are preferred; of pentoses, aldopentoses and deoxy-pentoses (particularly deoxyaldopentoses) are preferred.

Pharmaceutically acceptable esters of compounds of the formula 1 are for example, an ester with an aliphatic or aromatic carboxylic or sulphonic acid. Aliphatic carboxylic acids may be for example of up to 6 carbon atoms, for example a methyl, ethyl, tert-butyl succinyl or malyl. Aromatic carboxylic acids may for example benzoic acid, sulphonic acids may be methylsulphonic or p-toluenesulphonic acid, and include esters at any available esterifiable position.

Pharmaceutically acceptable esters further include known compounds in which the sugar —OH groups are esterified with an aliphatic carboxylic acid of up to 6 carbon atoms. Also included are known esters at the carbon 26-position with compounds such as hydroxymethylgluteryric acid or its methyl ester (for example compound 19 and structure VI xxiv).

Pharmaceutically acceptable ethers are, for example, with $C_{1-6}$ hydroxyalkyl compounds which may be formed at any of the available —OH groups, for example on the saccharide moieties, or steroid moieties by converting one or more of the —OH groups to alkoxy groups (e.g. 61, 84, 85 incorporated herein by reference).

A suitable pharmaceutically-acceptable salt form of the compounds of the formula I is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra(2-hydroxyethyl)ammonium, salt.

Compounds of the formula I can be extracted from a variety of plant species. Examples of sources of compounds of the invention and example purification protocols are given in the references of table 2 (which are incorporated herein by reference). Further sources of compounds of the invention and methods of isolation of such compounds are detailed in (27), particularly tables 2.2, 2.9, 2.10 and 2.11 and appendix 3- and references, therein which are incorporated herein by reference.

Many compounds of the invention are hydroxylated steroids. It is known in the art that such compounds, when exposed to solvent such as alcohols during purification or preparation, may be converted to alkoxy derivatives or to other derivatives such as methylketals (which revert to the original compounds upon drying). Particularly furostanol compounds of the formula VIa, in which the carbon at the at the 22-position of the furostanol structure, is substituted by —OH, may be converted to alkoxy derivatives when exposed to alcohols. Notably such compounds may become methoxy derivatives when purified from plant sources using methanol-containing solvents. Alternatively they may be converted to the corresponding alkoxy by reflux in an appropriate anhydrous alcohol at elevated temperature, for example methanol (36). Such alkoxylated compounds are also compounds of the invention.

Where the compounds of the invention are purified from natural sources it is preferred that they are used in isolated form. By isolated is meant that the compound is at least 1% pure, conveniently it is at least 10% pure, more conveniently at least 30% pure, preferably it is at least 50% pure more preferably it is at least 80% pure still more preferably it is at least 90% pure and most preferably it is at least 95% pure.

The purity of the compound is conveniently expressed as a ratio of UV absorption associated with the compound to UV absorption associated with other material in the sample, conveniently at 205 nm. The purity of the compound may be measured for example using a chromatography system such as for example TLC or HPLC such as are described in the references herein, particularly in those references relating to the compound in question, or in applicants co pending application WO05/060977

Alternatively, compounds of the invention may be synthesised via a number of routes known to the skilled worker. For example by glycosylation of appropriate aglycones.

A number of suitable aglycones are available commercially, alternatively an suitable aglycone may be prepared, either by isolation from a natural source (27 and references therein), by deglycosylation of a suitable glycosylated compound (for example those compounds disclosed in (27) or herein), or by chemical synthesis from a variety of starting material that are readily available.

Methods of synthesising Galβ1-3(6-deoxy)GalNAcα-conjugates are given in Paulsen et al (16) incorporated herein by reference. These methods may be adapted by the skilled worker in combination with other methods referenced herein to synthesize other compounds of the formula I.

The skilled worker will be aware of many sources of spirostanol and furostanol aglycones suitable for preparing compounds for use in the invention. For example spirostanol aglycones wherein X=O or X=NH may be, for example, sarsapogenin, smilagenin, 12β-hydroxysmilagenin, Rhodeasapogenin, Isorhodiasapogenin, Samogenin, 12β-hydroxysamogenin, Markogenin, Yonogenin, Convallagenin A, Convallagenin B, Tokorogenin, Tigogenin, Neotigogenin, Gitogenin, Agigenin Digitogenin, Chlorogenin, Paniculogenin, (25R)-Spirostan-3β, 17α21-triol, Allogenin, (25R)-5α-Spirostan-2α,3β,5α,6α-tetraol, (24S,25R)-5α-Spirostan-2α,3β,5α,6β,24-pentaol, Yamogenin Diosgenin, Yuccagenin, Lilagenin, Ruscogenin, (25S)-Ruscogenin, Neopraserigenin, Pennogenin, Isonuatigenin, Cepagenin, 24a-hydroxypennogenin, Ophiogenin, Sibiricogenin, Convallamarogenin, Neoruscogenin, Hecogenin, Neohecogenin, Manogenin, Sisalagenin, Solasodine, Soladulcidine, Tomatidine and 5-dehydrotomatidine.

Deglycosylation of, for example steroidal glycosides, may be simply carried out by acid hydrolysis, for example in a 50:50 mix of 2N HCl:dioxane at 100° C. in a sealed tube for 4.5 hrs (36—incorporated herein by reference).

Methods for the synthesis of a number of steroidal aglycones have been known for may years. For example synthesis of diosgenin, yamogenin, kryptogenin and isonarthogenin have been reported by the group of Kessar et al (58-60).

General synthetic routes to a variety of tri saccharide substituted spirostanol saponins are known (28, 29, 31, 32—incorporated herein by reference). Methods of synthesis of spirostanol saponins having 2,4 branched oligosaccharide moieties are also known (33, 28, 34, 62—incorporated herein by reference). Methods of synthesis of furostanol saponins, synthesis of derivatised saponins and interconversion of spirostanol and furostanol saponins have also been devised (30, 32 to 34, 61 to 64-incorporated herein by reference). Furthermore, furostanol and spirostanol saponins can be inter converted using a β-glucosidase and pseudosaponins maybe cyclised to form the spirostanol derivative (63,65—incorporated herein by reference).

Combinatorial approaches to saponin synthesis have also been reported (66, 30—incorporated herein by reference).

These references also provide information and further references on derivatisation of saccharide hydroxyl and hydroxyalkyl groups.

As used herein the term aglycone refers to steroidal glycosides wherein the saccharide moieties are not present (e.g. page 29 line 18). The compounds may have other substituents at the position originally occupied by the saccharide moiety. Particularly aglycones that are furostanol saponins when not glycosylated may be in the ring-closed state as the equivalent spirostanol compounds. Steroidal glycosides are compounds having a steroid or substituted steroid core, to which is attached one or more saccharide moieties. A steroidal sapogenin is the aglycone of a steroidal saponin. A steroidal saponin is a naturally derived steroidal glycoside.

An anti cell adhesion agent is an agent that reduces the adhesion of cells to a substrate such as platelets or the lining of blood vessels or other tissues, an anti cell-cell interaction agent is an agent that reduces the interaction between cells. An anti cellular extravasation agent is an agent that reduces the passage of cells from the blood stream through the walls of blood vessels.

The term "treating", as used herein, includes treating as prophylaxis or treatment of a current or remitting illness.

For the avoidance of doubt the term $C_{1-6}$ acyl is —CO—$C_{1-5}$-alkyl.

In a second aspect of the invention is provided the use of compounds of the formula I in the manufacture of a medicament for the treatment of a condition associated with detrimental activity, particularly raised activity, of the enzyme core 2 GlcNAc-T.

In a third aspect of the invention is provided the use of a compound of formula I as an anti cell adhesion agent, an anti cell-cell interaction agent or an anti cellular extravasation agent.

In a fourth aspect of the invention is provided a pharmaceutical composition comprising compound of the formula I.

Medicaments of the invention comprising compounds of the formula I will typically be prepared in a sterile and pyrogen free form. They can be administered by oral or parenteral routes, including intravenous, intramuscular, intraperitoneal, subcutaneous, transdermal, airway (aerosol), rectal, vaginal and topical (including buccal and sublingual) administration.

The medicament may be made up in liquid form in which case it will typically, in addition to the compound of the formula I, comprise a pharmaceutically acceptable diluent or it may be made up in solid form.

For oral administration, the compounds of the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavouring agents, colouring agents and preservatives. Examples of suitable inert diluents include sodium and calcium carbonate, sodium and calcium phosphate, and lactose, while corn starch and alginic acid are examples of suitable disintegrating agents. Binding agents include, for example starch and gelatine, while the lubricating agent, if present, may for example, be magnesium stearate, stearic acid or talc. If desired, the tablets may be coated with an enteric coating material, such as glyceryl mono stearate or glyceryl distearate, to delay absorption in the gastrointestinal tract. Capsules for oral use include hard gelatine capsules in which the active ingredient is mixed with a solid diluent, and soft gelatine capsules wherein the active ingredients is mixed with water or an oil such as peanut oil, liquid paraffin or olive oil Formulations for rectal administration may for example be presented as a suppository with a suitable base comprising, for example, cocoa butter or a salicylate.

Formulations suitable for vaginal administration may for example be presented as pessaries, tampons, creams, gels, pastes, foams or spray formulations containing in addition to the active ingredient such carriers as are known in the art to be appropriate.

In preparations for intramuscular, intraperitoneal, subcutaneous and intravenous use; the compounds of the invention will typically be provided in a pharmaceutically acceptable diluent to provide sterile solutions, emulsions, liposome formulations or suspensions. Typically the preparation will be buffered to an appropriate pH and isotonicity. For example suitable diluents include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives include ethyl and n-propyl p-hydroxybenzoate.

The isolated Core 2 GlcNAc-T inhibitors of the invention may also be incorporated into a food or beverage product.

In general a suitable dose of Core 2 GlcNAc-T inhibitor will be in the range of 100 ng to 10 mg per kilogram body weight of the recipient per day, preferably in the range of 1 μg to 5.0 mg/kg/d. Typically the desired dose is presented once daily or several times a day in sub doses. These sub-doses may be administered in unit dosage forms, for example, containing 1 µg to 1500 mg, preferably 40 µg to 1000 mg, and most preferably 50 µg to 700 mg of active ingredient per unit dosage form.

In the shorthand annotation:

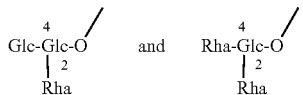

used in structures herein Glc is glucose and Rha is rhamnose. The annotation 2,3 and 2,4 denote the position of attachment of the saccharides to the central monosaccharide.

The shorthand notation

used in structures herein denotes the structure:

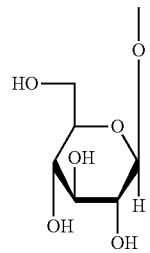

The present invention will now be described further by reference to the following non-limiting Examples, Schemes and Figures. Further embodiments falling within the scope of the claim will occur to those skilled in the art in the light of these.

EXAMPLES

Table 1 Example Compounds of the Invention.

TABLE 1a

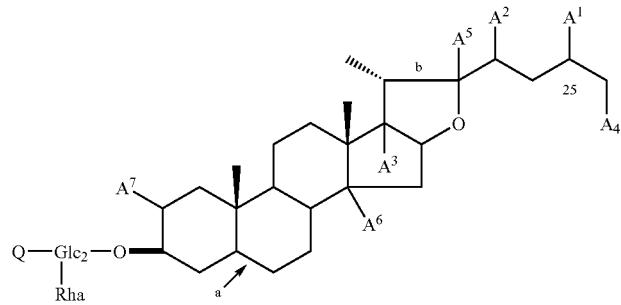

| Compound | Q | $A^1$ | $A^2$ | $A^3$ | $A^4$ | $A^5$ | $A^6$ | $A^7$ | 25 R/S | Bond a | Bond b |
|---|---|---|---|---|---|---|---|---|---|---|---|
| 1 | 4-Rha | Me | H | H | Glc | OH | H | H | R | Double | Single |
| 2 | 4-Rha | Me | H | H | Glc | Absent | H | H | R | Double | Double |
| 3 | 4-Rha | Me | H | H | Glc | OH | H | H | S | Double | Single |
| 4 | 4-Rha | Me | H | H | Glc | OMe | H | H | R | Double | Single |
| 5 | 4-Rha | Me | H | H | Glc | OMe | H | H | S | Double | Single |
| 6 | 4-Glc | Me | H | H | Glc | OH | H | H | S | Double | Single |
| 7 | 4-Glc | Me | H | H | Glc | OH | H | H | R | Double | Single |
| 8 | 4-Glc | Me | H | H | Glc | OMe | H | H | R | Double | Single |
| 9 | 4-Glc | Me | H | OH | —O•CO•CH$_3$ | OMe | OH | H | R | Single | Single |
| 10 | 4-Glc | Me | H | OH | —O•CO•CH$_3$ | OMe | H | H | R | Single | Single |
| 21 | 4-Glc | Me | H | H | Glc | OH | H | H | S | Single | Single |
| 25 | 4-Glc | =CH$_2$ | H | H | Glc | OH | H | H | — | Double | Single |
| 27*** | 3-Glc | Me | H | H | Glc | OH | H | H | R | Double | Single |

***comparative compound

TABLE 1b

| Comp. | Q | A₁ | A₂ | A₃ | A₄ | A₅ | A₆ | 25R/S | Bond a |
|---|---|---|---|---|---|---|---|---|---|
| 11 | 4-Rha | Me | H | H | H | H | H | R | Double |
| 12 | 4-Glc | Me | H | H | H | OH | H | R | Single |
| 13 | 4-Glc | —CH₂OH | H | H | H | H | H | S | Double |
| 14 | 4-Glc | Me | H | H | H | H | OMe | R | Double |
| 15 | 4-Glc | * | H | H | H | H | H | R | Double |
| 16 | 4-Glc | ** | H | H | H | H | H | R | Double |
| 17 | 4-Glc | Me | H | OH | H | H | OMe | R | Double |
| 18 | 4-Glc | Me | H | H | H | H | OH | R | Double |
| 19 | 4-Glc | Me | H | H | H | H | H | S | Double |
| 20 | 4-Glc | Me | H | H | H | H | H | R | Double |
| 22 | 4-Glc | Me | H | H | H | H | H | S | Single |

Substituent "*" =

Substituent "**" =

TABLE 1c

Further example compounds of the invention

| Compound | Structure |
|---|---|
| 23 | 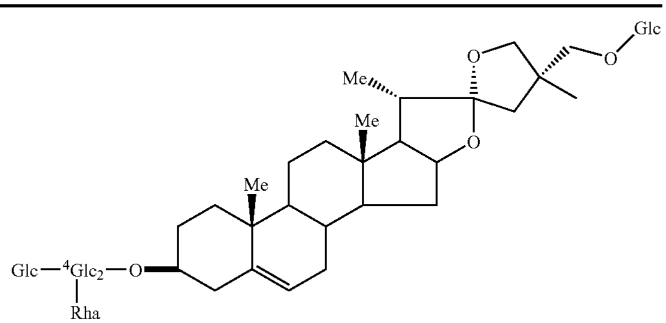 |
| 24 | 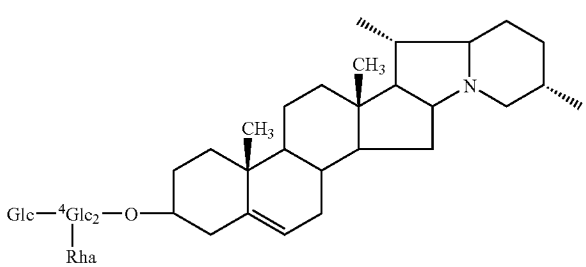 |

TABLE 1c-continued

Further example compounds of the invention

| Compound | Structure |
|---|---|
| 26 | Steroidal alkaloid glycoside structure with Glc—⁴Glc₂—O— attached to steroid core bearing spiro-piperidine (N-Me); Rha branching from Glc₂ |

TABLE 2

Key to example compounds of the invention and references

| Compound | Example references | Compound name |
|---|---|---|
| 1 | 36 | Protodioscin |
| 2 | 37 | Pseudoprotodioscin |
| 3 | 36 | Protoneodioscin |
| 4 | 36 | Methylprotodioscin |
| 5 | 36 | Methylprotoneodioscin |
| 6 | 17 | Trigoneoside IVa |
| 7 | 22, 17 | Glycoside F, protodeltonin, deltoside, |
| 8 | 42 | No name |
| 9 | 19 | Pardarinoside C |
| 10 | 19 | Pardarinoside D |
| 11 | 39 | Dioscin |
| 12 | 38 | Not named |
| 13 | 20, 40, 41, 42 | Not named |
| 14 | 40, 42 | Not named |
| 15 | 40, 41, 20, 21 | Not named |
| 16 | 41, 20 | Not named |
| 17 | 42 | Not named |
| 18 | 43 | Not named |
| 19 | 26, 42, 25 | Balanitin VI |
| 20 | 24, 71 | Deltonin |
| 21 | 18, 23 | Shatavarin I |
| 22 | 18, 23 | Shatavarin IV |
| 23 | 20 | Not named |
| 24 | 21 | Not named |
| 25 | WO05060977 | Not named |
| 26 | 20 | Not named |
| 27 | 36 | Protogracillin *** |

*** comparative example compound.

Example 1

Biological Activity of Compounds

All compounds used herein were supplied by Chromadex Inc. 2952 S. Daimler Street Santa Ana Calif. 92705. Compounds used were at least 88% pure

TABLE 4

Purity of compounds used

| Compound | Number | Purity |
|---|---|---|
| Protodioscin | 1 | 93.3% |
| Pseudoprotodioscin | 2 | 88.6% |

TABLE 4-continued

Purity of compounds used

| Compound | Number | Purity |
|---|---|---|
| Dioscin | 11 | 90.8% |
| Trigoneoside IVa | 6 | 89% |
| Glycoside F | 7 | 80.3% |
| Shatavarin I | 21 | >95% |
| ***Protogracillin | 26 | 98.8% |

Purity was determined by HPLC using UV absorption at 205 nm

1a. Cell Culture

The human leukocytic cell-line (U937) was cultured in RPMI supplemented with 10% foetal calf serum, 2 mM glutamine, 100 IU/ml penicillin and 100 μg/ml streptomycin.

1b. Assay of Core 2 GlcNAc-T Activity (i). Glucose induction of Core 2 GlcNAc-T leukocytes (U937 cells) were exposed to normal glucose (5.8 mM) or high glucose (15 mM) for 24 hours at 37° C. After incubation, the cells maybe lysed and frozen at −20° C. until used for the measurement of core 2 GlcNAc-T. or used immediately.

(ii). TNF-α induction of core 2 GlcNAc-T. Human leukocytes (U937 cells) were exposed to human recombinant TNF-alpha (8 pg/ml) in the presence and absence of test compounds After 24 h incubation, the activity of core 2 GlcNAc-T was measured, and expressed as pmoles/h/mg protein (iii). Cell free assay of core 2 GlcNAc-T in cell free assays of core 2 GlcNAc-T Heart lysates from either from TNF-alpha over expressing transgenic mice (female, B6.SJL-Tg (TNF) supplied by Taconic-M+B, Bomholtveg 10, 8680 Ry, Denmark) or from BB rats (Festing 1979) was exposed to various concentrations of test compound for 1 h at 37° C. Activity of core 2 GlcNAc-T was measured, and expressed as pmoles/h/mg protein.

1c. Measurement of Core 2 GlcNAc-T Activity

To measure core 2 GlcNAc-T activity, leukocytes were washed in PES, frozen and lysed in 0.9% Triton X-100 at 0° C. The activity of core 2 GlcNAc-T was measured as described below. Cell free assays are preformed by substituting heart lysates for cell lysates.

The reaction was performed in a reaction mixture containing 50 mM 2(N-morpholino)ethanesulfonic acid (MES, Sigma, Dorset, UK), pH 7.0, 1 mM UDP-6 [$^3$H]-N-acetylglucosamine (16,000 dpm/nmol, NEN Life Science Products, Hounslow, UK), 0.1 M GlcNAc (Sigma, Dorset, Okla.), 1 mM Galβ1-3GalNAcα-p-nitrophenol (Sigma, Dorset, UK) as substrate, and 16 μl of lysate (100-200 μg protein) for a final volume of 32 µl. After incubating the mixture for 1 hour at 37° C., the reaction was terminated with 1 ml of ice-cold distilled water and processed on a C18 Sep-Pak column (Waters-Millipore, Watford, UK). After washing the column with 20 ml of distilled water, the product was eluted with 5 ml of methanol. The radioactivity of the samples was counted in a liquid scintillation E-counter (LKB-Wallac, London, UK).

Endogenous activity of core 2 GlcNAc-T was measured in the absence of the added acceptor. The specific activity was expressed as pmoles/h/mg of cell protein. In each case, the protein concentration was determined with BioRad protein assay (BioRad, Hertfordshire, UK). Results are shown in table 5.

TABLE 5

Approximate $IC_{50}$ values (nM) for example compounds

| Compound | Number | Cell free assay | Cell based assay |
|---|---|---|---|
| Protodioscin | 1 | 20 ** | a |
| Pseudoprotodioscin | 2 | 35 * | 50 |
| Dioscin | 11 | 40 * | 75 |
| Trigoneoside IVa | 6 | 0.9 * | 75 |
| Glycoside F | 7 | 5 ** | b |
| Shatavarin I | 21 | 1 * | 0.75 |
| Shafavarin IV | 22 | c ** | † |
| *** Protogracillin | 26 | 3 * | 0.25 |

* Cell free assays were carried out on heart lysates of TNF-α mice as described above.
** Cell free assays were carried out on heart lysates of BB rats as described above.
a 33% inhibition at 20 nM
b 100% inhibition at 22 nM n BB rat heart lysate
c 89% inhibition at 22 nM in BB rat heart lysate
† no activity detected at 22.5 nM
*** comparative compound Compound C (at 20 ng/ml) was found to inhibit Core 2 GlcNAc-T approximately 98.5% compared to controls, in TNF-☐ treated Human leukocytes (U937 cells). The sample of compound C was approximately 82.5% pure by HPLC at 205 nM The approximate $IC_{50}$ of Trigoneoside IVa was found to be between 0.25 nM and 0.9 nM in cell free systems. Further analysis of a sample prepared according to applicants co pending WO05/060977 indicates that it contains approximately 7.5% protodioscin and 9% Trigonelloside C (17).

The $IC_{50}$ of Glycoside F was found to be approximately 5 nM. Further analysis of the preparation indicates that it contains a small amount of Trigonelloside C.

The $IC_{50}$ of Protodioscin (93.3% pure) produced as described in applicants co pending WO05/060977 was found to be approximately 20 nM. The sample contained 1.5% Trigoneoside IVa. A sample prepared from *Tribulus terrestris* (Chromodex Inc. 2952 S. Daimler Street Santa Ana Calif. 92705), which was 97% pure, and had an NMR spectrum consistent with protodioscin, appeared to demonstrate no activity at concentrations of 50 µM. Thus Trigoneoside IVa activity could account for at least some of the activity seen in the protodioscin sample prepared as per WO05/060977.

Trigonelloside C is similar to Protodioscin but is the opposite isomer at carbon 25. A preparation of this compound according to co pending WO05/060977 was 98.2% pure and contained no measurable quantity of other Core 2 GlcNAc-T inhibitors. A preparation of Trigonelloside C prepared according to WO05/060977 inhibited Core 2 GlcNAc-T 69% at 2.5 nM.

REFERENCES

1. Ellies L. G. et al., *Immunity* 9, 881-890 (1998)
2. Brockhausen I. et al., *Cancer Res.* 51, 1257-1263 (1991)
3. Renkonen J. et al., *APMIS* 109, 500-506 (2001)
4. Machida E. et al., *Cancer Res.* 61, 2226-2231 (2001)
5. Dalziel M. et al., *Biol. Chem.* 276, 11007-11105 (2001)
6. Perandio M. et al., *Blood* 97, 3812-3819 (2001)
7. Yousefi S. et al., *J. Biol. Chem.* 266, 1772-1782 (1991)
8. Higgins E. A. et al., *J. Biol. Chem.* 266, 6280-6290 (1991)
9. Piller F. et al., *J. Biol. Chem.* 263, 15146-15150 (1988)
10. Koya D. et al., *FASEB J.* 13, 2329-2337 (1999)
11. Nishio Y. et al., *J. Clin. Invest.* 96, 1759-1767 (1995)
12. Tsuboi S. et al., *Bioassays* 23, 46-53 (2001)
13. Tsuboi S. et al., *EMBO J.* 16, 6364-6373 (1997)
14. Tsuboi S. et al., *J. Biol. Chem.* 273(46), 30680-30687 (1998)
15. Kuhns W. et al., *Glycoconjugate Journal* 10 381-394 (1993)
16. Paulsen H. et al., Leibigs Ann. Chem. 747-758.(1992)
17. Yoshikawa M. et al., Heterocycles 47, 397-405 (1998).
18. Ravikumar P. R. et al., Indian J. Chem. 26B, 1012-1017 (1987).
19. Shimomura H. et al., Phytochemistry 28, 3163-3170 (1989).
20. Mirmaki Y and Sasheda Y. Chem. Pharm. Bull. 38(11), 3055-9(1990).
21. Sashida Y. et al., Chem. Pharm. Bull. 39(9), 2362-8(1991)
22. Akhov L. S. et al., J. Agric. Food Chem. 47(8), 3193-3196 (1999)
23. Joshi J. et al., Indian J. Chem. 27B, 12-16 (1988).
24. Vasil'eva I. S. et al., *Appl. Biochem. Microbiol.* 31, 206-209 (1995).
25. Sharma et al., Phytochemistry. 33(3):683-6. (1993).
26. Petit G. et al., Journal of natural products 54, 1491-1502.
27. Hostettman K. and Marston A. Saponins. Cambridge University Press UK. (1995).
28. Deng S et al., Carbohydr Res. 30; 317(1-4):53-62. (1999).
29. Li B et al., Carbohydr Res.; 9; 331(1):1-7. (2001).
30. Yu B et al., J Comb Chem.; 3(5):404-6. (2001).
31. Yu B., et al., Tetrahedron letters, 42, 77-79 (2001).
32. Yu B et al., J Org Chem.; 13; 67(25):9099-102 (2002).
33. Cheng M S et al., J Org Chem.; 2; 68(9):3658-62 (2003)
34. Du Y et al., Org Lett.; 2; 5(20):3627-30.(2003).
35. Mimaki Y. et al., *Chem Pharm Bull* (Tokyo). 46(11):1829-32 (1998).
36. Hu K. et al Planta Medica, 63(2), 161-165 (1997).
37. Dong M. et al., Planta Med. 67(9):853-7 (2001).
38. Ori K. et al. *Phytochemistry*. 31(8):2767-75 (1992).
39. Kawasaki T. et al., *Chemical & Pharmaceutical Bulletin;* 22(9), 2164-75 (1974).
40. Mimaki Y. et al *Phytochemistry* 37(1):227-32 (1994).
41. Nakamura O. et al., *Phytochemistry.* 36(2):463-7 (1994).
42. Mimaki Y. et al., *Chem Pharm Bull* (Tokyo). 46(11):1829-32 (1998).
43. Haladova M. et al., *Pharmazie,* 54(2), 159-160 (1999).
44. Liu H. et al,. *Chem. Pharm. Bull.* 51(9), 1089-1091 (2003).
45. Hindsgaul O. et al., *J Biol. Chem.* 266(27):17858-62 (1991).
46. Toki D. et al, *Biochem Biophys Res Commun.* 198(2):417-23 (1994).
47. Kumar R. et al., *Blood.* 15; 88(10):3872-9 (1996).
48. Stoica S. et al., *J Heart Lung Transplant.* 24(5):593-601 (2005).
49. Dedrick R. L. et al., *Expert Opin Biol Ther.* 3(1):85-95 (2003).
50. Hansen A. et al., *J Am Coll Cardiol.* 18; 44(4):887-91 (2004).
51. Wang K. et al., *Thromb Haemost.* 88(1):149-54 (2002).

52. Tanguay J. et al., *Thromb Haemost.* 91(6):1186-93 (2004).
53. Bienvenu J. et al., *Circulation.* 27; 103(8):1128-34 (2001).
54. Inoue T. et al., *J Leukoc Biol.* 77(3):287-95 (2005).
55. Rijcken E. et al., *Am J Physiol Gastrointest Liver Physiol.* 287(1):G115-24 (2004).
56. Strauss E. et al., *Invest Ophthalmol Vis Sci.* 40(7):1336-421 (1999).
57. Hickey M. et al., *J Immunol.* 168(9):4728-36 (2002).
58. Kessar S. et al., *Tetrahedron.* 24(2):905-7 (1968).
59. Kessar S. et al., *Tetrahedron* 24(2):899-904 (1968).
60. Kessar S. et al., *Tetrahedron.* 24(2):887-92 (1968).
61. Li M et al., *Carbohydr Res.* 20; 338(2): 117-21 (2003).
62. Lehmann M. et al,. *Carbohydr Res.* 337(21-23): 2153-9 (2002).
63. Tobari A. et al., *Eur J Med Chem.* 35(5): 511-27 (2000).
64. Wang S. M. et al., *Steroids.* 69(10): 599-604 (2004).
65 Inoue K. et al., *Phytochemistry* 41(3), 725-7(1996).
66. Lautrette S. et al., *Chem Commun* (Camb). 7; (5): 586-7 (2004).
67. Chow F. et al., *Nephrol Dial Transplant.* 19(12):2987-96 (2004).
68. Myers D. et al., *Thromb Haemost.* 87(3):374-82 (2002).
69. Lanteri M. et al., *Glycobiology.* 13(12):909-18 (2003).
70. Yago T. et al., *J Biol Chem.* 26; 278(39):37987-97 (2003).
71. Vasil'eva I. et al., *Prikl Biokhim Mikrobiol.* 20(3):404-6 (1984).
72. Akhov L. S. et al *Proc. Phytochem. Soc. Euprope* 45, 227-231 (2000).
73. Kim S. Y. et al *Arch. Chem. Res.* 22 (3) 313-316 (1999).
74. Vasil'eva I. S. and Paseshnichenko V. A. Adv. Exp. Med. Biol. 404, 15-22 (1996).
75. Oda K et al *Biol. Chem.* 381(1):67-74 (2000).
76. Li X. et al *Phytochemistry* 29(12), 3893-8 (1990).
77. Hernandez et al *bioorganic and med. chem.* 12(16) 4423-4429 (2004).
78. Renault J. et al, *Phytochemistry,* 44(7), 1321-1327 (1997).
79. Kim S Y et al *Arch Pharm Res.* 22(3):313-6 (1999).
80. Matsuda H et al *Bioorg Med Chem Lett.* 24; 13(6): 1101-6 (2003).
81. Dang B. et al *J Leukoc Biol.* 72(4):702-10 (2002).
82. Theoret J. et al *J Pharmacol Exp Ther.* 298(2):658-64 (2001).
83. Festing M. F. W. (Ed.). Inbred strains in biomedical research. The Macmillan Press LTD, London (1979). ISBN 0-333-23809-5.
84. Purdie and Irvine, *J. Chem. Soc.* 87, 1022 (1905).
85. Haworth and Hirst, *J. Chem. Soc.* 119, 193 (1921).
86. Zheng Q. et al *Steroids,* 69(2), 111-119 (2004).
87. Yoshikawa K et al. *Chemical & Pharmaceutical Bulletin,* 40(9), 2287-91 (1992).
88. Yoshikawa K. et al *Chemical & Pharmaceutical Bulletin,* 40(9), 2275-8 (1992).
89. Chen C. et al *Yunnan Zhiwu Yanjiu,* 9(4), 495-502 (1987).
90. Fujita S. et al *Phytochemistry,* 38(2), 465-72 (1995).
91. Yin F. et al *J. Nat. Products,* 67(6), 942-952 (2004).
92. Sang S. Phytochemistry, 52(8), 1611-1615 (1999).
93. Chen C. et al *Yunnan Zhiwu Yanjiu,* 6(1), 111-17 (1984).

The invention claimed is:
1. A method of treating a subject in need of therapy for a condition involving detrimental activity of the enzyme Core 2 GlcNAc-T comprising administering to the subject a therapeutically effective amount of an inhibitor of core 2 GlcNAc-T of formula (III):

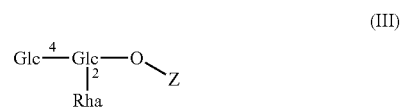

wherein Z is a steroid moiety of the formula (VI):

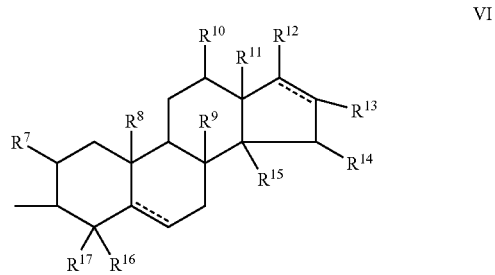

the group Z incorporating additional group (VIa) or (VIc):

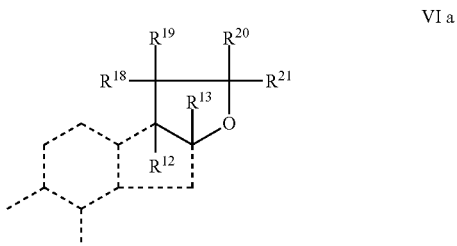

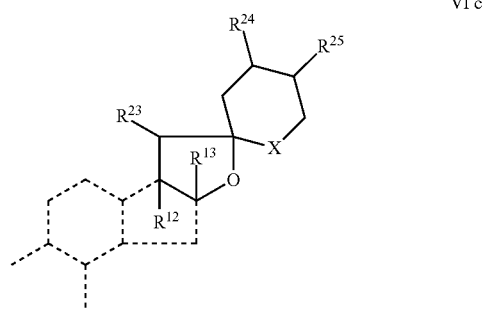

wherein:
when the steroid group incorporates additional group (VIa):
$R^7$, $R^{12}$, $R^{14}$, $R^{15}$ and $R^{19}$ are independently selected from H and —OH;
$R^8$, $R^{11}$ and $R^{18}$ are —CH$_3$;
$R^9$, $R^{13}$, $R^{16}$ and $R^{17}$ are H;
$R^{10}$ is H or —OH or the H normally present is absent and $R^{10}$ is =O;
$R^{19}$ is H or —OH;
$R^{20}$ is H, —OH or —OCH$_3$ or $R^{19}$ and $R^{20}$ taken together represent the second bond of a double bond joining adjacent carbon atoms;

$R^{21}$ is selected from the group consisting of 3-methylenebutyl substituted at the 4-position by glucose, 4-hydroxy-3-methylbutanyl, 3-methylbutanyl substituted at the 4-position by glucose, 1-hydroxy-3-methylbutanyl substituted at the 4-position by glucose or 1-methoxy-3-methylbutanyl substituted at the 4-position by glucose; and

----- represents either a single bond or a double bond;
and wherein when the steroid group incorporates additional group (VIc):
$R^7, R^{12}, R^{14}, R^{15}$ and $R^{24}$ are independently selected from H and —OH;
$R^8, R^{11}$ and $R^{23}$ are —$CH_3$;
$R^9, R^{13}, R^{16}$ and $R^{17}$ are H;
$R^{10}$ is H or —OH or the H normally present is absent and $R^{10}$ is =O;
$R^{25}$ is —$CH_3$, —$CH_2OH$ or =$CH_2$;
X is O or NH; and

----- represents either a single bond or a double bond;
or a pharmaceutically acceptable salt, ether or ester form thereof; and
wherein the condition associated with detrimental activity of Core 2 GlcNAc-T is selected from the group consisting of: vascular diseases, autoimmune conditions, inflammatory conditions, Wiskott Aldrich syndrome and cancer metastasis.

2. A method according to claim 1 in which X is O.

3. A method according to claim 1 wherein when the steroid group incorporates additional group (VIa):
$R^7, R^9, R^{10}, R^{13}, R^{14}, R^{16}, R^{17}$ and $R^{19}$ are H; $R^{12}$ is H or —OH; $R^8, R^{11}$ and $R^{18}$ are —$CH_3$; $R^{15}$ is H or —OH; $R^{20}$ is —OH or —$OCH_3$ and $R^{21}$ is 4-hydroxy-3-methylbutanyl, 3-methylenebutyl substituted at the 4-position by glucose, 3-methylbutanyl substituted at the 4-position by glucose, 1-hydroxy-3-methylbutanyl substituted at the 4-position by glucose or 1-methoxy-3-methylbutanyl substituted at the 4-position by glucose.

4. A method according to claim 1 wherein the group Z incorporating additional group (VIa) is selected from the group consisting of:

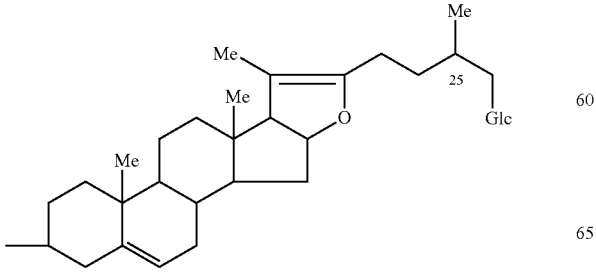

VI i

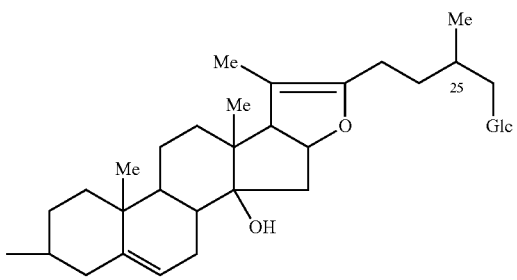

VI ii

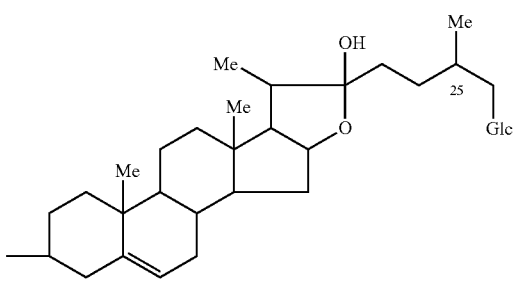

VI iii

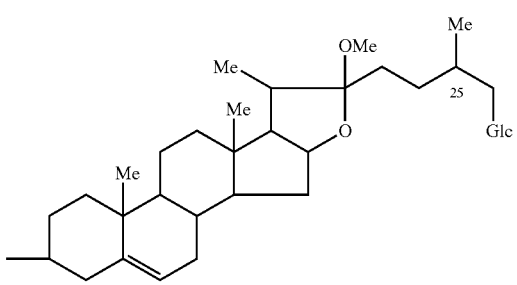

VI iv

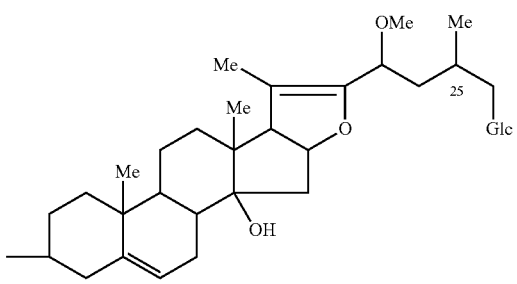

VI v

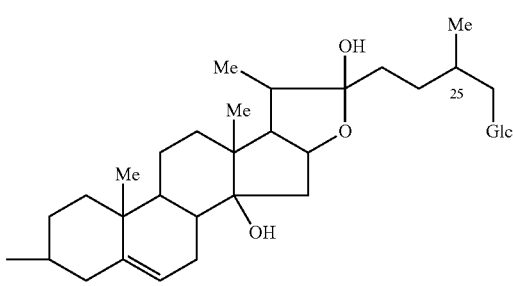

VI vi

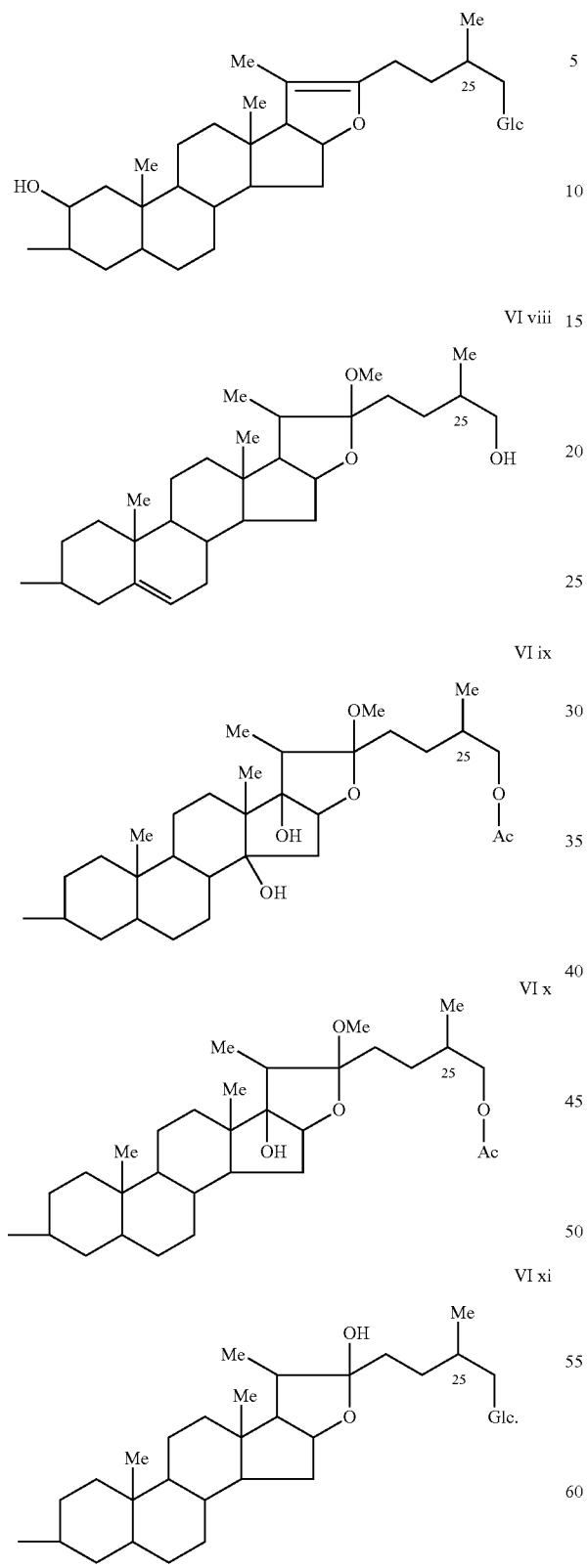
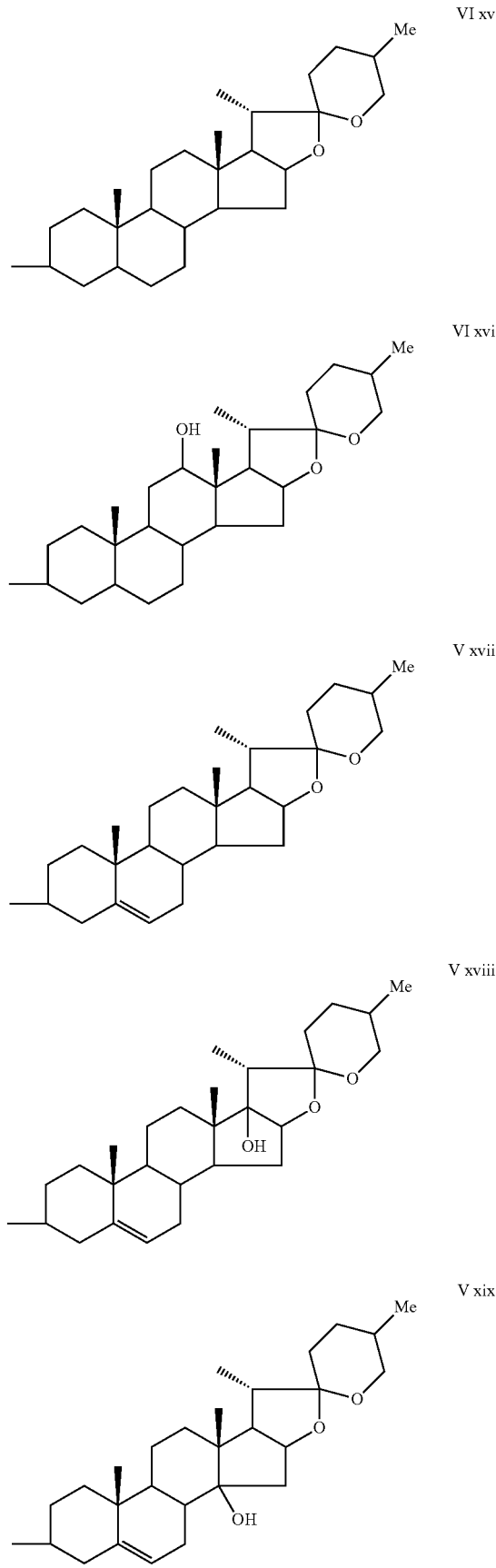
5. A method according to claim 1 wherein the group Z incorporating additional group (VIc) is selected from the group consisting of:

V xx
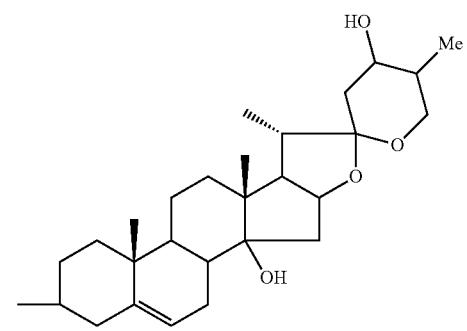

VI xxi
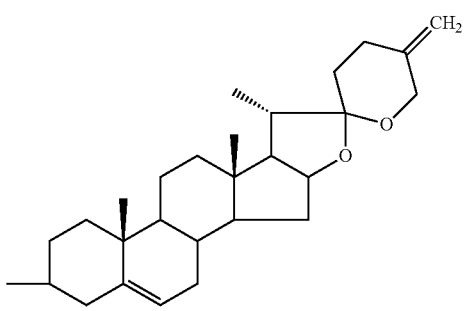

VI xxii
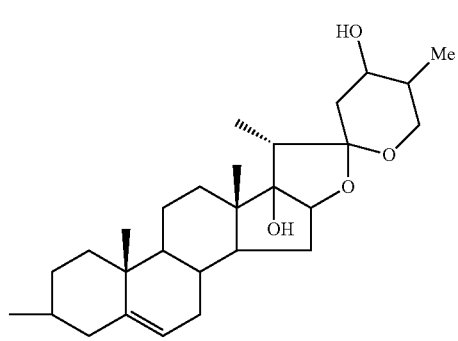

VI xxiii
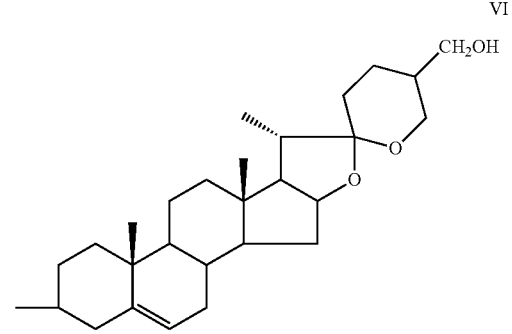

VI xxiv
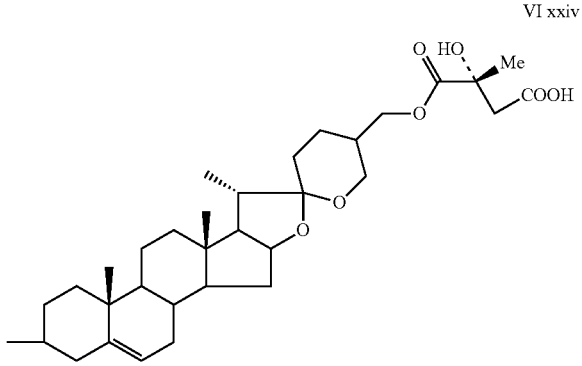

VI xxv
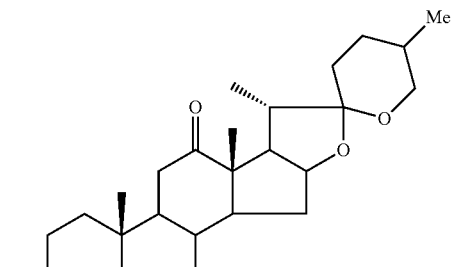

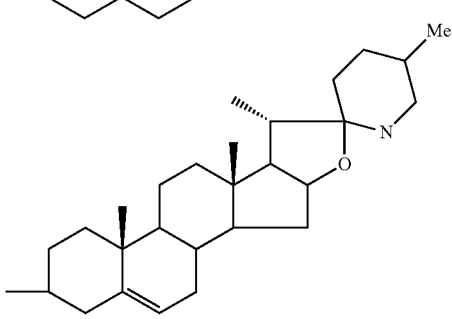

6. A method according to claim 1 in which the compound is selected from the group consisting of:
Trigoneoside IVa, glycoside F, Pardarinoside C, Pardarinoside D, Balanitin VI, Deltonin, Shatavarin I, Shatavarin IV, compound 8, compound 12, compound 13, compound 14, compound 15, compound 16, compound 17, compound 18 and compound 25.

7. A method of treatment according to claim 1 wherein the condition to be treated is selected from diabetic retinopathy, diabetic cardiomyopathy and diabetic nephropathy.

8. A method of treatment according to claim 1 wherein the condition to be treated is atherosclerosis.

9. A method of treatment according to claim 1 wherein the condition to be treated is rheumatoid arthritis.

10. A method of treatment according to claim 1 wherein the condition to be treated is asthma.

11. A method of treatment according to claim 1 wherein the condition to be treated is cancer metastasis.

12. A method of treatment according to claim 1 wherein the condition to be treated is multiple sclerosis.

13. A method of treatment according to claim 1 wherein the condition to be treated is selected from inflammatory bowel disease, ileitis, Crohn's disease, cholitis, pancreatitis, ulcerative cholitis, cholicystitis, nephritis, gastritis, diverticulitis, gastric and duodenal ulcers and irritable bowel syndrome.

14. A method of treatment according to claim 1 wherein the condition to be treated is psoriasis.

15. A method of treatment according to claim 1 wherein the condition to be treated is acute leukocyte mediated lung injury.

16. A method of treatment according to claim 1 wherein the condition to be treated is selected from ischemia reperfusion injury, restenosis and thrombosis.

17. A method of treatment according to claim 1 wherein the condition to be treated is lupus.

18. A method of treatment according to claim 1 wherein the condition to be treated is selected from traumatic shock and septic shock.

19. A method of treatment according to claim 1 wherein the condition to be treated is Wiskott-Aldrich syndrome.

20. A method of treatment according to claim 1 wherein the condition to be treated is selected from cirrhosis, fulminant hepatitis, hepatorenal syndrome and jaundice.

21. A method of treating a subject in need of therapy for a condition involving detrimental activity of the enzyme Core 2 GlcNAc-T comprising administering to the subject a therapeutically effective amount of an isolated compound of formula (III) of at least 1% purity:

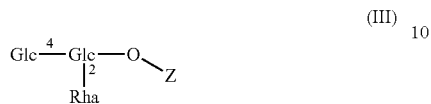

wherein Z is a steroid moiety of the formula (IV);

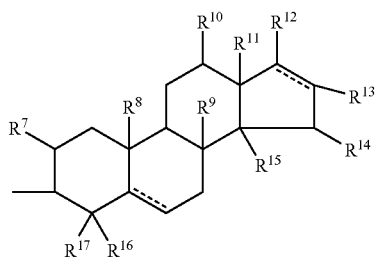

the group Z incorporating additional group (VIa) or (VIc)

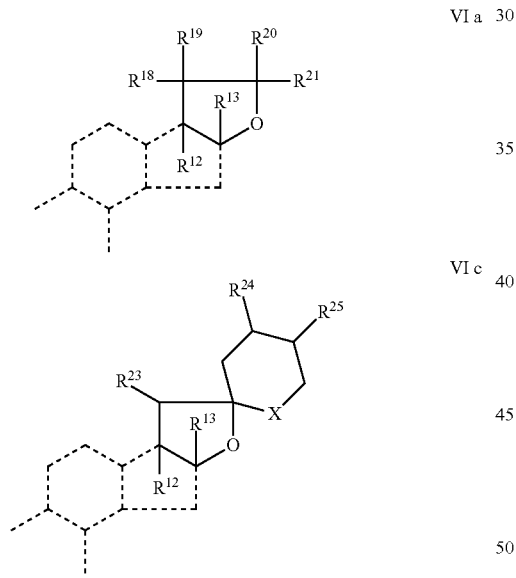

wherein:
when the steroid group incorporates additional group (VIa):
$R^7$, $R^{12}$, $R^{14}$, $R^{15}$ and $R^{19}$ are independently selected from H and —OH;
$R^8$, $R^{11}$ and $R^{18}$ are —CH$_3$;
$R^9$, $R^{13}$, $R^{16}$ and $R^{17}$ are H;
$R^{10}$ is H or —OH or the H normally present is absent and $R^{10}$ is =O;
$R^{19}$ is H or —OH;
$R^{20}$ is H, —OH or —OCH$_3$ or $R^{19}$ and $R^{20}$ taken together represent the second bond of a double bond joining adjacent carbon atoms;
$R^{21}$ is selected from the group consisting of 3-methylenebutyl substituted at the 4-position by glucose, 4-hydroxy-3-methylbutanyl, 3-methylbutanyl substituted at the 4-position by glucose, 1-hydroxy-3-methylbutanyl substituted at the 4-position by glucose or 1-methoxy-3-methylbutanyl substituted at the 4-position by glucose; and

----- represents either a single bond or a double bond;
and wherein when the steroid group incorporates additional group (VIc):
$R^7$, $R^{12}$, $R^{14}$, $R^{15}$ and $R^{24}$ are independently selected from H and —OH;
$R^8$, $R^{11}$ and $R^{23}$ are —CH$_3$;
$R^9$, $R^{13}$, $R^{16}$ and $R^{17}$ are H;
$R^{10}$ is H or —OH or the H normally present is absent and $R^{10}$ is =O;
$R^{25}$ is —CH$_3$, —CH$_2$OH, or =CH$_2$;
X is O or NH; and

----- represents either a single bond or a double bond;
or a pharmaceutically acceptable salt, ether or ester form thereof; and
wherein the condition associated with detrimental activity of Core 2 GlcNAc-T is selected from the group consisting of: vascular diseases, autoimmune conditions, inflammatory conditions, Wiskott Aldrich syndrome and cancer metastasis.

22. A method according to claim 21 in which X is O.

23. A method according to claim 21 wherein when the steroid group incorporates additional group (VIa);
$R^7$, $R^9$, $R^{10}$, $R^{13}$, $R^{14}$, $R^{16}$, $R^{17}$ and $R^{19}$ are H; $R^{12}$ is H or —OH; $R^8$, $R^{11}$ and $R^{18}$ are —CH$_3$; $R^{15}$ is H or —OH; $R^{20}$ is —OH or —OCH$_3$ and $R^{21}$ is 4-hydroxy-3-methylbutanyl, 3-methylenebutyl substituted at the 4-position by glucose, 3-methylbutanyl substituted at the 4-position by glucose, 1-hydroxy-3-methylbutanyl substituted at the 4-position by glucose or 1-methoxy-3-methylbutanyl substituted at the 4-position by glucose.

24. A method according to claim 21 wherein the group Z incorporating additional group (VIa) is selected from the group consisting of:

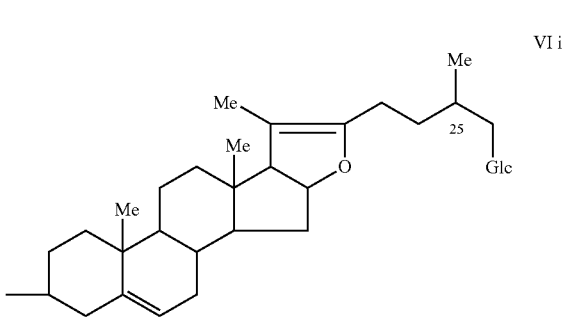

VI ii
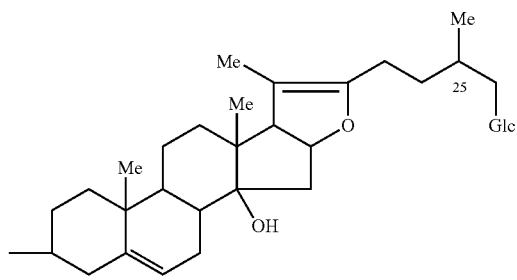
VI iii
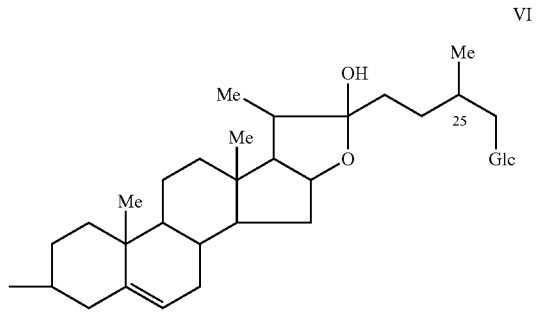
VI iv
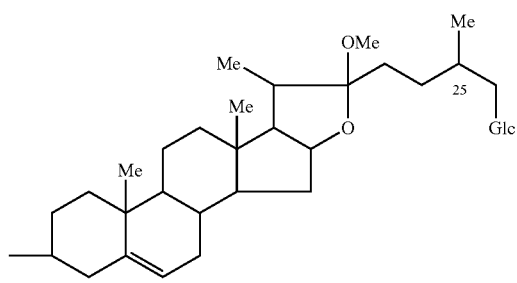
VI v
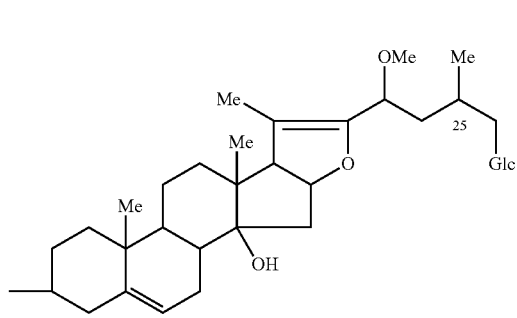
VI vi
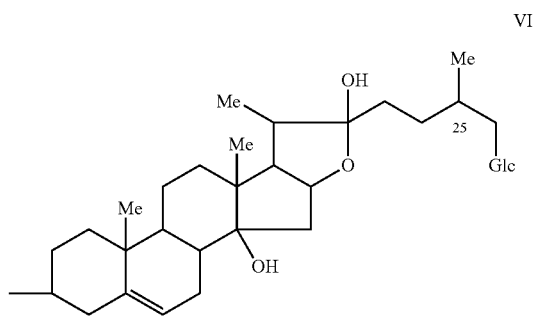
VI vii
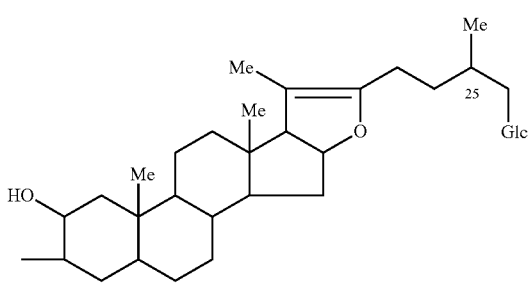
VI viii
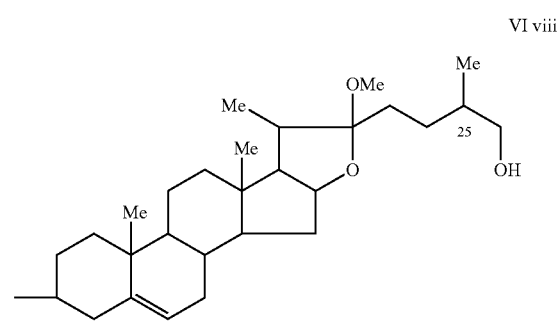
VI ix
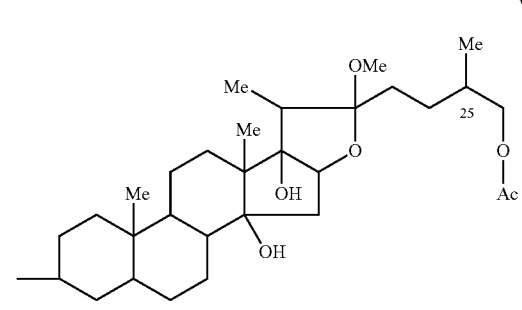
VI x
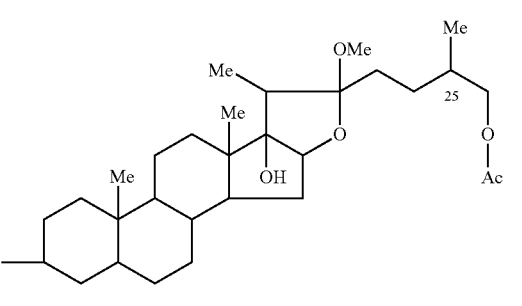
VI xi
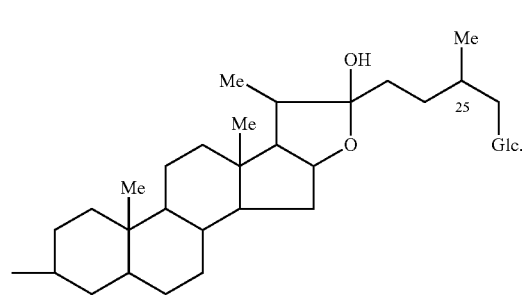

25. A method according to claim 21 wherein the group Z incorporating additional group (VIc) is selected from the group consisting of:
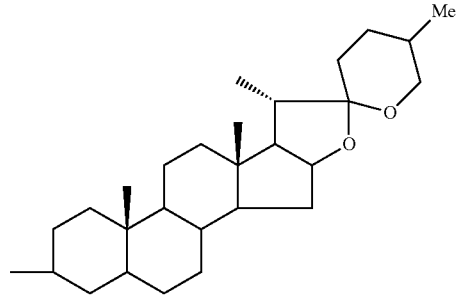
VI xv
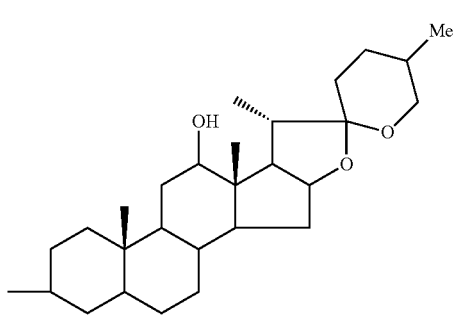
VI xvi
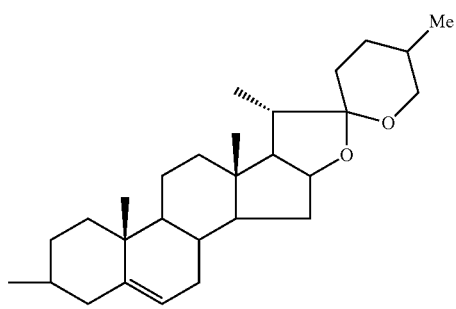
V xvii
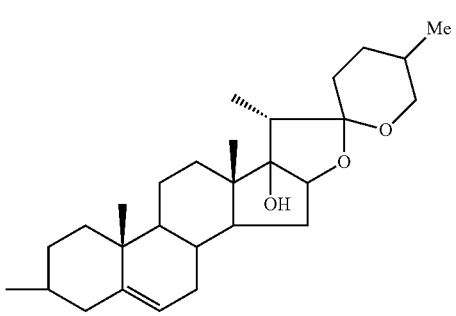
V xviii
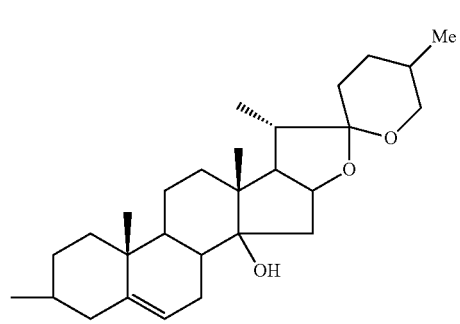
V xix
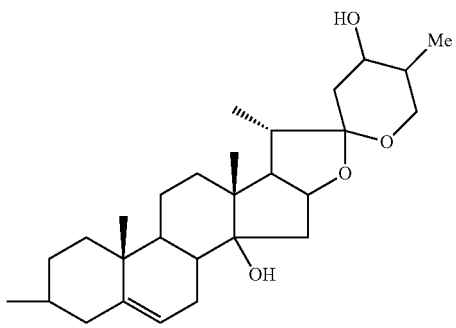
V xx
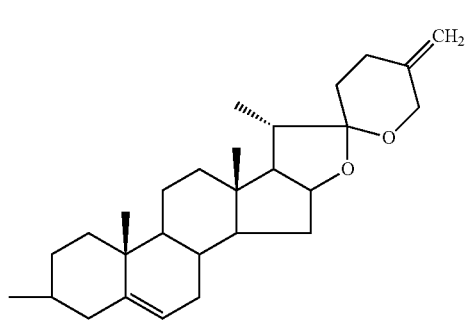
VI xxi
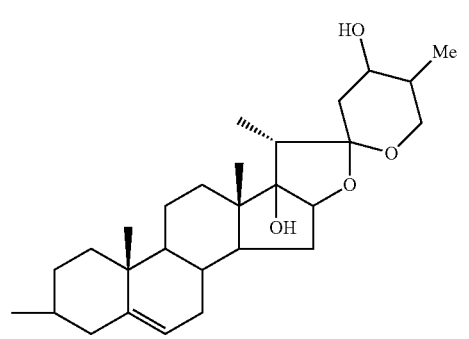
VI xxii
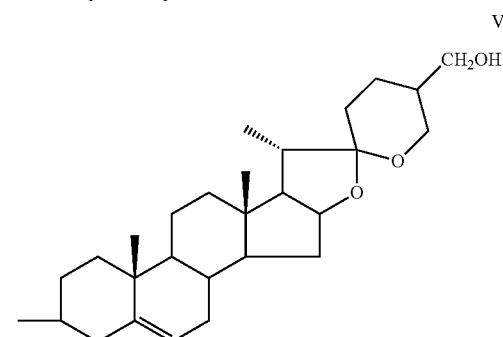
VI xxiii
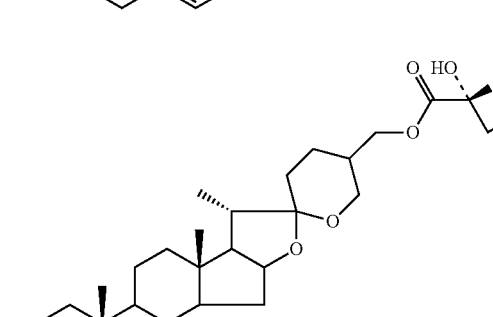
VI xxiv -continued

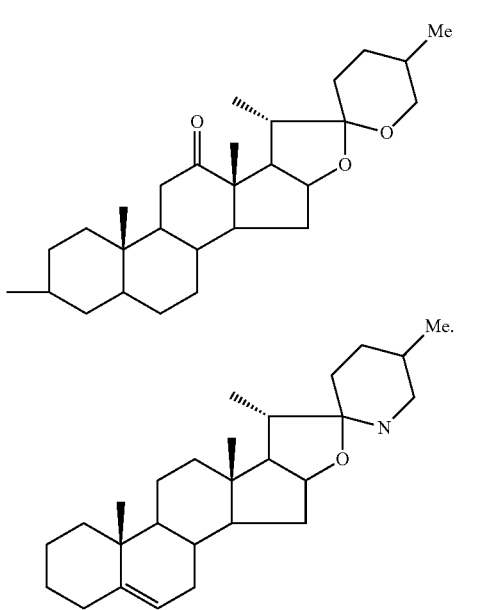

VI xxv

Me.

26. A method according to claim 21 in which the compound is selected from the group consisting of:
Trigoneoside IVa, glycoside F, Pardarinoside C, Pardarinoside D, Balanitin VI, Deltonin, Shatavarin I, Shatavarin IV, compound 8, compound 12, compound 13, compound 14, compound 15, compound 16, compound 17, compound 18, compound 25 and compound 26.

27. A method of treatment according to claim 21 wherein the condition to be treated is selected from diabetic retinopathy, diabetic cardiomyopathy and diabetic nephropathy.

28. A method of treatment according to claim 21 wherein the condition to be treated is atherosclerosis.

29. A method of treatment according to claim 21 wherein the condition to be treated is rheumatoid arthritis.

30. A method of treatment according to claim 21 wherein the condition to be treated is asthma.

31. A method of treatment according to claim 21 wherein the condition to be treated is cancer metastasis.

32. A method of treatment according to claim 21 wherein the condition to be treated is multiple sclerosis.

33. A method of treatment according to claim 21 wherein the condition to be treated is selected from inflammatory bowel disease, ileitis, Crohn's disease, cholitis, pancreatitis, ulcerative cholitis, cholicystitis, nephritis, gastritis, diverticulitis, gastric and duodenal ulcers and irritable bowel syndrome.

34. A method of treatment according to claim 21 wherein the condition to be treated is psoriasis.

35. A method of treatment according to claim 21 wherein the condition to be treated is acute leukocyte mediated lung injury.

36. A method of treatment according to claim 21 wherein the condition to be treated is selected from ischemia reperfusion injury, restenosis and thrombosis.

37. A method of treatment according to claim 21 wherein the condition to be treated is lupus.

38. A method of treatment according to claim 21 wherein the condition to be treated is selected from traumatic shock and septic shock.

39. A method of treatment according to claim 21 wherein the condition to be treated is Wiskott-Aldrich syndrome.

40. A method of treatment according to claim 21 wherein the condition to be treated is selected from cirrhosis, fulminant hepatitis, hepatorenal syndrome and jaundice.

41. A method of treatment according to claim 1 or claim 21 wherein the compound of the formula (III) is of at least 10% purity.

42. A method of treatment according to claim 1 or claim 21 wherein the compound of the formula (III) is of at least 30% purity.

43. A method of treatment according to claim 1 or claim 21 wherein the compound of the formula (III) is of at least 50% purity.

44. A method of treatment according to claim 1 or claim 21 wherein the compound of the formula (III) is of at least 80% purity.

45. A method of treatment according to claim 1 or claim 21 wherein the compound of the formula (III) is of at least 90% purity.

46. A method of treatment according to claim 1 or claim 21 wherein the compound of the formula (III) is of at least 95% purity.

47. A method of treatment according to claim 1 or claim 21 wherein the compound of the formula (III) is a component of a pharmaceutical composition which additionally comprises a pharmaceutically acceptable diluent or excipient.

48. A method of treatment according to claim 1 or claim 21 wherein the compound of the formula (III) is in the form of a plant extract.

49. A method of treatment according to claim 1 or claim 21 wherein the compound of the formula (III) is administered by the parenteral route.

50. A method of treatment according to claim 1 or claim 21 wherein the compound of the formula (III) is administered by the transdermal route.

51. A method of treatment according to claim 1 or claim 21 wherein the compound of the formula (III) is administered by the rectal, vaginal buccal or sublingual routes.

52. A method of treatment according to claim 1 or claim 21 wherein the compound of the formula (III) is incorporated into a food or beverage product.

53. A method of treatment according to claim 1 wherein the vascular disease is a vascular complication of diabetes.

54. A method of treatment according to claim 21 wherein the vascular disease is a vascular complication of diabetes.

* * * * *